US012631562B2

(12) United States Patent
Haji Reza et al.

(10) Patent No.: US 12,631,562 B2
(45) Date of Patent: May 19, 2026

(54) PHOTOABSORPTION REMOTE SENSING (PARS) IMAGING METHODS

(71) Applicant: ILLUMISONICS INC., Waterloo (CA)

(72) Inventors: Parsin Haji Reza, Waterloo (CA); Kevan Bell, Waterloo (CA); Benjamin Eccelstone, Waterloo (CA); Vladimir Pekar, Waterloo (CA); Nicholas Pellegrino, Waterloo (CA); Paul Fieguth, Waterloo (CA); James Alexander Tummon Simmons, Waterloo (CA); James Tweel, Waterloo (CA)

(73) Assignee: ILLUMISONICS INC., Waterloo (CA)

( * ) Notice: Subject to any disclaimer, the term of this patent is extended or adjusted under 35 U.S.C. 154(b) by 109 days.

(21) Appl. No.: 18/560,514

(22) PCT Filed: May 12, 2022

(86) PCT No.: PCT/IB2022/054433
§ 371 (c)(1),
(2) Date: Nov. 13, 2023

(87) PCT Pub. No.: WO2022/238956
PCT Pub. Date: Nov. 17, 2022

(65) Prior Publication Data
US 2024/0255427 A1    Aug. 1, 2024

Related U.S. Application Data

(63) Continuation-in-part of application No. 17/394,919, filed on Aug. 5, 2021, now Pat. No. 11,786,128, and
(Continued)

(51) Int. Cl.
*G01N 21/64* (2006.01)
*A61B 5/00* (2006.01)
(Continued)

(52) U.S. Cl.
CPC ....... *G01N 21/6456* (2013.01); *A61B 5/0071* (2013.01); *G01N 21/47* (2013.01);
(Continued)

(58) Field of Classification Search
CPC ............. A61B 5/0095; G01N 21/1702; G01N 2021/1706; G01N 21/1717;
(Continued)

(56) References Cited

U.S. PATENT DOCUMENTS 5,070,733 A    12/1991    Nagata et al.
5,479,259 A    12/1995    Nakata et al.
(Continued)

FOREIGN PATENT DOCUMENTS

CN    101526483 A    9/2009
CN    103048271 A    4/2013
(Continued)

OTHER PUBLICATIONS

Hongli Ni et al; "Millimeter-deep micron-resolution vibrational imaging by shortwave infrared photothermal microscopy" Published Jun. 25, 2024; (Year: 2024).*
(Continued)

*Primary Examiner* — Don K Wong
(74) *Attorney, Agent, or Firm* — Bookoff McAndrews, PLLC

(57) ABSTRACT

A method of visualizing details in a sample may comprise generating radiative and non-radiative signals in the sample at an excitation location using an excitation beam, interrogating the sample with an interrogation beam directed toward the excitation location of the sample, and detecting light from the sample. The excitation beam may be focused below a surface of the sample. The interrogation beam may be focused below the surface of the sample. The detected light may include a portion of the interrogation beam
(Continued)

returning from the sample. The detected light may be indicative of the generated radiative an non-radiative signals.

24 Claims, 35 Drawing Sheets

Related U.S. Application Data a continuation-in-part of application No. PCT/ IB2021/055380, filed on Jun. 17, 2021.

(60) Provisional application No. 63/315,215, filed on Mar. 1, 2022, provisional application No. 63/241,170, filed on Sep. 7, 2021, provisional application No. 63/187,789, filed on May 12, 2021.

(51) Int. Cl.
*G01N 21/47* (2006.01)
*G06V 10/56* (2022.01)
*G06V 10/762* (2022.01)
*G06V 20/69* (2022.01)

(52) U.S. Cl.
CPC ............ *G06V 10/56* (2022.01); *G06V 10/762* (2022.01); *G06V 20/698* (2022.01)

(58) Field of Classification Search
CPC . G01N 2021/1725; G01N 2201/06113; G01N 2201/08; G01N 21/6456; G01N 21/6486; G01N 29/2418; G01N 29/4436
See application file for complete search history.

(56) References Cited

U.S. PATENT DOCUMENTS

| | | | |
|---|---|---|---|
| 5,615,675 A | 4/1997 | O'Donnell et al. | |
| 5,991,479 A | 11/1999 | Kleinerman | |
| 6,016,202 A | 1/2000 | Fuchs et al. | |
| 6,078,397 A | 6/2000 | Monchalin et al. | |
| 6,256,100 B1 | 7/2001 | Banet et al. | |
| 6,973,830 B2 | 12/2005 | Pepper et al. | |
| 6,992,829 B1 | 1/2006 | Jennings et al. | |
| 7,068,842 B2 | 6/2006 | Liang et al. | |
| 8,004,689 B2 | 8/2011 | Monchalin et al. | |
| 8,180,134 B2 | 5/2012 | Wang | |
| 8,454,512 B2 | 6/2013 | Wang et al. | |
| 8,692,155 B2 | 4/2014 | Bischoff et al. | |
| 9,057,778 B2 | 6/2015 | Gurton et al. | |
| 9,153,931 B2 | 10/2015 | Ichihara et al. | |
| 9,999,354 B2 | 6/2018 | Rousseau et al. | |
| 10,117,583 B2 * | 11/2018 | Reza .................. | G01N 21/1717 |
| 10,682,061 B2 * | 6/2020 | Reza .................... | A61B 5/0095 |
| 11,298,027 B2 * | 4/2022 | Haji Reza .......... | G01N 21/1717 |
| 11,774,354 B2 | 10/2023 | Prater et al. | |
| 11,786,128 B2 * | 10/2023 | Haji Reza .......... | G01N 21/6456 600/425 |
| 2006/0184042 A1 | 8/2006 | Wang et al. | |
| 2006/0262316 A1 | 11/2006 | Baney | |
| 2008/0123083 A1 | 5/2008 | Wang et al. | |
| 2008/0194929 A1 | 8/2008 | Pesach et al. | |
| 2009/0170149 A1 | 7/2009 | Viator et al. | |
| 2010/0068752 A1 | 3/2010 | Pande et al. | |
| 2010/0268042 A1 | 10/2010 | Wang et al. | |
| 2012/0061586 A1 | 3/2012 | Yao et al. | |
| 2012/0200845 A1 | 8/2012 | Rousseau et al. | |
| 2012/0320368 A1 | 12/2012 | Jiao et al. | |
| 2013/0281889 A1 | 10/2013 | Gertner | |
| 2014/0009808 A1 | 1/2014 | Wang et al. | |
| 2014/0118749 A1 | 5/2014 | Nakajima et al. | |
| 2014/0185055 A1 | 7/2014 | Wang | |
| 2014/0247456 A1 | 9/2014 | Horstmann et al. | |
| 2015/0031990 A1 | 1/2015 | Boctor et al. | |
| 2015/0077819 A1 | 3/2015 | Schnell et al. | |
| 2015/0148655 A1 | 5/2015 | Haupt et al. | |
| 2015/0150465 A1 | 6/2015 | Irisawa et al. | |
| 2015/0153269 A1 | 6/2015 | Nakatsuka | |
| 2015/0164337 A1 | 6/2015 | Kim et al. | |
| 2015/0185187 A1 | 7/2015 | Wang et al. | |
| 2015/0221081 A1 | 8/2015 | Chang et al. | |
| 2015/0265156 A1 | 9/2015 | Tanaka | |
| 2016/0011175 A1 | 1/2016 | Gostjeva et al. | |
| 2016/0113507 A1 | 4/2016 | Reza et al. | |
| 2016/0156148 A1 | 6/2016 | Thomsen et al. | |
| 2016/0249812 A1 | 9/2016 | Wang et al. | |
| 2017/0215738 A1 | 8/2017 | Haji Reza et al. | |
| 2018/0275046 A1 | 9/2018 | Haji Reza et al. | |
| 2019/0104944 A1 | 4/2019 | Haji Reza et al. | |
| 2020/0237228 A1 | 7/2020 | Bhawalkar | |
| 2020/0379227 A1 | 12/2020 | Calvin | |
| 2022/0068496 A1 | 3/2022 | Khan et al. | |
| 2023/0175965 A1 | 6/2023 | Cheng et al. | |

FOREIGN PATENT DOCUMENTS

| | | |
|---|---|---|
| CN | 106124469 A | 11/2016 |
| CN | 108102408 A | 6/2018 |
| CN | 109363639 A | 2/2019 |
| CN | 110823809 A | 2/2020 |
| CN | 111999278 A | 11/2020 |
| DE | 102010012809 A1 | 9/2011 |
| WO | 2013166044 A1 | 11/2013 |
| WO | 2014027316 A2 | 2/2014 |
| WO | 2014036405 A2 | 3/2014 |
| WO | 2014062529 A1 | 4/2014 |
| WO | 2014160116 A1 | 10/2014 |
| WO | 2014168930 A1 | 10/2014 |
| WO | 2020075548 A1 | 4/2020 |
| WO | 2020222300 A1 | 11/2020 |
| WO | 2022221290 A1 | 10/2022 |
| WO | 2023212402 A1 | 11/2023 |

OTHER PUBLICATIONS

Beard, Paul. "Biomedical Photoacoustic Imaging." Interface Focus 1.4 (2011): 602-631. PMC. Web. Dec. 12, 2017.

Hongli Ni et al., "Millimeter-deep micron-resolution vibrational imaging by shortwave infrared photothermal microscopy.".

Kevan L. Bell et al., "Coherence-gated photoacoustic remote sensing microscopy", Optics Express, vol. 26, No. 18, Sep. 3, 2018, 16 pp.

Zhihua Ding et al., "Real-time phase-resolved optical coherence tomography and optical Doppler tomography", Optics Express, vol. 10, No. 5, Mar. 11, 2002, 10 pages.

Cedric Blatter et al., "Intrasweep phase-sensitive optical coherence tomography for noncontact optical photoacoustic imaging", Optics Letters, vol. 37, No. 21, Nov. 1, 2012, 4 pp.

Tavakolian et al., "Perspective: Principles and specifications of photothermal imaging methodologies and their applications to noninvasive biomedical and non-destructive materials imaging," J. Appl. Phys. 124, 160903 (2018) (13 pages).

Adhikari et al, "Photothermal Microscopy: Imaging the Optical Absorption of Single Nanoparticles and Single Molecules," ACS Nano 2020, 14 (12), 16414-16445 (32 pages).

Restall Brendon S., et al: "Multispectral photoacoustic remote sensing microscopy using 532nm and 266nm excitation wavelengths", Progress in Biomedical Optics and Imaging, SPIE—International Society for Optical Engineering, Bellingham, WA, US, vol. 11240, Feb. 17, 2020 (Feb. 17, 2020), pp. 112404C-1 to 112404C-, XP060129590.

* cited by examiner

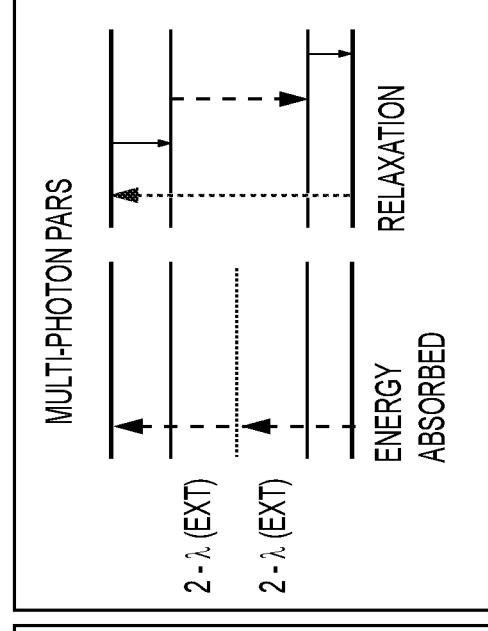
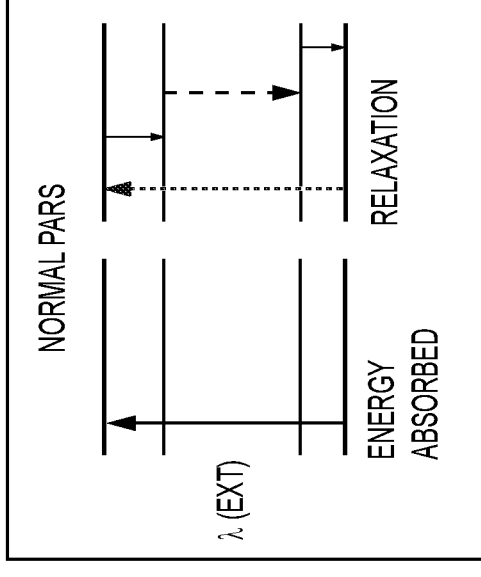
*FIG. 19*

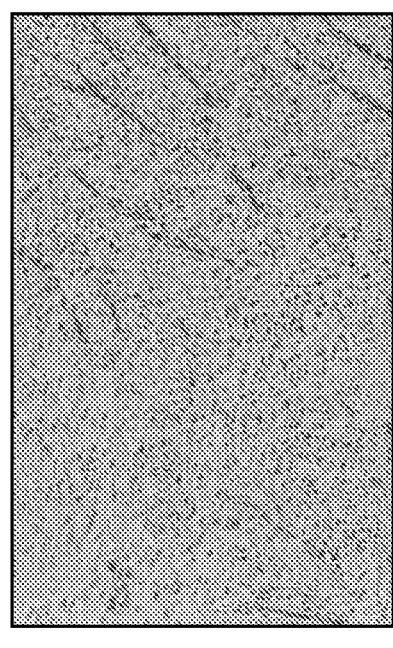
*FIG. 21B*
*FIG. 21A*

---

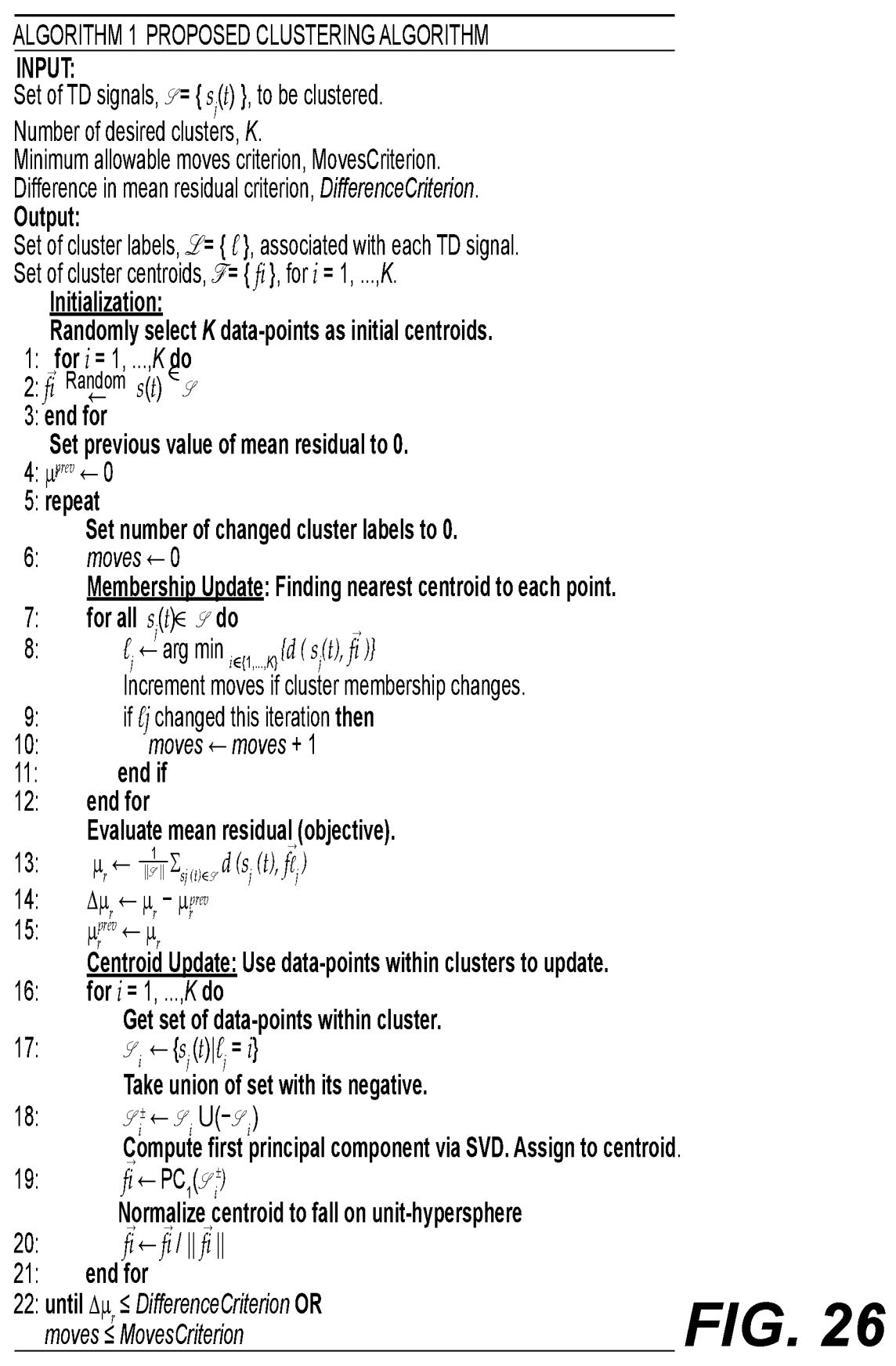

ALGORITHM 1 PROPOSED CLUSTERING ALGORITHM
_____

INPUT:

Set of TD signals, $\mathscr{S} = \{ s_j(t) \}$, to be clustered.

Number of desired clusters, $K$.

Minimum allowable moves criterion, MovesCriterion.

Difference in mean residual criterion, *DifferenceCriterion*.

Output:

Set of cluster labels, $\mathscr{L} = \{ \ell \}$, associated with each TD signal.

Set of cluster centroids, $\mathscr{F} = \{ \vec{f_i} \}$, for $i = 1, ..., K$.

<u>Initialization:</u>

Randomly select $K$ data-points as initial centroids.

1:   for $i = 1, ..., K$ do

2: $\vec{f_i} \overset{Random}{\leftarrow} s(t) \in \mathscr{S}$

3: end for

Set previous value of mean residual to 0.

4: $\mu^{prev} \leftarrow 0$

5: repeat

Set number of changed cluster labels to 0.

6:     *moves* $\leftarrow 0$

<u>Membership Update</u>: Finding nearest centroid to each point.

7:     for all $s_j(t) \in \mathscr{S}$ do

8:       $\ell_j \leftarrow \arg\min_{i \in \{1,...,K\}} \{ d(s_j(t), \vec{f_i}) \}$ Increment moves if cluster membership changes.

9:       if $\ell_j$ changed this iteration then

10:         *moves* $\leftarrow$ *moves* $+ 1$

11:       end if

12:     end for

Evaluate mean residual (objective).

13:     $\mu_r \leftarrow \frac{1}{\|\mathscr{S}\|} \Sigma_{s_j(t) \in \mathscr{S}} d(s_j(t), \vec{f\ell_j})$ 14:     $\Delta\mu_r \leftarrow \mu_r - \mu_r^{prev}$ 15:     $\mu_r^{prev} \leftarrow \mu_r$ <u>Centroid Update:</u> Use data-points within clusters to update.

16:     for $i = 1, ..., K$ do

Get set of data-points within cluster.

17:     $\mathscr{S}_i \leftarrow \{ s_j(t) | \ell_j = i \}$

Take union of set with its negative.

18:     $\mathscr{S}_i^{\pm} \leftarrow \mathscr{S}_i \cup (-\mathscr{S}_i)$

Compute first principal component via SVD. Assign to centroid.

19:     $\vec{f_i} \leftarrow PC_1(\mathscr{S}_i^{\pm})$

Normalize centroid to fall on unit-hypersphere

20:     $\vec{f_i} \leftarrow \vec{f_i} / \|\vec{f_i}\|$

21:     end for

22: until $\Delta\mu_r \leq$ *DifferenceCriterion* OR

*moves* $\leq$ *MovesCriterion*
_____

FIG. 26

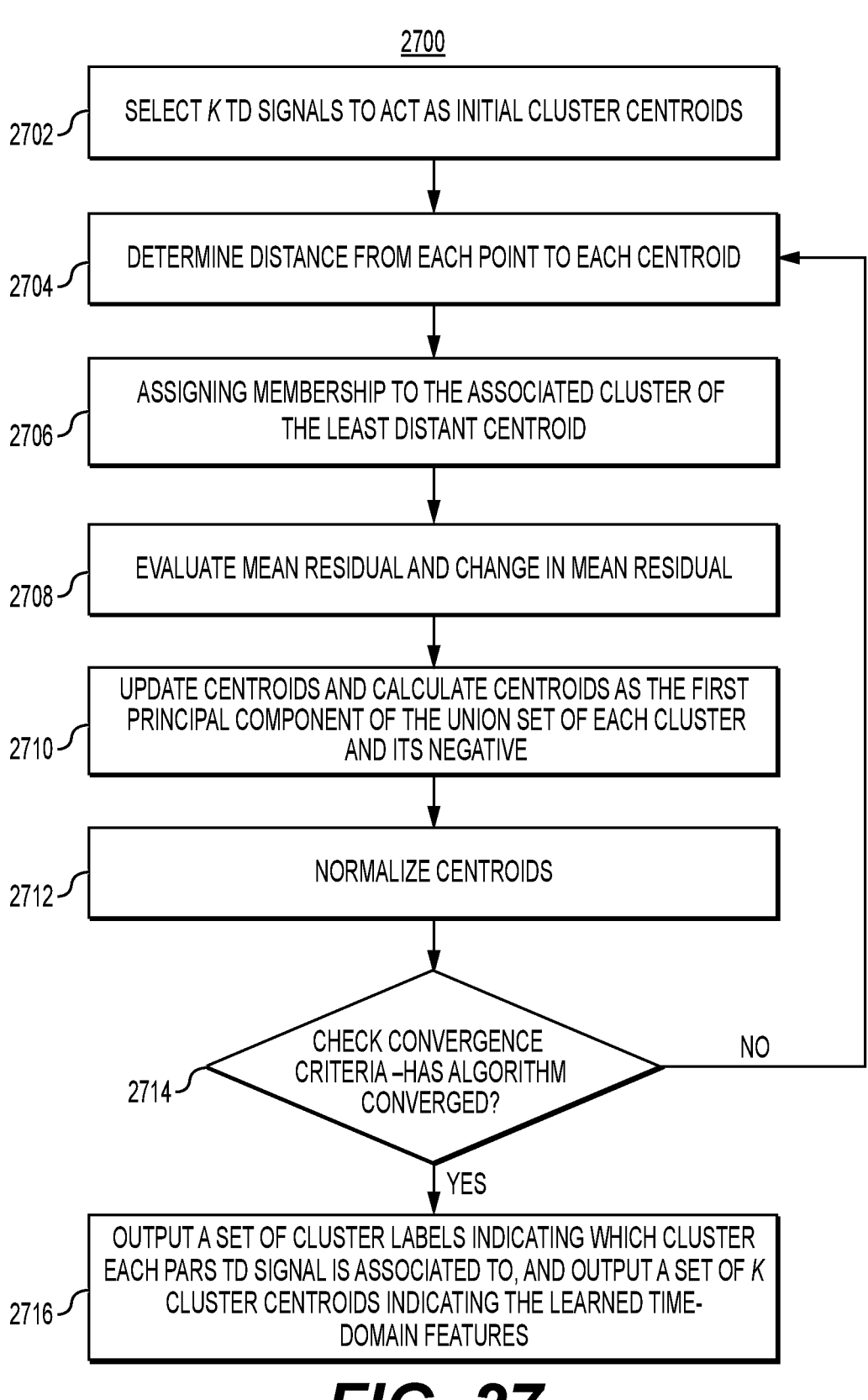

2700

2702 — SELECT K TD SIGNALS TO ACT AS INITIAL CLUSTER CENTROIDS

2704 — DETERMINE DISTANCE FROM EACH POINT TO EACH CENTROID

2706 — ASSIGNING MEMBERSHIP TO THE ASSOCIATED CLUSTER OF THE LEAST DISTANT CENTROID

2708 — EVALUATE MEAN RESIDUAL AND CHANGE IN MEAN RESIDUAL

2710 — UPDATE CENTROIDS AND CALCULATE CENTROIDS AS THE FIRST PRINCIPAL COMPONENT OF THE UNION SET OF EACH CLUSTER AND ITS NEGATIVE

2712 — NORMALIZE CENTROIDS

2714 — CHECK CONVERGENCE CRITERIA –HAS ALGORITHM CONVERGED?

NO

YES

2716 — OUTPUT A SET OF CLUSTER LABELS INDICATING WHICH CLUSTER EACH PARS TD SIGNAL IS ASSOCIATED TO, AND OUTPUT A SET OF K CLUSTER CENTROIDS INDICATING THE LEARNED TIME-DOMAIN FEATURES

*FIG. 27*

PAW PARS
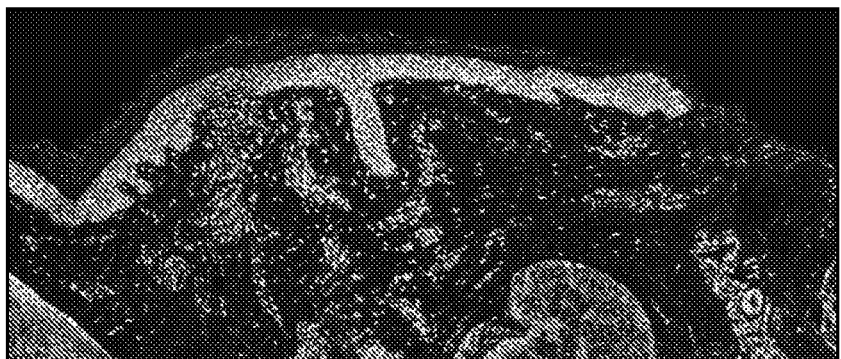
K-MEANS VISUALIZATION
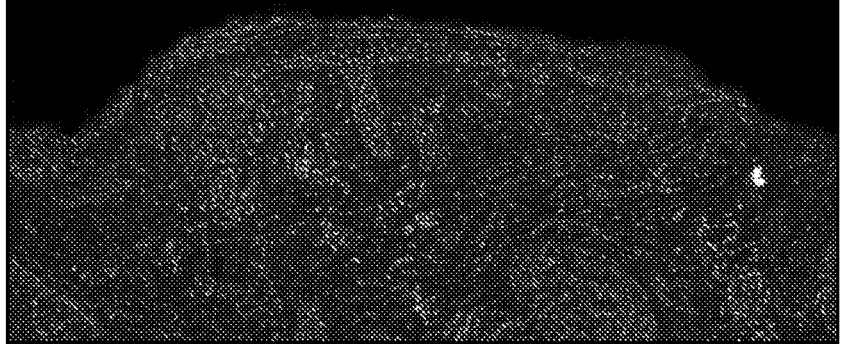
VIRTUALLY STAINED H&E
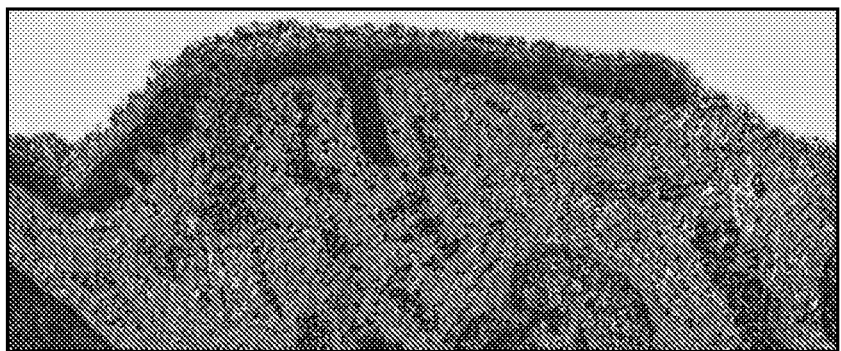
*FIG. 37*

PHOTOABSORPTION REMOTE SENSING (PARS) IMAGING METHODS

CROSS-REFERENCE TO RELATED APPLICATIONS

This is a National Stage Application under 35 U.S.C. § 371 of International Application No. PCT/IB2022/054433, filed on May 12, 2022, now published as WO 2022/28956 A1, which claims priority to:

U.S. Provisional Patent Application No. 63/187,789, filed on May 12, 2021,

U.S. Provisional Patent Application No. 63/241,170, filed on Sep. 7, 2021

U.S. Provisional Patent Application No. 63/315,215, filed on Mar. 1, 2022

U.S. patent application Ser. No. 17/394,919, filed on Aug. 5, 2021

Which is a con of PCT/IB2021/055380 filed Jun. 17, 2021

PCT/IB2021/055380 claims benefit to 63/187,789, filed on May 12, 2021 (above), claims benefit to 63/040,866 filed on Jun. 16, 2020 (0007-01600), and is a CIP of 17/010,500, filed on Sep. 2, 2020 (0007-02000)

17/010,500 claims benefit to 63/040,866 filed on Jun. 16, 2020 (0007-01600)

PCT/IB2021/055380 filed Jun. 17, 2021 Which claims benefit to 63/187,789, filed on May 12, 2021 (above) the entireties of which are incorporated herein by reference.

FIELD

This relates to the field of optical imaging and, in particular, to a photoabsorption remote sensing (PARS) system for non-contact imaging of samples such as industrial materials or biological tissue in vivo, ex vivo, or in vitro.

BACKGROUND

Photoacoustic imaging can be split into two main categories: Photoacoustic tomography (PAT) uses reconstruction-based image formation, while photoacoustic microscopy (PAM) uses focused-based image formation. Since conventional photoacoustic techniques require physical coupling to the sample, they are inappropriate for a wide variety of clinical applications such as ophthalmic imaging, intraoperative imaging, monitoring of wound healing, and many endoscopic procedures.

SUMMARY

Aspects disclosed herein may provide a method of visualizing details in a sample. The method may include generating radiative and non-radiative signals in the sample at an excitation location using an excitation beam, interrogating the sample with an interrogation beam directed toward the excitation location of the sample, and detecting light from the sample.

The excitation beam may be focused below a surface of the sample. The interrogation beam may be focused below the surface of the sample. The detected light may include a portion of the interrogation beam returning from the sample. The detected light may be indicative of the generated radiative and non-radiative signals.

The returned portion of the interrogation beam may be indicative of the generated non-radiative signals. A portion of the detected light that excludes the returned portion of the interrogation beam and the excitation beam may be indicative of the generated radiative signals.

The method may include detecting local optical scattering from the sample.

Detecting the light may include detecting the generated radiative and non-radiative signals over time. The method may include determining an evolution time of the detected generated radiative and non-radiative signals.

Generating radiative and non-radiative signals in the sample may occur at a plurality of regions in the sample. The method may include determining or identifying regions among the plurality of regions that belong to cell nuclei based on the determined evolution time.

The method may include determining, based on the determined evolution time, at least one of a thermal diffusivity of the sample, a conductivity of the sample, a speed of sound in the sample, a temperature of the sample, a density of the sample, a heat capacity of the sample, an acoustic impedance of the sample, a tissue type of the sample, or molecular information of the sample.

The method may include determining an average pre-excitation signal, determining an average post-excitation signal based on a predetermined portion of the detected signals over time, and determining an amplitude based on a difference between the determined average pre-excitation signal and the determined average post-excitation signal.

The method may include determining a value using a function based on the detected generated radiative PARS signals and the non-radiative PARS signals. The value may be a ratio of the detected generated radiative PARS signals to the non-radiative PARS signals.

The method may include redirecting a portion of the returned interrogation beam and detecting an interaction with the sample.

A wavelength of the excitation beam may be configured such that the sample absorbs two or more photons simultaneously. A sum of energy of the two or more photons may be equal to a predetermined energy or absorption.

A wavelength of the excitation beam may be configured such that the sample absorbs two or more photons simultaneously. The wavelength may be equal to twice a predetermined wavelength. The predetermined wavelength may be a wavelength in the ultraviolet (UV) range. The predetermined wavelength may be a wavelength in the UVC range.

The method may include clustering the detected generated radiative and non-radiative signals based on shape using a clustering algorithm to determine features of the sample. The method may include determining cluster centroids based on the clustered signals and determining an image based on the clustered signals. The method may include determining one or more colors based on the clustered signals.

Interrogating the sample with an interrogation beam may include moving the interrogation beam over the sample to interrogate the sample over a plurality of regions over time.

The method may include estimating non-modulated scattering caused by the movement of the interrogation beam over spatial variations of the sample.

The method may include measuring or storing a plurality of filtered-instances of one of the generated signals. The plurality of filtered-instances may include an unfiltered instance of the signal and a filtered instance of the signal.

The method may include determining a first image based on the detected generated radiative signals and determining a second image based on the detected generated non-radiative signals, comparing the first and second images, and determining one or more modifications to a final image of the sample based on the comparison.

The interrogation beam may include a chirped-pulse. The method may include spatially separating various wavelength components of the interrogation beam.

Detecting the light from the sample may be performed using a plurality of detectors. At least one of the plurality of detectors may be sensitive to or configured to detect radiative relaxation. At least one of the plurality of detectors may be configured to detect fluorescence or autofluorescence and/or may be sensitive to fluorescence or autofluorescence.

The excitation beam may be focused in an area that may be smaller than an area in which the detection beam may be focused.

The method may be used in one or more of the following applications: imaging of blood oxygen saturation, imaging of tumor hypoxia, imaging of wound healing, burn diagnostics, or surgery, imaging of microcirculation, blood oxygenation parameter imaging, estimating blood flow in vessels flowing into and out of a region of tissue, imaging of molecularly-specific targets, imaging angiogenesis for preclinical tumor models, clinical imaging of micro- and macro-circulation and pigmented cells, imaging of the eye, augmenting or replacing fluorescein angiography, imaging dermatological lesions, imaging melanoma, imaging basal cell carcinoma, imaging hemangioma, imaging psoriasis, imaging eczema, imaging dermatitis, imaging Mohs surgery, imaging to verify tumor margin resections, imaging peripheral vascular disease, imaging diabetic and/or pressure ulcers, burn imaging, plastic surgery, microsurgery, imaging of circulating tumor cells, imaging melanoma cells, imaging lymph node angiogenesis, imaging response to photodynamic therapies, imaging response to photodynamic therapies having vascular ablative mechanisms, imaging response to chemotherapeutics, imaging response to anti-angiogenic drugs, imaging response to radiotherapy, estimating oxygen saturation using multi-wavelength photoacoustic excitation, estimating venous oxygen saturation where pulse oximetry cannot be used, estimating cerebrovenous oxygen saturation and/or central venous oxygen saturation, estimating oxygen flux and/or oxygen consumption, imaging vascular beds and depth of invasion in Barrett's esophagus and/or colorectal cancers, functional imaging during brain surgery, assessment of internal bleeding and/or cauterization verification, imaging perfusion sufficiency of organs and/or organ transplants, imaging angiogenesis around islet transplants, imaging of skin-grafts, imaging of tissue scaffolds and/or biomaterials to evaluate vascularization and/or immune rejection, imaging to aid microsurgery, guidance to avoid cutting blood vessels and/or nerves, imaging of contrast agents in clinical or pre-clinical applications, identification of sentinel lymph nodes, non- or minimally-invasive identification of tumors in lymph nodes, non-destructive testing of materials, imaging of genetically-encoded reporters, wherein the genetically-encoded reporters may include tyrosinase, chromoproteins, and/or fluorescent proteins for pre-clinical or clinical molecular imaging applications, imaging actively or passively targeted optically absorbing nanoparticles for molecular imaging, imaging of blood clots, staging an age of blood clots, replacing a catheterization procedure, gastroenterological applications, single-excitation pulse imaging over an entire field of view, imaging of tissue, imaging of cells, imaging of scattered light from object surfaces, imaging of absorption-induced changes of scattered light, or non-contact imaging of optical absorption.

Aspects disclosed herein may provide a method of visualizing features in a sample. The method may include the steps of receiving signals over a period of time, determining features of the sample based on an evolution of the received signals over the period of time, and determining an image based on the determined features. The signals may include non-radiative and radiative signals from the sample.

The method may include splitting one of the received signals into two or more instances, filtering one of the instances, and recording the two or more instances on two or more channels, respectively.

The method may include plotting the received signals along a first spatial axis, a second spatial axis, and a time axis, and calculating a volume based on the plotted received signals.

The method may include displaying the determined image. The method may include displaying the determined image in combination with a secondary visualization. The secondary visualization may be a bright field image of the sample. The secondary visualization may appear as a background to the determined image.

Aspects disclosed herein may provide a method of visualizing features in a sample. The method may include the steps of receiving signals over a period of time, determining features of the sample based on an evolution of the received signals over the period of time, and determining an image based on the determined features. The received signals may indicate two or more unique absorption-based measurements in the sample. The two or more unique absorption-based measurements include radiative measurements and non-radiative measurements.

Aspects disclosed herein may provide a method of visualizing features in a sample. The method may include the steps of receiving signals, clustering the received one or more signals using a clustering algorithm to determine features of the sample, and determining an image based on the clustered signals. The signals may include non-radiative and radiative signals from the sample. At least some of the received signals may be collected by generating signals in the sample at an excitation location using an excitation beam, interrogating the sample with an interrogation beam directed toward the excitation location of the sample, and detecting a portion of the interrogation beam returning from the sample. At least some of the signals may be collected by detecting optical absorption and scattering from the sample.

The method may include determining cluster centroids based on the clustered signals, and determining characteristic time-domain signals based on the determined cluster centroids.

The clustering algorithm may be configured to, when executed, select a predetermined number of signals to act as initial cluster centroids, update a cluster membership of all signals, determine a mean residual and a change in the mean residual, determine cluster centroids and a first principle component, and determine whether convergence criteria is met. Updating a cluster membership may include determining a distance from each signal to each centroid and assigning membership to a cluster of the least distant centroid.

The method may include determining one or more colors used in the image based on the clustered signals and determined features.

Aspects disclosed herein may provide a photoabsorption remote sensing system for imaging features in a sample. The system may include an excitation light source configured to generate signals in the sample at an excitation location, an interrogation light source configured to interrogate the sample and directed toward the excitation location of the sample, and a processor configured to analyze the generated signals as a function of time and determine an image. The excitation light source may be focused below a surface of the sample. The interrogation light source may be focused below the surface of the sample. A portion of the at least one interrogation light source returning from the sample may be indicative of at least some of the generated signals. The image may be indicative of features in the sample.

A filter may be configured to separate the returned portion of the interrogation light source from a remaining portion of light from the sample. The processor may be configured to analyze the signals indicated in the returned portion of the sample and the signals indicated in the remaining portion of light.

The processor may be configured to execute a clustering algorithm to cluster the generated signals and determine the image based on the clustered generated signals.

The at least one excitation light source may include a first excitation light source and a second excitation light source. The first excitation light source may be configured to provide light at a first wavelength, and the second excitation light source may be configured to provide light at a second wavelength.

Aspects disclosed herein may provide a photoabsorption remote sensing system for imaging features in a sample. The system may include an excitation light source configured to generate signals in the sample at an excitation location, an interrogation light source configured to interrogate the sample and directed toward the excitation location of the sample, a detection source configured to detect light from the sample, the detection source may be configured to detect a portion of the interrogation light source returning from the sample, and a processor configured to analyze the generated signals as a function of time and determine an image. The excitation light source may be focused below a surface of the sample. The interrogation light source may be focused below the surface of the sample. The returned portion of the interrogation light source may be indicative of at least some of the generated signals. The image may be indicative of features in the sample.

The detection source may include a plurality of integrating photodetectors arranged such that a returning portion of the interrogation light source may be distributed across the plurality of integrating photodetectors.

The plurality of integrating photodetectors may be configured such that there may be a tunable delay between an integration start time of each photodetector. The detection source may include (i) one or more mechanical scanning stages and (ii) at least one of a resonant scanner or a polygon scanner.

Aspects disclosed herein may provide a computer-implemented method of visualizing features in a sample. The method may include the steps of receiving one or more photoabsorption remote sensing (PARS) signals, clustering the received one or more PARS signals using a clustering algorithm to determine features of the sample, and determining an image based on the clustered PARS signals.

At least some of the PARS signals may be collected by generating signals in the sample at an excitation location using an excitation beam, interrogating the sample with an interrogation beam directed toward the excitation location of the sample, and detecting a portion of the interrogation beam returning from the sample. The excitation beam being focused below a surface of the sample. The interrogation beam may be focused below the surface of the sample.

Generating signals may include generating pressure, temperature, and fluorescence signals. The returned portion of the interrogation beam may be indicative of the generated pressure and temperature signals. The PARS signals may be further collected by detecting fluorescence signals from the excitation location of the sample while detecting the generated pressure and temperature signals.

Generating signals may include generating radiative and non-radiative signals. The returned portion of the interrogation beam may be indicative of the generated non-radiative signals. The PARS signals may be further collected by detecting the radiative signals from the excitation location of the sample while simultaneously detecting the generated non-radiative signals.

The PARS signals may be further collected by redirecting a portion of the returned interrogation beam and detecting an interaction with the sample.

A wavelength of the excitation beam may be configured such that the sample absorbs two or more photons simultaneously. A sum of energy of the two or more photons may be equal to a predetermined energy.

The method may include collecting the PARS signals. Clustering the received PARS signals may be based on shape.

The method may not include analyzing a reconstructed grayscale image to determine the image. Clustering the received PARS signals may be not based on a scalar amplitude. The method may not include mapping or visualizing a scalar amplitude.

The PARS signals may be indicative of temperature characteristics of the sample. The PARS signals may be indicative of a speed of sound in the sample. The PARS signals may be indicative of molecular information. The PARS signals may be indicative of characteristics in the sample in an area having a size defined by a focused beam of light.

Receiving the PARS signals may include receiving time domain (TD) signals.

The method may include determining cluster centroids based on the clustered PARS signals. The determined cluster centroids may include characteristic time-domain signals.

Receiving the PARS signals may include receiving backscattering intensity, radiative signals, and non-radiative relaxation time-domain signals.

Receiving the PARS signals may include receiving radiative PARS signals and non-radiative PARS signals. The method further may include determining a ratio of the radiative PARS signals and the non-radiative PARS signals.

The method may include determining a decay time based on the received PARS signals. Determining the image may include determining one or more colors based on the clustering.

The method may be used in one or more of the following applications: imaging of blood oxygen saturation, imaging of tumor hypoxia, imaging of wound healing, burn diagnostics, or surgery, imaging of microcirculation, blood oxygenation parameter imaging, estimating blood flow in vessels flowing into and out of a region of tissue, imaging of molecularly-specific targets, imaging angiogenesis for preclinical tumor models, clinical imaging of micro- and macro-circulation and pigmented cells, imaging of the eye, augmenting or replacing fluorescein angiography, imaging dermatological lesions, imaging melanoma, imaging basal cell carcinoma, imaging hemangioma, imaging psoriasis, imaging eczema, imaging dermatitis, imaging Mohs surgery, imaging to verify tumor margin resections, imaging peripheral vascular disease, imaging diabetic and/or pressure ulcers, burn imaging, plastic surgery, microsurgery, imaging of circulating tumor cells, imaging melanoma cells, imaging lymph node angiogenesis, imaging response to photodynamic therapies, imaging response to photodynamic therapies having vascular ablative mechanisms, imaging response to chemotherapeutics, imaging response to anti-angiogenic drugs, imaging response to radiotherapy, estimating oxygen saturation using multi-wavelength photoacoustic excitation, estimating venous oxygen saturation where pulse oximetry cannot be used, estimating cerebrovenous oxygen saturation and/or central venous oxygen saturation, estimating oxygen flux and/or oxygen consumption, imaging vascular beds and depth of invasion in Barrett's esophagus and/or colorectal cancers, functional imaging during brain surgery, assessment of internal bleeding and/or cauterization verification, imaging perfusion sufficiency of organs and/or organ transplants, imaging angiogenesis around islet transplants, imaging of skin-grafts, imaging of tissue scaffolds and/or biomaterials to evaluate vascularization and/or immune rejection, imaging to aid microsurgery, guidance to avoid cutting blood vessels and/or nerves, imaging of contrast agents in clinical or pre-clinical applications, identification of sentinel lymph nodes, non- or minimally-invasive identification of tumors in lymph nodes, non-destructive testing of materials, imaging of genetically-encoded reporters, wherein the genetically-encoded reporters include tyrosinase, chromoproteins, and/or fluorescent proteins for pre-clinical or clinical molecular imaging applications, imaging actively or passively targeted optically absorbing nanoparticles for molecular imaging, imaging of blood clots, staging an age of blood clots, replacing a catheterization procedure, gastroenterological applications, single-excitation pulse imaging over an entire field of view, imaging of tissue, imaging of cells, imaging of scattered light from object surfaces, imaging of absorption-induced changes of scattered light, or non-contact imaging of optical absorption.

The method may include displaying the image on a display.

Aspects disclosed herein may provide a photoabsorption remote sensing (PARS) system for imaging features in a sample. The system may include an excitation light source configured to generate signals in the sample at an excitation location, an interrogation light source configured to interrogate the sample and directed toward the excitation location of the sample, and a processor configured to execute a clustering algorithm to cluster the generated signals and determine an image based on the clustered generated signals. The excitation light source may be focused below a surface of the sample.

The interrogation light source may be focused below the surface of the sample. A portion of the at least one interrogation light source may return from the sample that may be indicative of the generated signals. The image may be indicative of features in the sample.

The method may include a display configured to display the determined image. The image may be formed directly from the received signals.

The processor may be configured to determine one or more colors based on the clustering. The determined colors include purple, blue, and pink such that the image may be configured to resemble an hematoxylin and eosin (H&E) stained image.

Aspects disclosed herein may provide a computer-implemented method of visualizing features in a sample. The method may include the steps of receiving one or more signals, clustering the received signals based on shape using a clustering algorithm to determine time-domain features of the sample, and determining an image. The method may include determining one or more colors used in the image based on the clustered signals and determined time-domain features.

The method may include determining vector angles from the received one or more signals. Clustering the received signals based on shape may include clustering the received signals based on the vector angles. The one or more signals include at least one of non-radiative signals or radiative signals.

The one or more signals may include at least one of non-radiative heat signals or non-radiative pressure signals. The one or more signals may include at least one of radiative fluorescence signals. The radiative fluorescence signals may be radiative autofluorescence signals.

Aspects disclosed herein may provide a computer-implemented method of visualizing features in a sample. The method may include the steps of receiving signals, clustering the received one or more signals using a clustering algorithm to determine features of the sample, and determining an image based on the clustered signals. The signals may include non-radiative and radiative signals from the sample. The non-radiative signals may include heat signals and pressure signals, and the radiative signals may include fluorescence signals.

At least some of the signals may be collected by generating signals in the sample at an excitation location using an excitation beam, interrogating the sample with an interrogation beam directed toward the excitation location of the sample, and detecting a portion of the interrogation beam returning from the sample. At least some of the signals may be collected by detecting optical absorption and scattering from the sample. The optical absorption and scattering may occur from excitation and detection of the sample.

Aspects disclosed herein may provide a method of visualizing features in a sample. The method may include the steps of receiving one or more signals, clustering the received signals based on shape using a clustering algorithm to determine features of the sample, and determining an image. The shape may be based on a vector. Determining the image may include determining one or more colors used in the image, based on the clustered signals and determined features.

Aspects disclosed herein may be used with and/or receive or collect signals from any of the photoabsorption or photoacoustic remote sensing systems, methods, or signals disclosed in the following U.S. patent applications, which are incorporated herein by reference: U.S. application Ser. No. 16/847,182 filed Apr. 13, 2020 (titled Photoacoustic Remote Sensing (PARS)), U.S. application Ser. No. 17/091, 856 filed Nov. 6, 2020 (titled Non-Interferometric Photoacoustic Remote Sensing (NI-PARS)), U.S. application Ser. No. 16/814,538 filed Mar. 10, 2020 (now U.S. Pat. No. 11,022,540) (titled Camera-Based Photoacoustic Remote Sensing (C-PARS)), U.S. application Ser. No. 16/753,887 filed Apr. 6, 2020 (titled Coherence Gated Photoacoustic Remote Sensing (CG-PARS)), U.S. application Ser. No. 16/647,076 filed Mar. 13, 2020 (titled Single Source Photoacoustic Remote Sensing (SS-PARS)), U.S. application Ser. No. 16/629,371 filed Jan. 8, 2020 (titled Photoacoustic Remote Sensing (PARS), and Related Methods Of Use), U.S. application Ser. No. 17/394,919 filed Aug. 5, 2021 (titled PARS Imaging Methods), and U.S. provisional application No. 63/241,170 filed Sep. 7, 2021 (titled Non-Linear PARS Methods). Aspects disclosed herein may be used with any of the PARS systems described in the above-mentioned applications, such as: time-domain PARS or TD-PARS, total absorption PARS or TA-PARS, multi-pass PARS or MP- PARS, multi-photon excitation PARS or multi-photon PARS, thermally enhanced PARS or TE-PARS, temperature sensing PARS or TS-PARS, super-resolution PARS or SR-PARS, spectrally-enhanced PARS or SE-PARS, smart-detection PARS or SD-PARS, Camera-Based PARS or C-PARS, Non-Interferometric PARS or NI-PARS, Coherence Gated PARS or CG-PARS, Single Source PARS or SS-PARS, optical-resolution PARS or OR-PARS, dual-modality PARS combined with optical coherence tomography (PARS-OCT), and/or endoscopic PARS combined with optical coherence tomography (EPARS-OCT).

Novel photoabsorption remote sensing (PARS) signal extraction algorithms may leverage a variety of absorption-induced modulation effects including but not limited to modulation of material reflectivity, scattering, polarization, phase accumulation, nonlinear absorption, nonlinear scattering, etc. These may be used for multiplex acquisitions to separately identify and/or unmix constituent chromophores from within a sample by using a variety of excitation, detection beam, and signal enhancement beam properties including but not limited to variations in wavelength, pulse width, power, energy, coherence length, repetition rate, exposure times, etc. These properties may take on any value appropriate for the task. Common ranges may include: wavelengths (nanometers to microns), pulse widths (atto-seconds to milliseconds), powers (attowatts to watts), pulse energies (attojoules to joules), coherence lengths (nanometers to kilometers), and repetition rates (continuous-wave to gigahertz). The excitation beam may generally be implemented using shorter pulse widths (nanosecond and sub-nanosecond) intended to elicit a PARS signal impulse response, as opposed to the signal enhancement beam which may be implemented using relatively longer pulse widths (nanosecond and longer) as the signal enhancement beam may only need to elicit a thermal perturbation. For example, the pulse width of the excitation beam may be greater than 1 ns, or less than 1 ns; and the pulse width of the signal enhancement beam may be higher. In a given system architecture the excitation, detection, and signal enhancement wavelengths may be implemented using different wavelengths, pulse width, temporal delays, or polarization states as to provide a means of optical differentiation between the respective pathways.

Other novel PARS signal extraction algorithms may leverage characteristic features of collected time-domain behavior to improve signal fidelity, enhance image contrast and to recover information on the sample shape, size, and dimensions, or for performing multiplexed/functional imaging. Processing techniques may include but are not limited to lock-in amplification (both software and hardware-based implementations), machine learning methods, broad feature extraction, multidimensional decomposition and frequency content-based feature extraction and signal processing methods.

PARS may be used to unmix the composition of targets based on their absorption, temperature, polarization, frequency, phase, nonlinear absorption, constitution, velocity, fluorescence, nonlinear scattering, and scattering content. It may also be used to unmix the size, shape, feature, and dimensions of targets based on their absorption, temperature, polarization, frequency, phase, nonlinear absorption, nonlinear scattering, and scattering content. The PARS signals may be used for unmixing targets using their absorption contents, scattering contents, fluorescence, polarization contents, frequency contents, phase contents by taking advantage of different wavelengths, different pulse widths, different coherence lengths, repetition rates, lasers exposure time, laser fluence. PARS signals may be dominated by generated pressure and analyzed based on their, amplitude/intensity, frequency content, content related to polarization changes, fluorescence, second harmonic generation, and phase variations to provide information. PARS signals may be dominated by generated temperature and analyzed based on their, amplitude/intensity, fluorescence, frequency content, second harmonic generation, content related to polarization changes, and phase variations to provide information. The PARS system may be configured to capture any optical absorption induced variations in the sample. Such variations may include the entire non-radiative and radiative relaxations such as pressure signals, temperature signals, ultrasound signals, autofluorescence signals, nonlinear scattering, and nonlinear fluorescence.

A portion of interrogation, signal enhancement, excitation or autofluorescence from the sample may be collected to form images. These signals may be used to unmix the size, shape, feature, dimensions, nature, and composition of the sample. In a given architecture, any portion of the light returning from the sample such as the detection, excitation, or thermal enhancement beams may be collected. The returning light may be analyzed based on wavelength, phase, polarization, etc. to capture any absorption-induced signals including, pressure, temperature, and optical emissions. In this way, the PARS may simultaneously capture for example, scattering, autofluorescence, and polarization contrast attributed to each detection, excitation, and thermal enhancement source. Moreover, the PARS laser sources may be specifically chosen to highlight these different contrast mechanisms.

Other aspects will be apparent from the description and claims below.

BRIEF DESCRIPTION OF THE DRAWINGS

In this patent document, the word "comprising" is used in its non-limiting sense to mean that items following the word are included, but items not specifically mentioned are not excluded. A reference to an element by the indefinite article "a" does not require that there be one and only one of the elements.

The scope of the following claims should not be limited by the preferred embodiments set forth in the examples above and in the drawings but should be given the broadest interpretation consistent with the description as a whole.

FIG. 19 compares Multi-Photon PARS with normal PARS.

FIGS. 21A and 21B show principal components of a time-domain TD-PARS signal and a synthesized stain based on the principal components.

FIG. 26 shows an exemplary clustering algorithm to analyze the TD-PARS signals and determine an image.

FIG. 27 shows a method of determining an image using the clustering algorithm.

FIG. 37 shows a direct construction of a colorized image.

DETAILED DESCRIPTION

Figure 2:
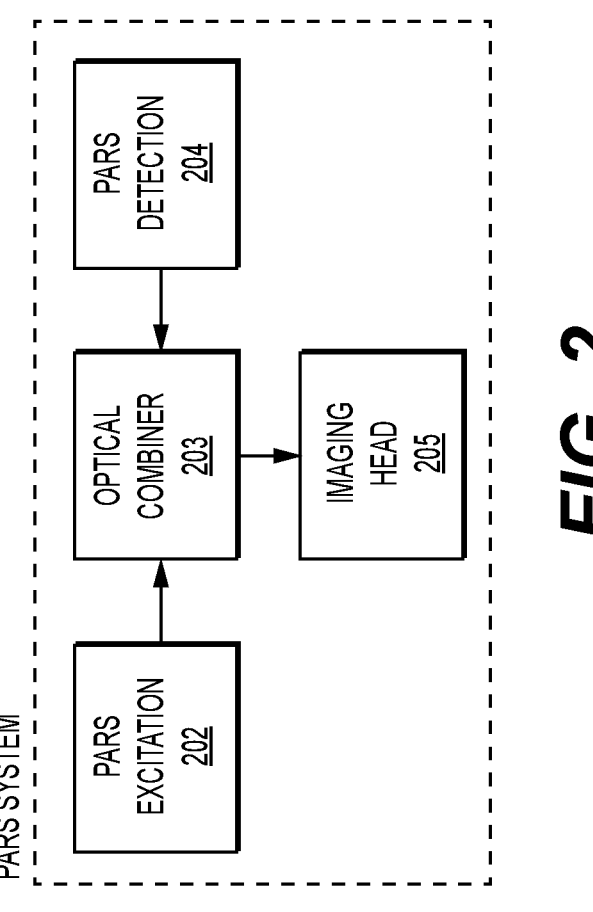
FIG. 2 shows an overview of a PARS system with PARS excitation and PARS detection.

Reference will now be made in detail to examples of the present disclosure, which are illustrated in the accompanying drawings. Wherever possible, the same reference numbers will be used throughout the drawings to refer to the same or like parts. In the discussion that follows, relative terms such as "about," "substantially," "approximately," etc. are used to indicate a possible variation in a stated numeric value.

A recently reported photoacoustic technology known as photoacoustic remote sensing (PARS) microscopy (US 2016/0113507, and US 2017/0215738) has solved many of these sensitivity issues through a novel detection mechanism. Rather than detecting acoustic pressures at an outer surface once they have propagated away from their source, PARS enables direct detection of excited photoacoustic regions. This is accomplished by monitoring changes in material optical properties that coincide with the photoacoustic excitation. These changes then encode various salient material properties such as the optical absorption, physical target dimensions, and constituent chromophores to name a few.

Since PARS devices may utilize only two optical beams which may be in a confocal arrangement, spatial resolution of the imaging technique may be defined as excitation-defined (ED) or interrogation-defined (ID) depending on which of the beams provide a tighter focus at the sample. This aspect also may facilitate imaging deeper targets, beyond the limits of optical resolution devices. This may be accomplished by leveraging a deeply-penetrating (long transport mean-free-path) detection wavelength such as a short-wave infrared (like 1310 nm, 1700 nm or 10 um) which may provide spatial resolution to a depth superior to that provided by a given excitation (such as 532 nm or 266 nm) within highly scattering media such as biological tissues. If more than two beams are used such that a system consists of more than two foci at the sample, then obvious extensions of these components would be expected. For example, if an additional beam which amplifies the signal within its focal region is added, it may also contribute towards defining the expected resolution of the system.

Intensity-modulated PARS signals hold dependence on not only optical absorption and incident excitation fluence, but also on detection laser wavelength, fluence and the temperature of the sample. PARS signals may also arise from other effects such as scatterer position modulation and surface oscillations. A similar analog may exist for PARS devices which take advantage of other modulating optical properties such as intensity, polarization, frequency, phase, fluorescence, non-linear scattering, non-linear absorption, etc. As material properties are dependent on ambient temperature, there is a corresponding temperature dependence in the PARS signal. At some intensity levels, additional saturation effects may also be leveraged.

The above mechanisms point to significant sources of scattering position or scattering cross-section modulation that could be readily measurable when the probe beam is focused to sense the confined excitation volume. However, these large local signals are not the only potential source of PARS signal. Acoustic signals propagating to the surface of the sample could also result in changes in PARS signal. These acoustic signals can generate surface oscillation as well which result in phase modulation of the PARS signals.

These generated signals may be intentionally controlled or effected by secondary physical effects such as vibration, temperature, stress, surface roughness, mechanical bending among others. For example, temperature may be introduced to the sample, which may augment the generated PARS signals as compared to those which would be generated without having introduced this additional temperature. Another example may involve introducing mechanical stress to the sample (such as bending) which may in turn effect the material properties of the sample (e.g., density or local optical properties such as birefringence, refractive index, absorption coefficient, scattering behavior) and thereby perturbing the generated PARS signals as compared to those which would have been generated without having introduced this mechanical stress. Additional contrast agents may be added to the sample to boost the generated PARS signals, this includes but is not limited to dyes, proteins, specially designed cells, liquids and optical agents or windows. The target may be altered optically to provide optimized results.

Some techniques may simply monitor intensity back reflection and may extract the amplitude of these time-domain signals. However, additional information may be extracted from the time-varying aspects of the signals. For example, some of the scattering, polarization, frequency, and phase content with a PARS signal may be attributed to the size, shape, features, and dimensions of the region which generated that signal. This may encode unique/orthogonal additional information with utility towards improving final image fidelity, classifying sample regions, sizing constituent chromophores, and classifying constituent chromophores to name a few. As such techniques may generate independent datasets for the same interrogated region they may be combined or compared with each other. For example, frequency information may describe the microscopic structures within the sample, this may be combined with conventional PARS which uses scattering modulation to highlight regions which are both absorbing and of a specific size.

Figure 1:
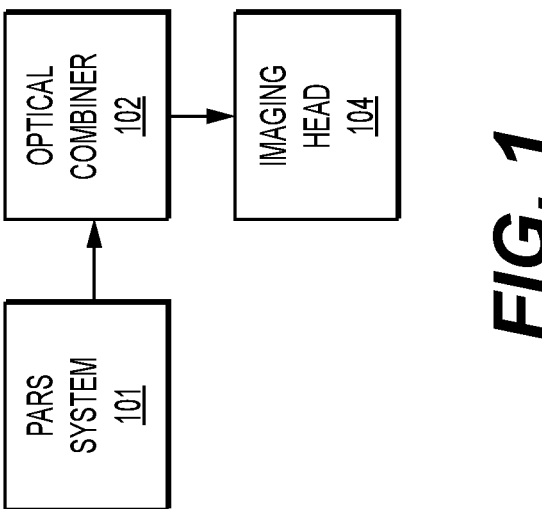
FIG. 1 shows an overview of a PARS system.

Referring to FIG. 1, photoacoustic remote sensing (PARS) microscopy is an all-optical non-contact optical absorption microscopy technique. PARS may use a co-focused excitation and detection laser pair to generate and detect optical absorption contrast in a variety of specimens. In PARS, the excitation laser may include a pulsed excitation laser, which may be used to deposit optical energy into a sample. When the light is absorbed by a chromophore, the photon energy is captured by the specimen. The absorbed energy may then be dissipated through either optical radiation (radiative) or non-radiative relaxation. During non-radiative relaxation, absorbed optical energy is converted into heat. In certain cases, the generation of heat may cause thermoelastic expansion resulting in photoacoustic pressures. During radiative relaxation, absorbed optical energy is released through the emission of photons. Generally, emitted photons exhibit a different energy level compared to the absorbed photons.

Changes in the local temperature and pressure result in nano-second scale perturbations in a sample optical and material properties. The detection laser, co-focused with the excitation spot, may capture the absorption-induced perturbations in the optical properties as scattering intensity modulations. By measuring the perturbations in the detection laser scattering, PARS can then measure the non-radiative absorption contrast of different biomolecules. Concurrently, by capturing the unperturbed back reflection of the detection, and the back-reflected excitation energy the PARS may capture the optical scattering contrast attributed to the excitation and detection sources, respectively.

FIG. 1 shows a high-level diagram of a photoabsorption remote sensing (PARS) system. This consists of a PARS system (101), an optical combiner (102), and an imaging head (104). The PARS system may further include other systems (e.g., signal enhancement system), and the optical combiner may combine the beams from the PARS system (101) and these other systems.

FIG. 2 shows a high-level diagram with the PARS Excitation (202), PARS Detection (204) and Optical Combiner (203) delineated. These could be combined with other systems (e.g., signal enhancement system) and Imaging Head (205).

Figure 3:
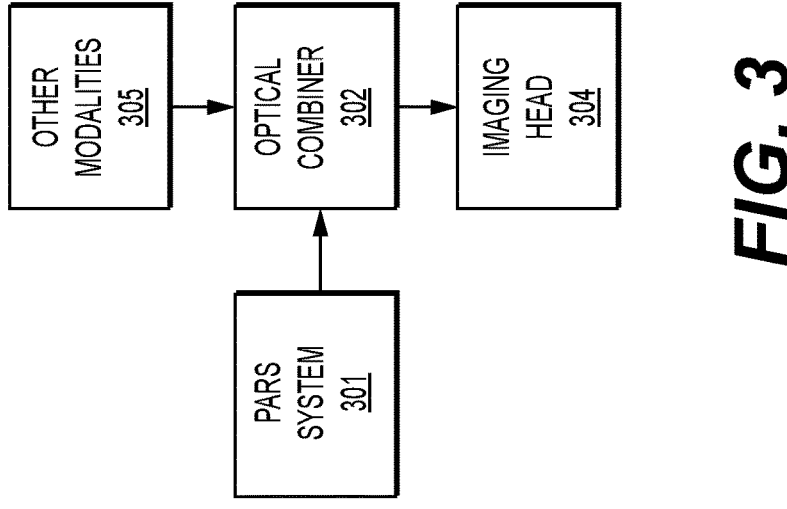
FIG. 3 shows an implementation of PARS being combined with other modalities.

FIG. 3 shows a high-level embodiment of a PARS system combined with other modalities (305). This consists of a PARS system (301), optical combiner (302), and an imaging head (304). These can be combined with a variety of other modalities (305) such as bright-field microscopy, scanning laser ophthalmoscopy, ultrasound imaging, stimulated Raman microscopy, fluorescence microscopy, two-photon and confocal fluorescence microscopy, Coherent-Anti-Raman-Stokes microscopy, Raman microscopy, other PARS, photoacoustic and ultrasound systems, among others.

Figure 4:
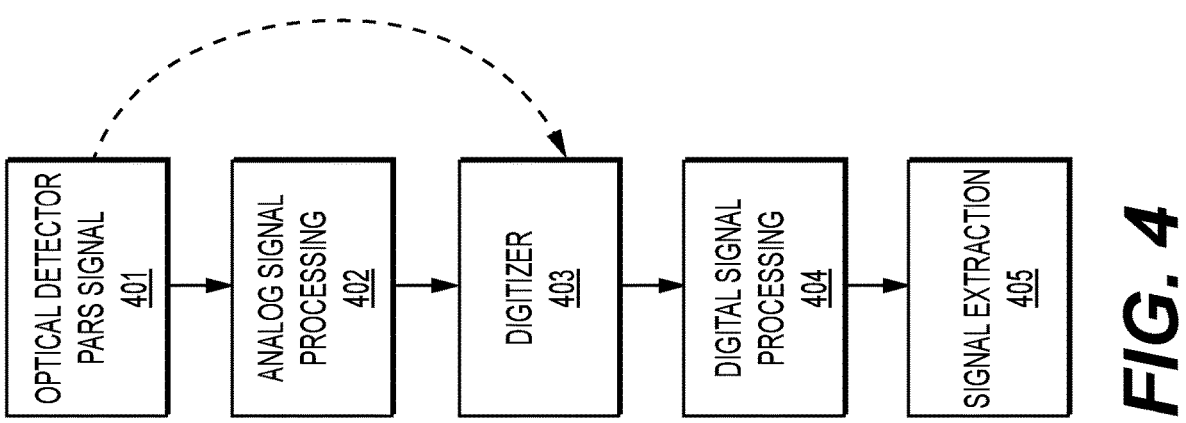
FIG. 4 shows a signal processing pathway of PARS signals.

FIG. 4 shows a signal processing pathway. This consists of an optical detector (401), a signal processing unit (402), a digitizer (403), a digital signal processing unit (404) and a signal extraction unit (405).

TA-PARS

When a sample absorbs light, there is a limited number of interactions which may happen. The absorbed energy is converted to temperature and pressure, or to light of a different wavelength. While the temperature and pressure signals are captured by a PARS detection beam, the light emissions may be detected by a total absorption (TA) PARS system, which may be sensitive to radiative relaxation. In this way, all or nearly all absorption of light by the tissues (whether in the form of non-radiative signals like generated pressure, generated temperature, radiative relaxation such as fluorescence, multiphoton fluorescence, or stimulated Raman scattering), and/or scattering signals such as local scattering signals may be captured by the PARS.

Figure 5:
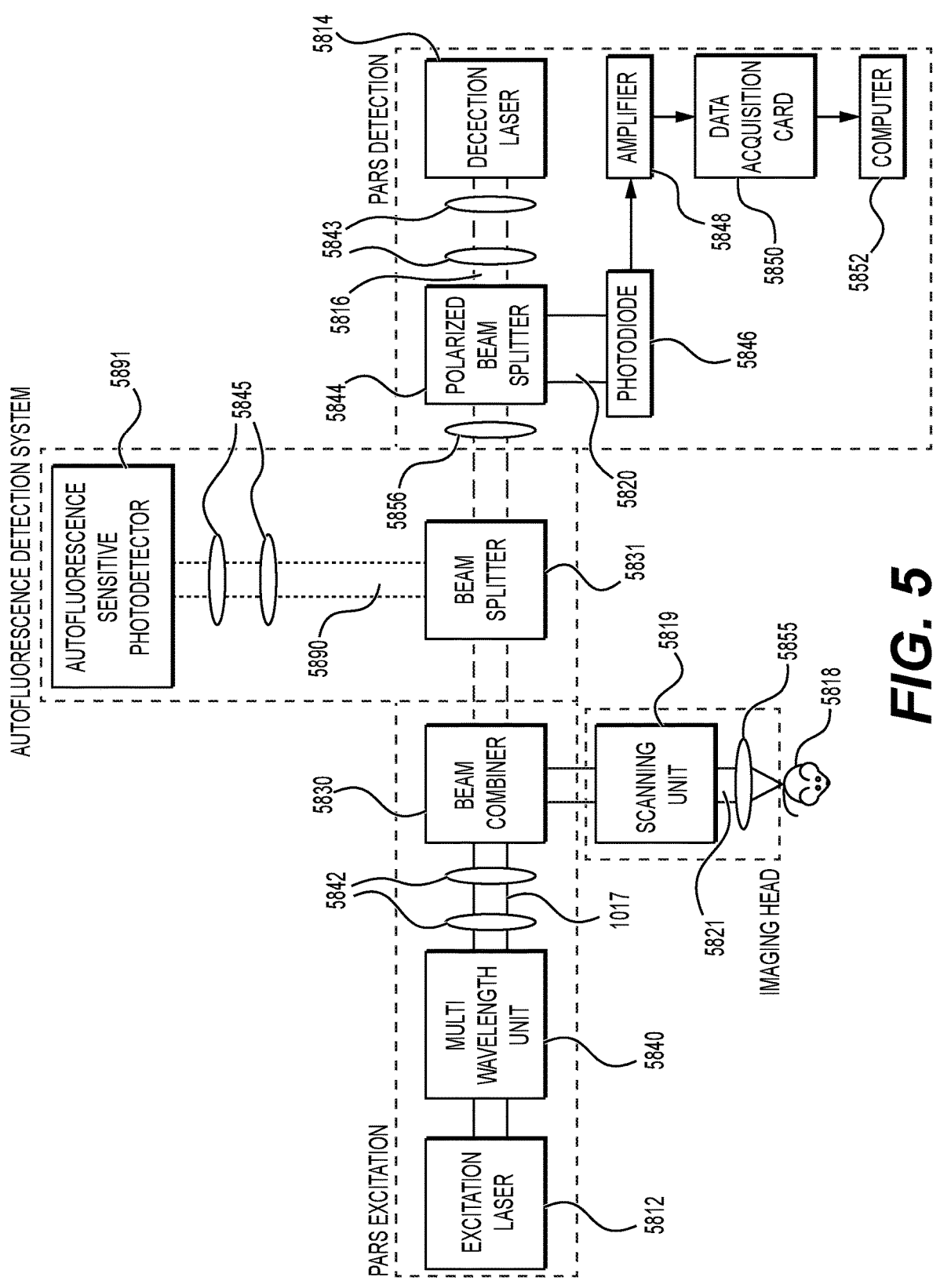
FIG. 5 shows exemplary architecture for total absorption (TA) PARS, where an autofluorescence detection system is used as an example.

FIG. 5 shows exemplary architecture for a radiative relaxation sensitive PARS. As an example, the radiative relaxation may be fluorescent or autofluorescent, but aspects disclosed herein are not limited. For example, the radiative relaxation may include Raman scattering, fluorescence, autofluorescence, multiphoton fluorescence, etc. For convenience of description, an autofluorescence sensitive TA-PARS system will be described as an example with reference to FIG. 5. A multi-wavelength fiber excitation laser (5812) is used to generate PARS signals. An excitation beam (5817) passes through a multi-wavelength unit (5840) and a lens system (5842) to adjust its focus on the sample (5818). The optical subsystem used to adjust the focus may be constructed by components known to those skilled in the art including but not limited to beam expanders, adjustable beam expanders, adjustable collimators, adjustable reflective expanders, telescope systems, etc.

The signal signatures are interrogated using either a short or long-coherence length probe beam (5816) from a detection laser (5814) that is co-focused and co-aligned with the excitation spots on the sample (5818). The interrogation/probe beam (5816) passes through a lens system (5843), polarizing beam splitter (5844) and quarter wave plate (5856) to guide the reflected light (5820) from the sample (5818) to the photodiode (5846). However, this architecture is not limited to including a polarizing beam splitter (5844) and quarter wave plate (5856). The aforementioned components may be substituted for fiber-based, equivalent components, e.g., a circulator, coupler, Faraday rotator, electro-optic modulator, WDM, and/or double-clad fiber, that are non-reciprocal elements. Such elements may receive light from a first path, but then redirect said light to a second path.

The interrogation beam (5816) is combined with the excitation beam using a beam combiner (5830). The combined beam (5821) is scanned by a scanning unit (5819). This passes through an objective lens (5855) and is focused onto the sample (5818).

The reflected beam (5820) returns along the same path. The reflected beam is filtered with a beam combiner/splitter (5831) to separate the detection beam (5816) from any autofluorescence light returned from the sample. The autofluorescence light (5890) passes through a lens system (5845) to adjust its focus onto the autofluorescence sensitive photodetector (5891). The isolated detection beam (5820) is transmitted through the beam splitter (5831) towards the signal collection/analysis pathway. Here the returned detection light is redirected by the polarized beam splitter (5844). The detection pathway consists of a photodiode (5846), amplifier (5858), fast data acquisition card (5850) and computer (5852). The autofluorescence sensitive photodetector may be any such device including a camera, photodiode, photodiode array etc. The autofluorescence detection pathway may include more beam splitters and photodetectors to further isolate and detect specific wavelengths of light.

Figure 6:
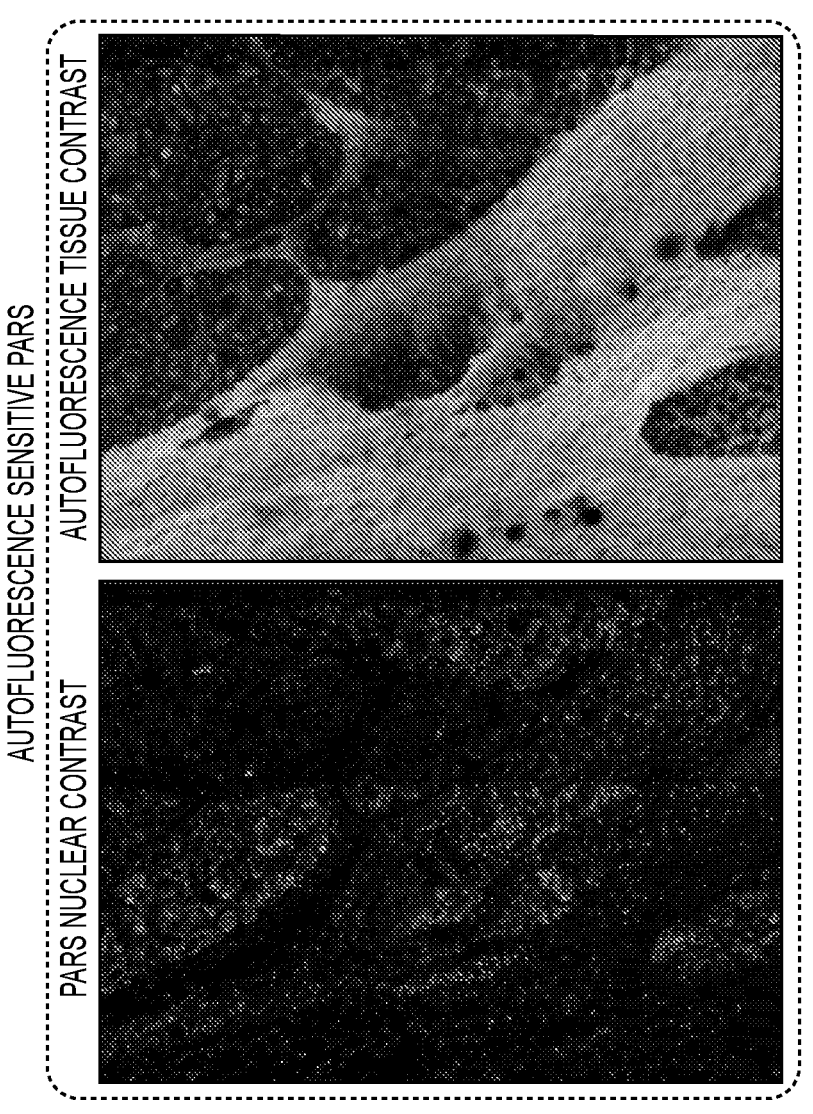
FIG. 6 shows a visualization produced by the autofluorescence sensitive total absorption PARS (TA-PARS) architecture.

FIG. 6 shows exemplary visualizations which may potentially be provided by autofluorescence sensitive TA-PARS. Any portion of the light returning from the sample, excluding the detection beam, may be collected, and analyzed based on wavelength. By isolating specific wavelengths of light emissions from the sample, we may visualize specific molecules of interest. For example, we may apply the autofluorescence sensitive PARS to imaging tissues. Here, we selected the PARS excitation to capture absorption contrast of nuclei. In this case, we use a UV excitation to generate pressure and temperature signals attributed to nuclei in tissues. Concurrently, we capture the autofluorescence contrast generated by the PARS excitation. In this case, the non-nuclear regions of the tissues, are highly fluorescent. In this way, we can provide visualizations of nuclear and non-nuclear structures in tissues simultaneously. Moreover, the resulting visualizations may require only a single (or only one or exactly one) excitation wavelength to capture. As previously described, this method may be used with other radiative relaxation sensitive PARS, and radiative relaxation other than autofluorescence may be generated and captured.

For example, the PARS radiative signal could be implemented into a PARS absorption spectrometer to accurately measure all absorption of light by a sample. Moreover, we may use the radiative relaxation (e.g., autofluorescence in FIG. 5) sensitive PARS to measure the proportion of absorbed energy which is converted to heat and pressure or light respectively. This may enable sensitive quantum efficiency measurements in a broad range of biological and non-biological samples.

Figure 7:
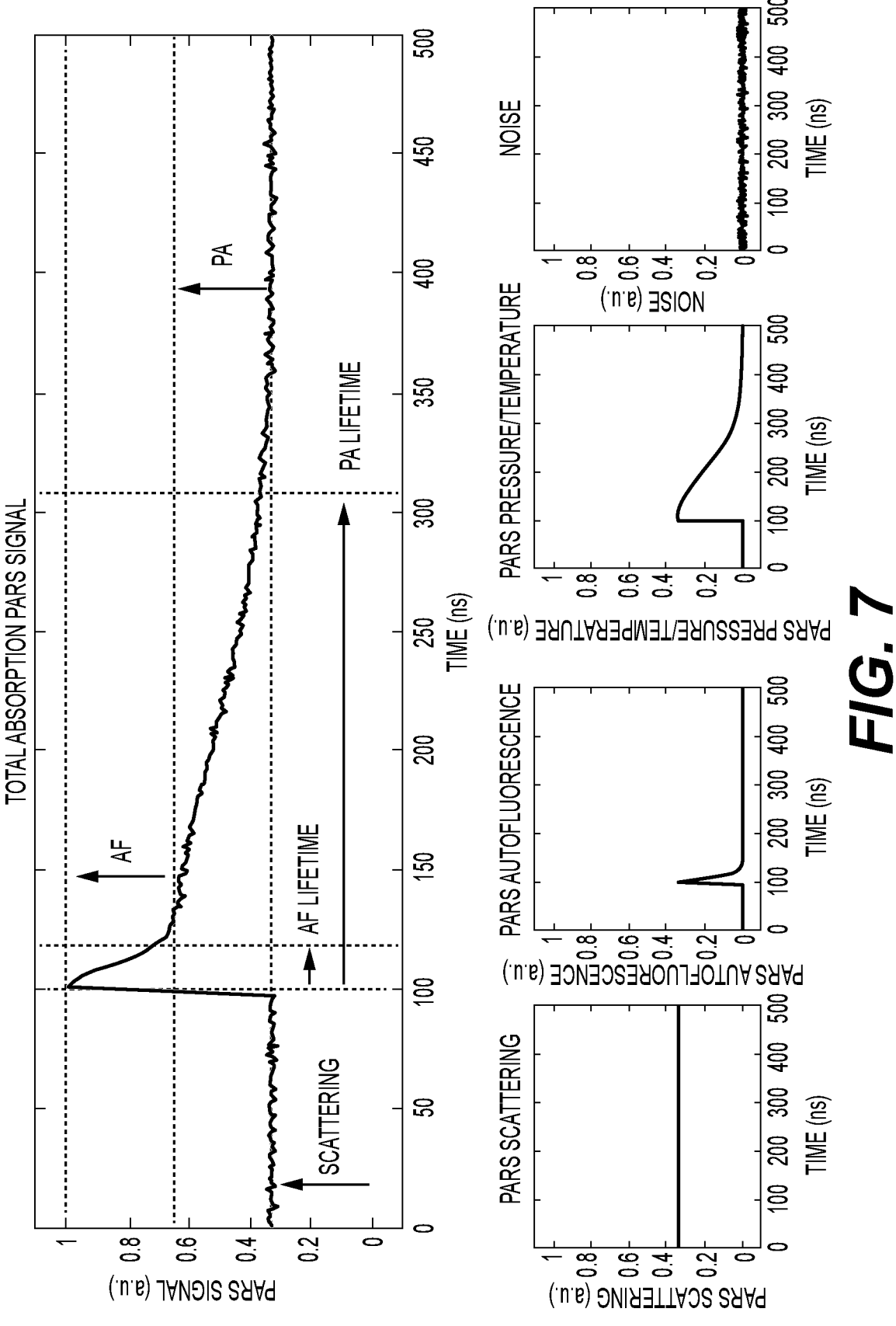
FIG. 7 shows an exemplary signal evolution of a TA-PARS signal.

The TA-PARS signal may also be collected on a single (only one or exactly one) detector as highlighted in FIG. 7. Given that the salient components of the TA-PARS signal may appear distinct from each other, a single detector may appropriately characterize these components. For example, the initial signal level (Scattering) may be indicative of the un-perturbed intensity reflectivity of the detection beam from the sample at the interrogation location encoding the scatter intensity. Then, following excitation by the excitation pulse (at 100 ns in FIG. 7), PARS excitation signals related to non-radiative relaxation (e.g., thermal, temperature), and radiative relaxation (e.g., fluorescence or autofluorescence) may be observed as unique overlapping signals (labeled PA and AF in the diagram).

If these excited signals are measurably unique (e.g., in amplitude or magnitude and/or evolution time) from each other, they may be decomposed from the combined signal to extract these magnitudes along with their characteristic lifetimes. This wealth of information may be useful in improving available contrast, providing additional multiplexing capabilities, and providing characteristic molecular signatures of constituent chromophores. In addition, such an approach may provide pragmatic benefits in that only a single detector and a single (only one or exactly one) detection path may be required, drastically reducing physical hardware complexity and cost. Capturing signals over time are discussed in more detail in the section covering TD-PARS.

Figure 8:
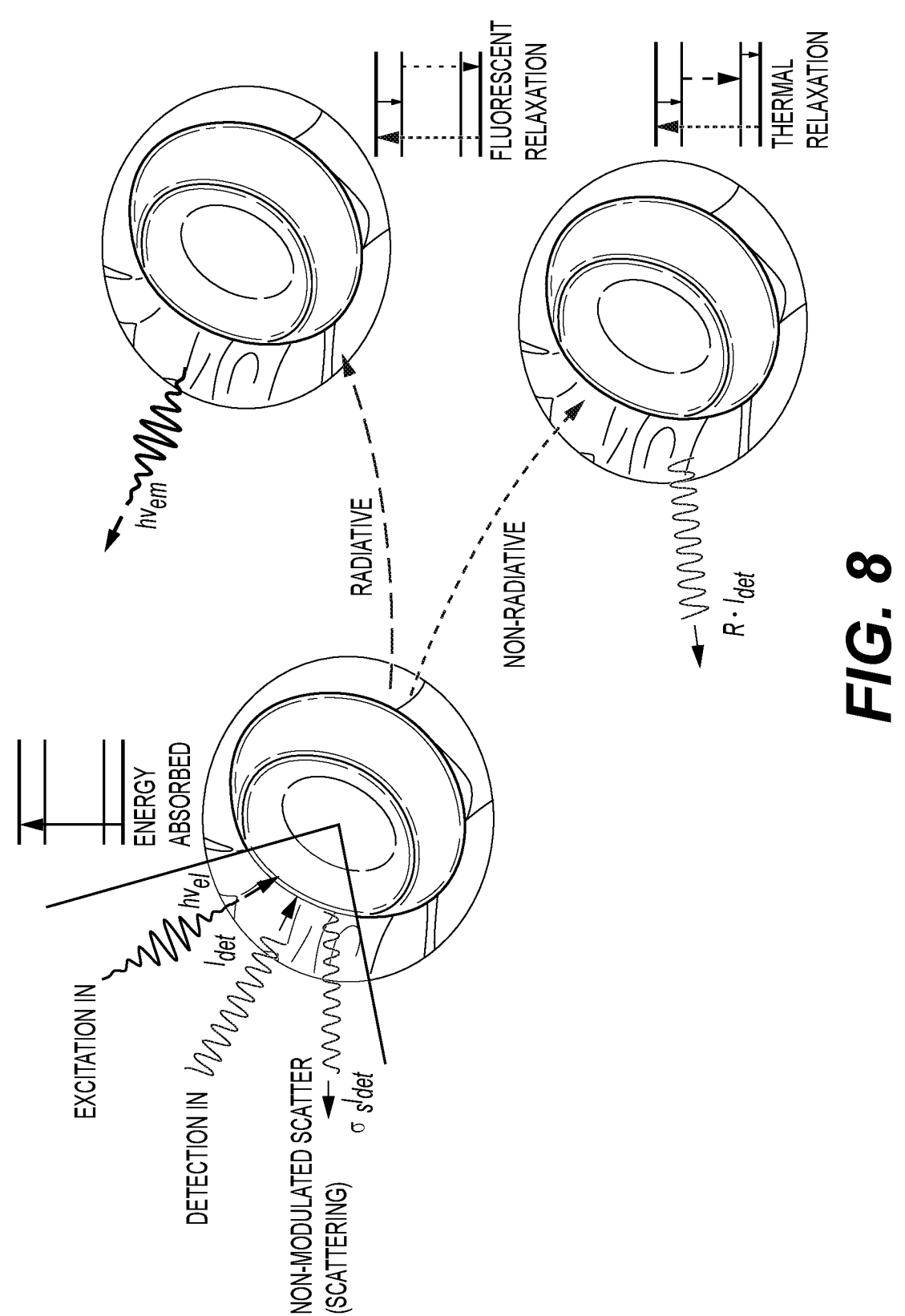
FIG. 8 shows an example of radiative and non-radiative signals.

Referring to FIG. 8, any given PARS excitation event always generates some fraction of radiative and non-radiative relaxation. TA-PARS facilitates the capture of a chromophores total-absorption profile. The thermal and pressure perturbations may generate corresponding modulations in the local optical properties. The TA-PARS microscope may capture a chromophores' scattering, and total absorption (radiative and non-radiative relaxation) visualizations in a single (only one or exactly one) excitation event. The non-radiative relaxation leads to heat and pressure induced modulations, which in turn cause back-reflected intensity variations in the detection beam. PARS signals are denoted as some change in reflectivity multiplied by the incident detection ($RI_{det}$). The radiative absorption pathway captures optical emissions attributed to radiative relaxation such as stimulated Raman scattering, fluorescence, multiphoton fluorescence, etc. Emissions are denoted as some wavelength and energy optical emission ($hv_{em}$). The local scattering contrast is captured as the unmodulated backscatter (pre-excitation pulse) of the detection beam. The scattering contrast is denoted as the unperturbed scattering profile multiplied by the incident detection power ($\sigma_s I_{det}$).

In TA-PARS, the non-radiative relaxation-induced modulations are detected at the excited location by the probe beam. The PARS may then visualize any heat or photoacoustic pressures which cause modulation in the local optical properties. Concurrently, the TA-PARS leverages an additional detection pathway to capture non-specific optical emissions regardless of properties such as wavelength, frequency, polarization from the sample (excluding the excitation and detection). These emissions may then be attributed to any radiative relaxation effects such as stimulated Raman scattering, fluorescence, and multiphoton fluorescence.

Using this detection pathway may provide enhanced sensitivity to any range of chromophores. Unlike traditional modalities which independently capture some of the radiative or non-radiative absorption, in TA-PARS, the contrast may not be bound by efficiency factors such as the photothermal conversion efficiency or fluorescence quantum yield. By capturing the non-radiative and radiative absorption contrast in addition to the scattering of the excitation and detection, the TA-PARS may capture all or nearly all the optical properties of a chromophore such as the absorption coefficient, scattering coefficient, quantum efficiency, nonlinear interaction coefficients, providing simultaneous sensitivity to most chromophores.

Quantum Efficiency Ratio (QER) and Label-Free H&E Visualizations

Capturing both radiative and non-radiative absorption fractions may also yield additional information. TA-PARS may yield an absorption metric proposed as the quantum efficiency ratio (QER), which visualizes a biomolecules proportional radiative and non-radiative absorption response. The TA-PARS may provide label-free visualization of a range of biomolecules enabling convincing analogues to traditional histochemical staining of tissues, effectively providing label-free Hematoxylin and Eosin (H&E)-like visualizations.

QER may be defined as a ratio of radiative PARS signals ($P_r$) to non-radiative PARS ($P_{nr}$), such as: ($QER=P_r/P_{nr}$; $QER=(P_r-P_{nr})/(P_r+P_{nr})$). This ratio will be unique to any given chromophore. For example, a biomolecule like collagen will exhibit high radiative contrast, and low nonradiative contrast providing a high QER. Conversely, DNA will exhibit low radiative contrast, and high non-radiative contrast providing a high QER. Calculating the QER in addition from the radiative and non-radiative absorption may allow for properties such as the chromophore composition, density, and quantity to be extracted in a single (only one or exactly one) event. This may also allow for single-shot functional imaging.

For example, a picosecond scale pulsed excitation laser may elicit radiative and nonradiative (thermal and pressure) perturbations in a sample. The thermal and pressure perturbations generate corresponding modulations in the local optical properties. A secondary probe beam co-focused with the excitation may capture the non-radiative absorption induced modulations to the local optical properties as changes in backscattering intensity.

These backscatter modulations may be directly correlated to the local non-radiative absorption contrast. By the nature of the probe architecture, the unperturbed backscatter (pre-excitation event) also captures the scattering contrast as seen by the probe beam. Unlike traditional photoacoustic methods, rather than relying on the pressure waves to propagate through the sample before detection via acoustic transducer, the TA-PARS probe may instantaneously detect the induced modulations at the excited location. Therefore, TA-PARS offers non-contact operation, facilitating imaging of delicate, and sensitive samples, which would otherwise be impractical to image with traditional contact-based PAM methods.

Since TA-PARS may rely only on the generation of heat and subsequently pressure to provide contrast, the absorption mechanism is non-specific, and highly sensitive to small changes in relative absorption. This allows any variety of absorption mechanisms such as vibrational absorption, stimulated Raman absorption, and electronic absorption to be detected with PARS. Previously, PARS has demonstrated label-free non-radiative absorption contrast of hemoglobin, DNA, RNA, lipids, and cytochromes, in specimens such as chicken embryo models, resected tissue specimens, and live murine models. In TA-PARS, a unique secondary detection pathway captures radiative relaxation contrast, in addition to the non-radiative absorption. The radiative absorption pathway was designed to broadly collect all-optical emissions at any wavelength of light, excluding the excitation and detection. As a result, the radiative detection pathway captures non-specific optical emissions from the sample regardless of properties such as wavelength, frequency, polarization.

Figure 9:
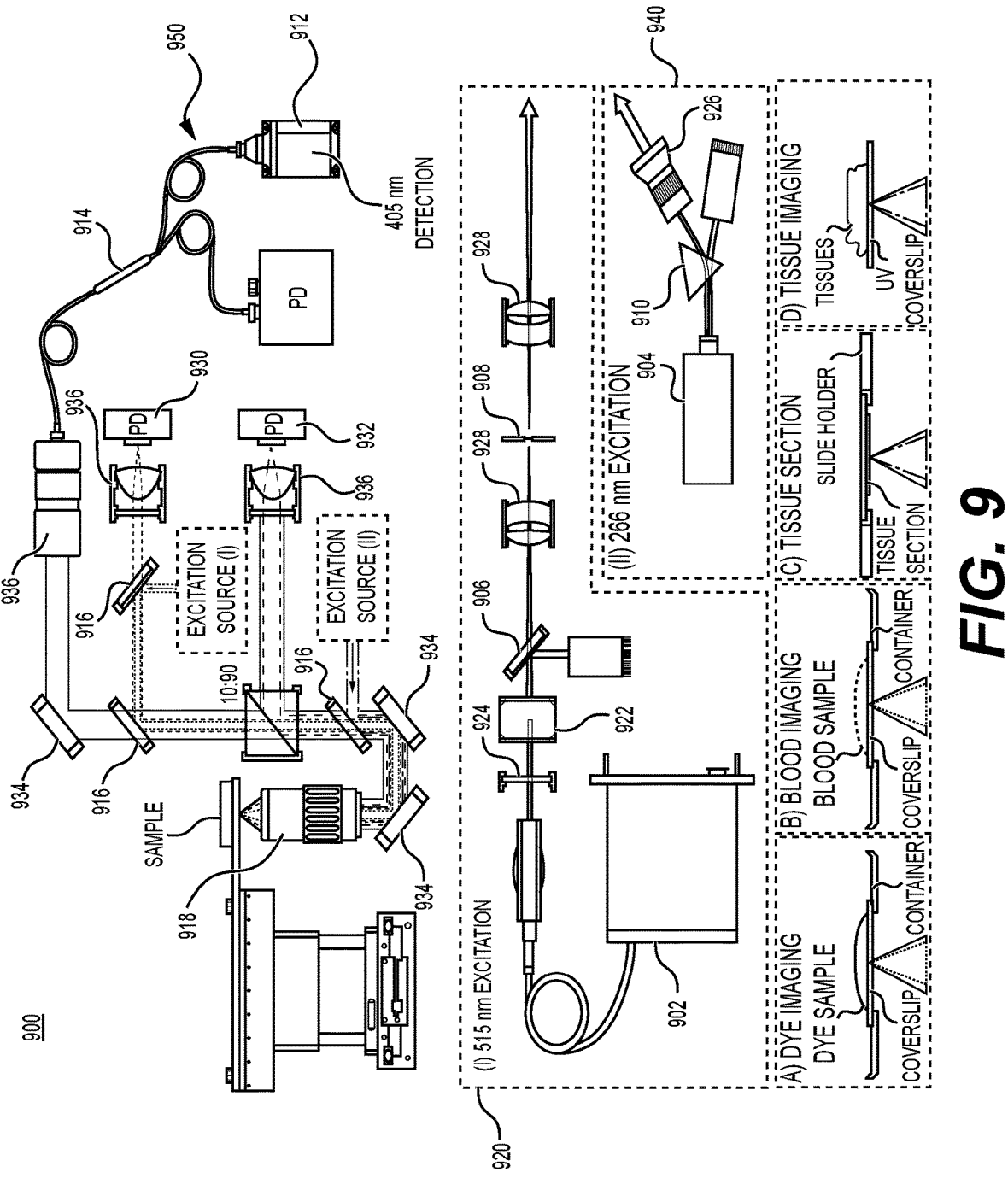
FIG. 9 shows exemplary architecture using two excitation sources, one detection source, and a plurality of photodiodes.

Referring to FIG. 9, to improve the sensitivity of the TA-PARS and facilitate the detection of radiative absorption contrast, a TA-PARS 900 may include excitation at first and second excitation wavelengths that are different from each other (e.g., 266 nm and 515 nm excitation), providing sensitivity to DNA, heme proteins, NADPH, collagen, elastin, amino acids, and a variety of fluorescent dyes. The TA-PARS may include a specific optical pathway with dichroic filters and avalanche photodiode, to isolate and detect the radiative absorption contrast. As exemplified in FIG. 9, the TA-PARS system may include excitation at the first excitation wavelength (e.g., visible light such as 515 nm visible excitation) from a first excitation source 920 and excitation at the second excitation wavelength (e.g., UV light such as 266 nm UV excitation) from a second excitation source 940. The first excitation source 920 may include a first excitation laser 902, such as a 50 kHz to 2.7 MHz 2 ps pulsed 1030 nm fiber laser (e.g., YLPP-1-150-v-30, IPG Photonics), but aspects disclosed herein are not limited. The second harmonic may be generated with a lithium triborate crystal or LBO 922. The first (e.g., 515 nm) harmonic may be separated via a dichroic mirror 906, then spatial filtered with a pinhole 908 prior to use in the imaging system. The first excitation source 902 may include one or more lenses or plates, such as a half-wave plate or HWP 924 provided between LBO 922 and the first excitation laser 902, a filtering lens, and/or a lens assembly 928. The pinhole 908 may be provided between, as an example, two lenses or lens assemblies 928.

The second excitation source 940 may include a second excitation laser 904, such as a 50 kHz 400 ps pulsed diode laser (e.g., Wedge XF 266, RPMC), but aspects disclosed herein are not limited. Output from the second excitation laser 904 may be separated from residual excitation (e.g., 532 nm excitation) using a prism 910, then expanded (e.g., using a variable beam expander or VBE 926) prior to use in the imaging system.

The TA-PARS system may include a detection system 950 shared between the first and second excitation sources 920 and 940. As exemplified in FIG. 9, the TA-PARS detection system 950 may include a probe beam 912, which may include a 405 nm laser diode such as a 405 nm OBIS-LS laser (OBIS LS 405, Coherent). Here, the detection may be fiber coupled through a circulator 914 into the system, where it may be combined with the excitations via one or more dichroic mirrors 916 and/or guided via mirrors 934. The combined excitation and detection may be co-focused onto the sample using a lens 918, such as a 0.42 NA UV objective lens. Back-reflected detection from the sample may return to the circulator 914 by the same path as forward propagation. The back-reflected detection contains the PARS non-radiative absorption contrast as nanosecond scale intensity modulations which may be captured with a photodiode. The detection system 950 may also include a collimator and/or collimating assembly 936 to collimate the detection light.

This probe wavelength provides improved scattering resolution, which improves the confocal overlap between the PARS excitation and detection spots on the sample. Combined with a circulator-based probe beam pathway and avalanche photodetector, the TA-PARS provides improved sensitivity compared to previous implementations. The visible wavelength probe also provides improved compatibility between the visible and UV excitation wavelengths.

Radiative relaxation from each of the first and second excitations (266 nm and 515 nm excitation) may be independently captured with different (or first and second) photodiodes 930 and 932. The radiative relaxation induced from the first excitation (515 nm induced radiative relaxation) may be isolated with dichroic mirrors 916, then captured using the first photodiode 930. The radiative relaxation induced from the second excitation (266 nm induced radiative relaxation) may be isolated by redirecting some portion (e.g., 1%-50%) of the total light intensity returned from the sample towards a photodetector and/or second photodiode 932. This light may then be spectrally filtered (e.g., via lens assemblies 936) to remove residual excitation and detection prior to measurement.

To form an image, mechanical stages may be used to scan a sample over the objective lens. The excitation sources 920 and 940 may be continuously pulsed (e.g., at 50 kHz), while the stage velocity may be regulated to achieve a desired pixel size (spacing between interrogation events). Each time the excitation laser 902 and/or 904 is pulsed, a collection event may be triggered. During a collection event, a few hundred nanosecond segment may be collected from 4 input signals using a high-speed digitizer (e.g., RZE-004-200, Gage Applied). These signals may include the laser input reference measurements (excitation and detection), PARS scattering signal, the PARS non-radiative relaxation signal, the PARS radiative relaxation signal, and a positional signal from the stages. The time resolved scattering, absorption, and position signals, may then be compressed down to single characteristic features. This serves to substantially reduce the volume of data capture during a collection.

To reconstruct the absorption and scattering images, the raw data may be fitted to a Cartesian grid based on the location signal at each interrogation. Raw images may then be gaussian filtered and rescaled based on histogram distribution prior to visualization.

TA-PARS visualization fidelity is assessed through one-to-one comparison against traditional H&E-stained images. The TA-PARS total-absorption and QER contrast mechanisms are also validated in a series of dye and tissue samples. Results show high correlation between radiative relaxation characteristics and TA-PARS-measured QER in a variety of fluorescent dyes, and tissues. These QER visualizations are used to extract regions of specific biomolecules such as collagen, elastin, and nuclei in tissue samples. This enables realization of a broadly applicable high resolution absorption contrast microscope system. The TA-PARS may provide unprecedented label-free contrast in any variety of biological specimens, providing otherwise inaccessible visualizations.

Figure 10:
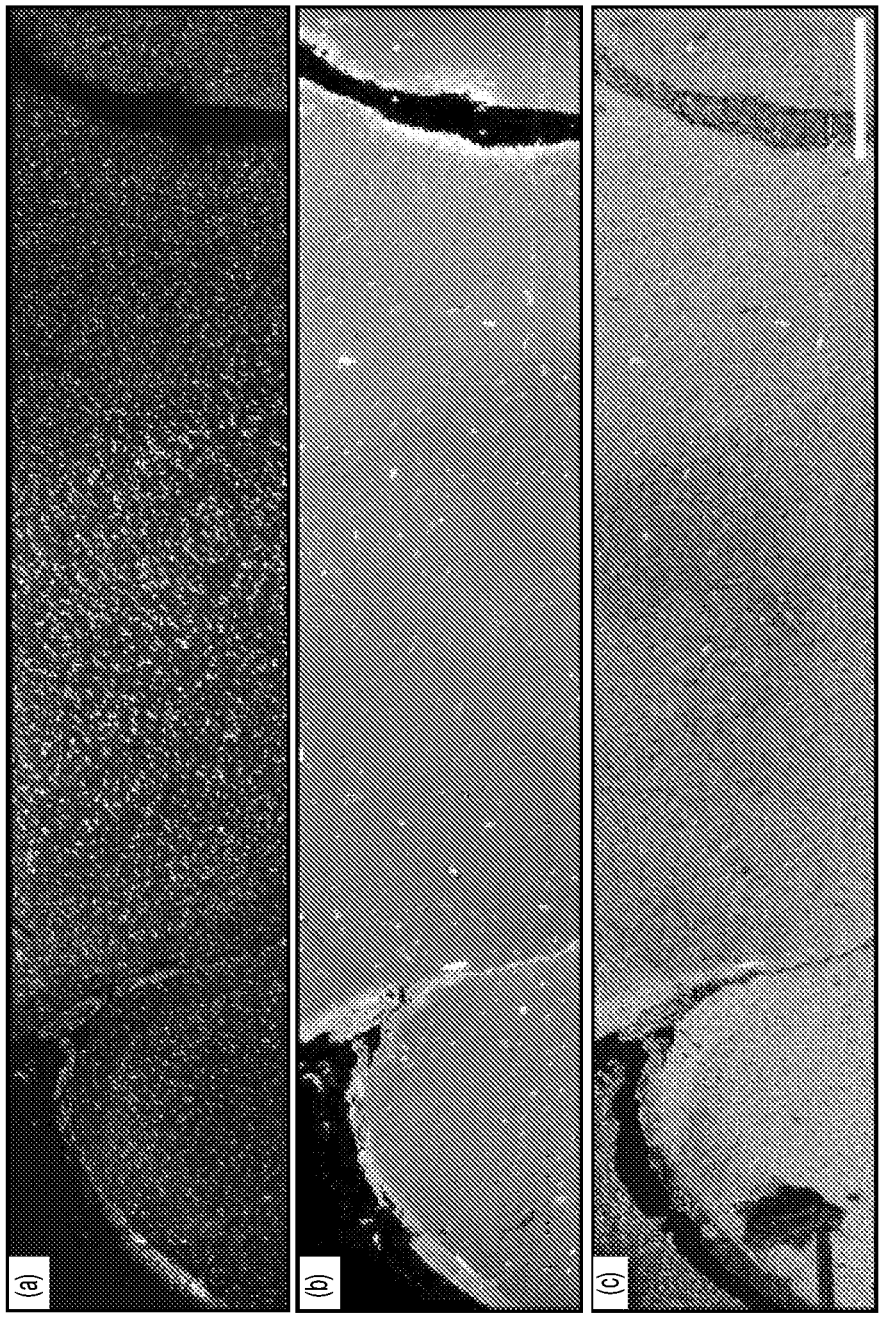
FIG. 10 shows a comparison of non-radiative absorption (view (a)), radiative absorption (view (b)), and scattering (view (c)) provided by a TA-PARS system.

FIG. 10 shows a comparison of three different contrasts (non-radiative absorption in view (a), radiative absorption in view (b), and scattering in view (c)) provided by a TA-PARS system using 266 nm excitation in thin sections of formalin fixed paraffin embedded (FFPE) human brain tissues. The non-radiative relaxation signals were captured based on nanosecond scale pressure- and temperature-induced modulations in the collected backscattered 405 nm detection beam from the sample. The radiative absorption contrast was captured as optical emissions from the sample, excluding the excitation and detection wavelengths which were blocked by optical filters. Concurrently, the unperturbed backscatter of the 405 nm probe captures the local optical scattering from the sample. With this contrast, most of the salient tissue structures were captured. The non-radiative absorption contrast highlights predominately nuclear structures, while the radiative contrast captures extranuclear features. The optical scattering contrast captures the morphology of the thin tissue section. In resected tissues this scattering contrast becomes less applicable, and hence was not explored in other samples.

Figure 11:
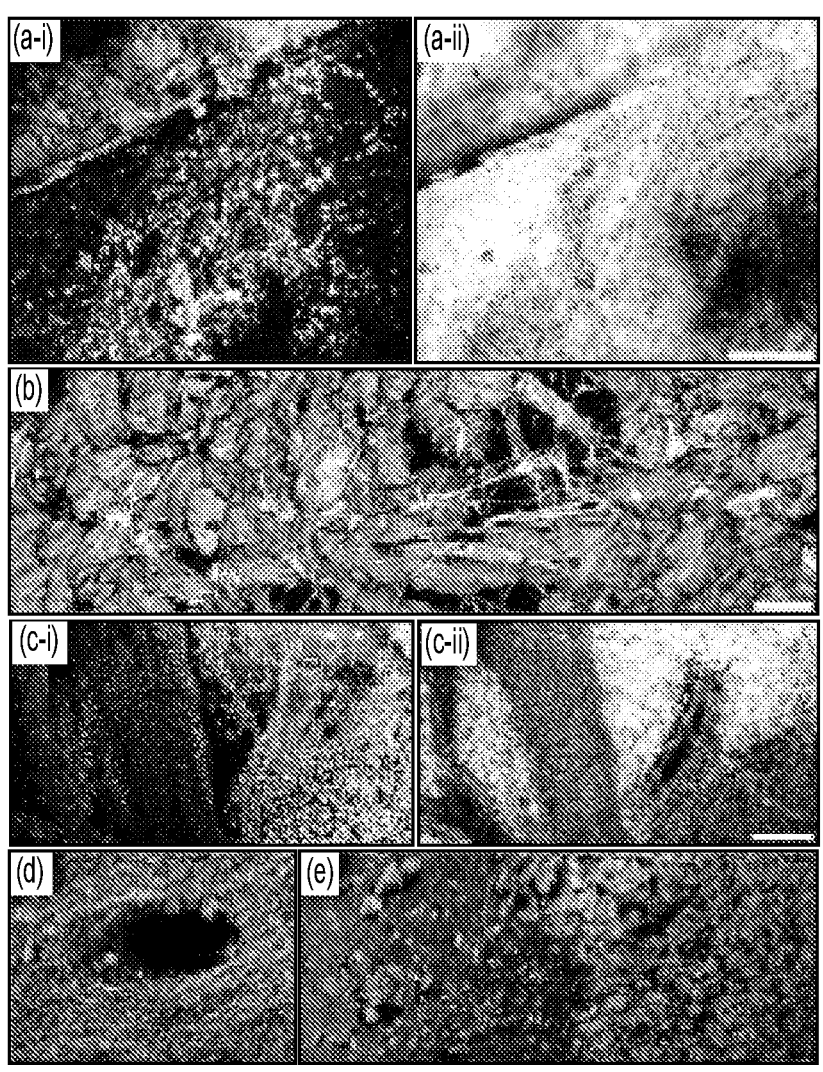
FIG. 11 shows examples of TA-PARS imaging.

FIG. 11 shows an example of TA-PARS imaging. In view (a), TA-PARS captured the epithelial layer at the margin of resected human skin tissues. The stratum coroneum layer was captured in the radiative and non-radiative visualizations concurrently. The radiative visualization provides improved contrast in recovering these tissue layers as compared to the non-radiative image. In another subcutaneous region of the resected human skin tissues in view (b), the TA-PARS captures connective tissues, with sparse nuclei, and elongated fibrin features.

The proposed system was also applied to imaging resected unprocessed rattus brain tissues. In view (c), the TA-PARS acquisition highlights the gray matter layer in the brain revealing dense regions of nuclear structures. The nuclei of the gray matter layer are presented with higher contrast relative to surrounding tissues in the non-radiative image as compared to the radiative representation. Since nuclei do not provide significant radiative contrast the nuclear structures in the radiative image appear as voids or lack of signal within the specimen. While some potential nuclei may be observed, they may not be identified with significant confidence, as compared to those in the TA-PARS non-radiative representation. Along the top right of the non-radiative acquisition, structures resembling myelinated neurons can be identified surrounding the more sparsely populated nuclei in that area.

In view (d), further acquisitions in neighboring regions accentuate the apparent myelinated neuron structures. Dense structures indicative of the web of overlapping and inter-connected dendrites and axons are apparent within these regions, where tightly woven neuronal projections are observed arranged around a void in the tissue. Then, zooming out to a larger nearby imaging field, in view (e), sections of distinct tissues were recovered with the non-radiative contrast. The left side of the field contains dense bundles indicating myelin projections into potentially gray matter with larger nuclei, as opposed to the right side, which is potentially white matter containing more myelinated structures with decreased nuclear density.

Figures 12A, 12B:
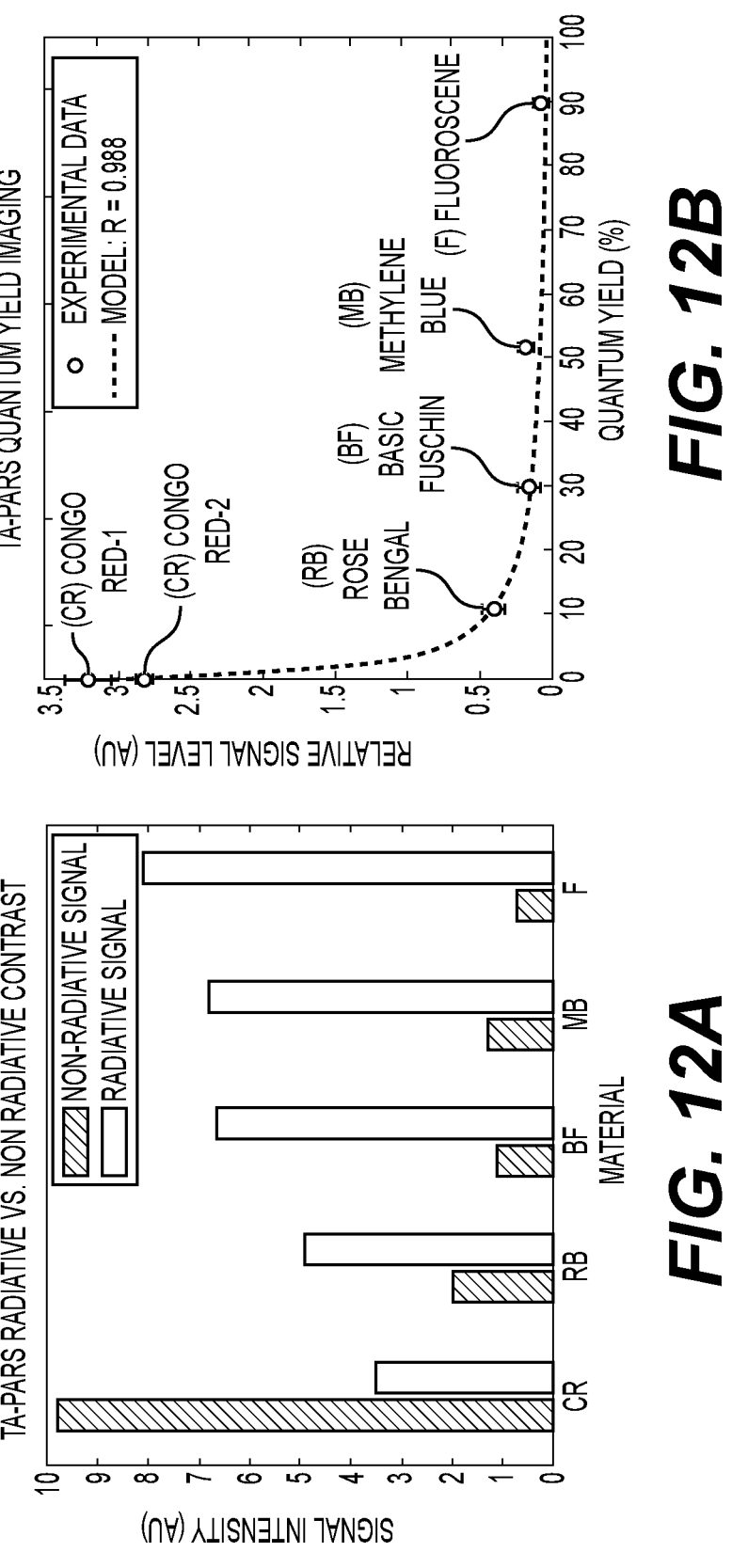
FIG. 12 shows exemplary applications of a quantum efficiency ratio (QER).

Referring to FIG. 12, the QER or the ratio of the non-radiative and radiative absorption fractions is expected to contain further biomolecule-specific information. Ideally, the local absorption fraction should correlate directly with radiative relaxation properties. Relative radiative and non-radiative signal intensities may be plotted, and QER may be plotted against reported quantum efficiency (QE) values.

In one example, the TA-PARS was applied to measure a series of fluorescent dyes with varying quantum efficiencies. The 515 nm excitation was used to generate radiative and non-radiative relaxation signals which were captured simultaneously.

An example of relative radiative and non-radiative signal intensities were plotted, as shown in FIG. 12, view (a). The QER is then plotted against reported QE values for the samples, as shown in view (b). The radiative PARS signals ($P_r$) are expected to increase linearly with the QE ($P_r \propto QE$), while the non-radiative PARS ($P_{nr}$) signals are expected to decrease linearly with QE ($P_{nr} \propto 1-QE$). Therefore, the fractional relationship between the non-radiative and radiative signals is represented by the quotient of the linear functions ($QER = P_r/P_{nr} \propto QE/(1-QE)$). The empirical results fit well to this expected model (R=0.988).

Figure 13:
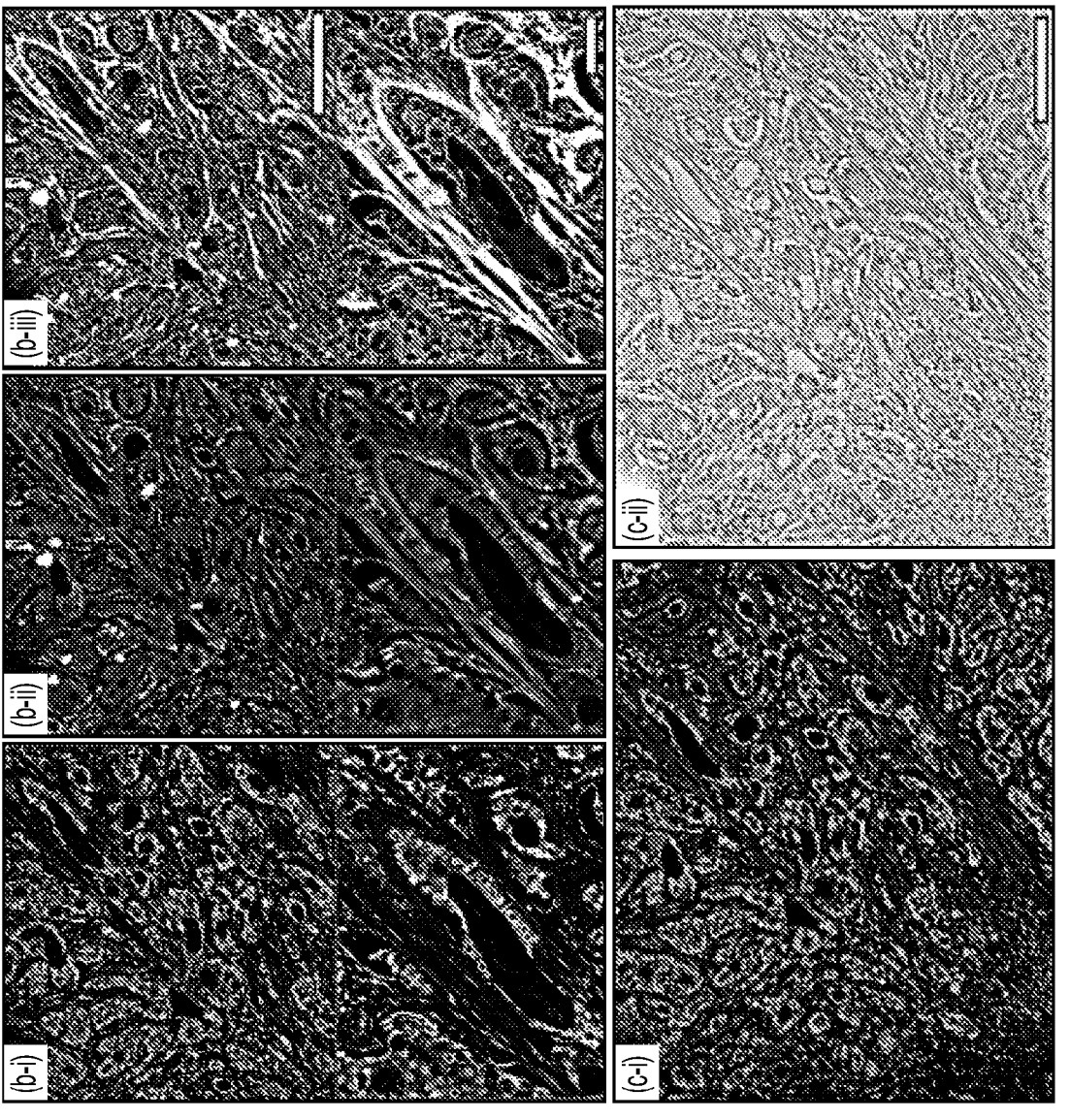
FIG. 13 shows examples of TA-PARS imaging using a QER acquisition process.

FIG. 13 exemplifies images from a QER acquisition process applied to imaging of thin sections of FFPE human tissues. Based on the non-radiative and radiative signals, the QER was calculated for each image pixel, generating a QER image. The result represents a dataset encoding chromophore-specific attributes, in addition to the independent absorption fractions. The QER processing helps to further separate otherwise similar tissue types from solely the radiative or non-radiative acquisitions.

A colorized version of the QER image shown in FIG. 13 highlights various tissue components. The low QER biomolecules (DNA, RNA, etc.) may appear as a first color (e.g., a color having a lower wavelength or a light blue color), while the high QER biomolecules (collagen, elastin, etc.) may appear as a second color and/or a third color different from (e.g., having a higher wavelength than) the first color (e.g., pink and purple). Compared to the H&E visualization captured following the QER imaging session (FIG. 13, view (c-ii)), collagen and elastin (which may appear as a fourth color or dark red) composing the fibrous connective tissues may be easy to identify due to their low QER. Conversely, nuclear structures are appreciable in the first color and/or a fifth color (e.g., blue) due to their high QER. The connective tissues surrounding the carcinoma cells are also differentiated from the fibrous connective tissues in a sixth color (e.g., purple) in the QER visualization as compared to the H&E-stained image. In calculating the QER from the TA-PARS a complementary imaging contrast is provided, enabling further chromophore specificity than is accessible with radiative or non-radiative modalities independently. Although the terms first color, second color, third color, fourth color, fifth color, and sixth are used, aspects disclosed herein may not be limited to six, etc. predetermined colors. The color appearing in the visualization may have a wavelength proportional to the QER. For example, structures with a higher QER may appear as colors with higher wavelengths (e.g., red) and structures with a lower QER may appear as colors with lower wavelengths (e.g., blue).

Although the QER method presented here relies on extracted intensity values, similar analogs may be conceived which involve similar such ratios of others signal parameters such as lifetime, rise time, signal shape, frequency content, etc.

Label-Free Histological Imaging

The TA-PARS mechanism may provide an opportunity to accurately emulate traditional histochemical staining contrast, such as H&E staining, and TA-PARS may provide label-free histological imaging. The non-radiative TA-PARS signal contrast may be analogous to that provided by hematoxylin staining, while the radiative TA-PARS signal contrast may be analogous to that provided by eosin staining. The TA-PARS may capture label-free features such as adipocytes, fibrin, connective tissues, neuron structures, and cell nuclei. Visualizations of intranuclear structures may be captured with sufficient clarity and contrast to identify individual atypical nuclei.

Figure 14:
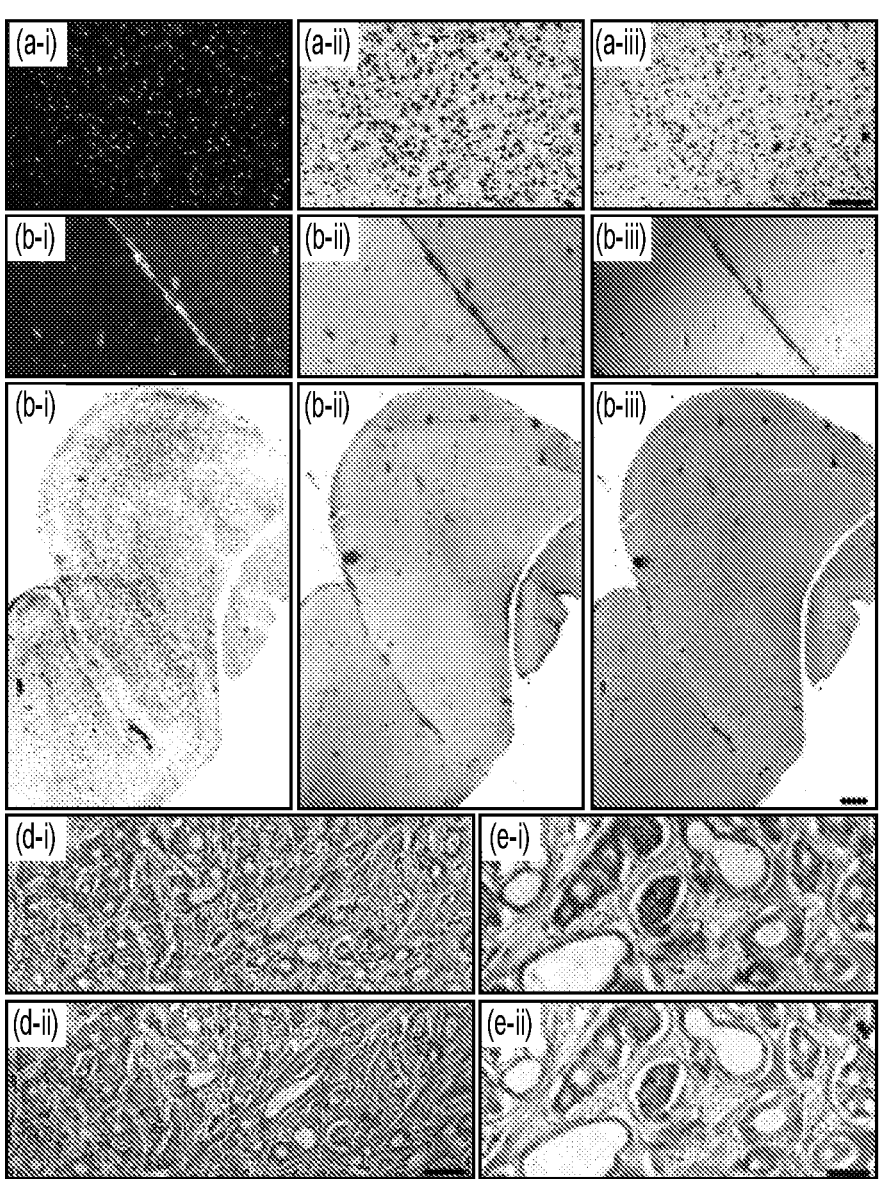
FIG. 14 shows comparisons of imaging using a QER acquisition process with traditional stains.

FIG. 14 shows an example of label-free histological imaging applied to FFPE human brain tissue. Referring to FIG. 14, the non-radiative TA-PARS signal contrast is analogous to that provided by the hematoxylin staining of cell nuclei (FIG. 14, view (a)). A section of FFPE human brain tissue was imaged with the non-radiative PARS (FIG. 14, view (a-i)). This non-radiative information was then colored to emulate the contrast of hematoxylin staining (FIG. 14, view (a-ii)). The same tissue section was then stained only with hematoxylin and imaged under a bright-field microscope (FIG. 14, view (a-iii)), providing a direct one-to-one comparison. These visualizations are expected to be highly similar since the primary target of hematoxylin stain and the non-radiative portion of TA-PARS is nuclei, though other chromophores will also contribute to some degree.

A similar approach was applied to eosin staining in an adjacent section. The adjacent section was imaged with the radiative PARS (FIG. 14, view (b-i)). This radiative information was then colored to emulate the contrast of eosin staining (FIG. 14, view (b-ii)). This section was then stained with eosin (FIG. 14, view (b-iii)), providing a direct one-to-one comparison of the radiative contrast and eosin staining. In each of the TA-PARS and eosin-stained images, analogous microvasculature and red blood cells were resolved throughout the brain tissues. These visualizations are expected since the primary targets of the radiative portion of TA-PARS include hemeproteins, NADPH, flavins, collagen elastin and extracellular matrix, closely mirroring the chromophores targeted by eosin staining of extranuclear materials.

As the different contrast mechanisms of the TA-PARS closely emulate the visualizations of H&E staining, the proposed system may provide true H&E-like contrast in a single (only one or exactly one) acquisition. The TA-PARS may provide substantially improved visualizations compared to previous PARS emulated H&E systems which relied on scattering microscopy to estimate eosin-like contrast. The scattering microscopy-based methods are unable to provide clear images in complex scattering samples such as bulk resected human tissues. In contrast, the TA-PARS can directly measure the extranuclear chromophores via radiative contrast mechanisms, thus providing analogous contrast to H&E regardless of specimen morphology. Here, the different TA-PARS visualizations were combined using a linear color mixture to generate an effective representation of traditional H&E staining within unstained tissues.

An example in resected FFPE human brain tissue is shown in FIG. 14, view (c). The wide field image highlights the boundary of cancerous and healthy brain tissues.

To qualitatively compare the TA-PARS to traditional H&E images, a series of human breast tissue sections was scanned with the TA-PARS (FIG. 14, view (d-i) and FIG. 14, view (e-i)), then stained with H&E dyes and imaged under a brightfield microscope (FIG. 14, view (d-ii) and FIG. 14(e-ii)). The TA-PARS emulated H&E visualizations are effectively identical to the H&E preparations. In both images, clinically relevant features of the metastatic breast lymph node tissues are equally accessible.

Lifetime Imaging

H&E simulations may be enhanced by extracting time-domain features, which are discussed in more detail in the below section discussing TD-PARS and Feature Extraction Imaging. While the total amplitude of the PARS modulation captures the local absorption of the excitation, the evolution of the pressure and temperature induced modulations will also capture local material properties.

Figure 15:
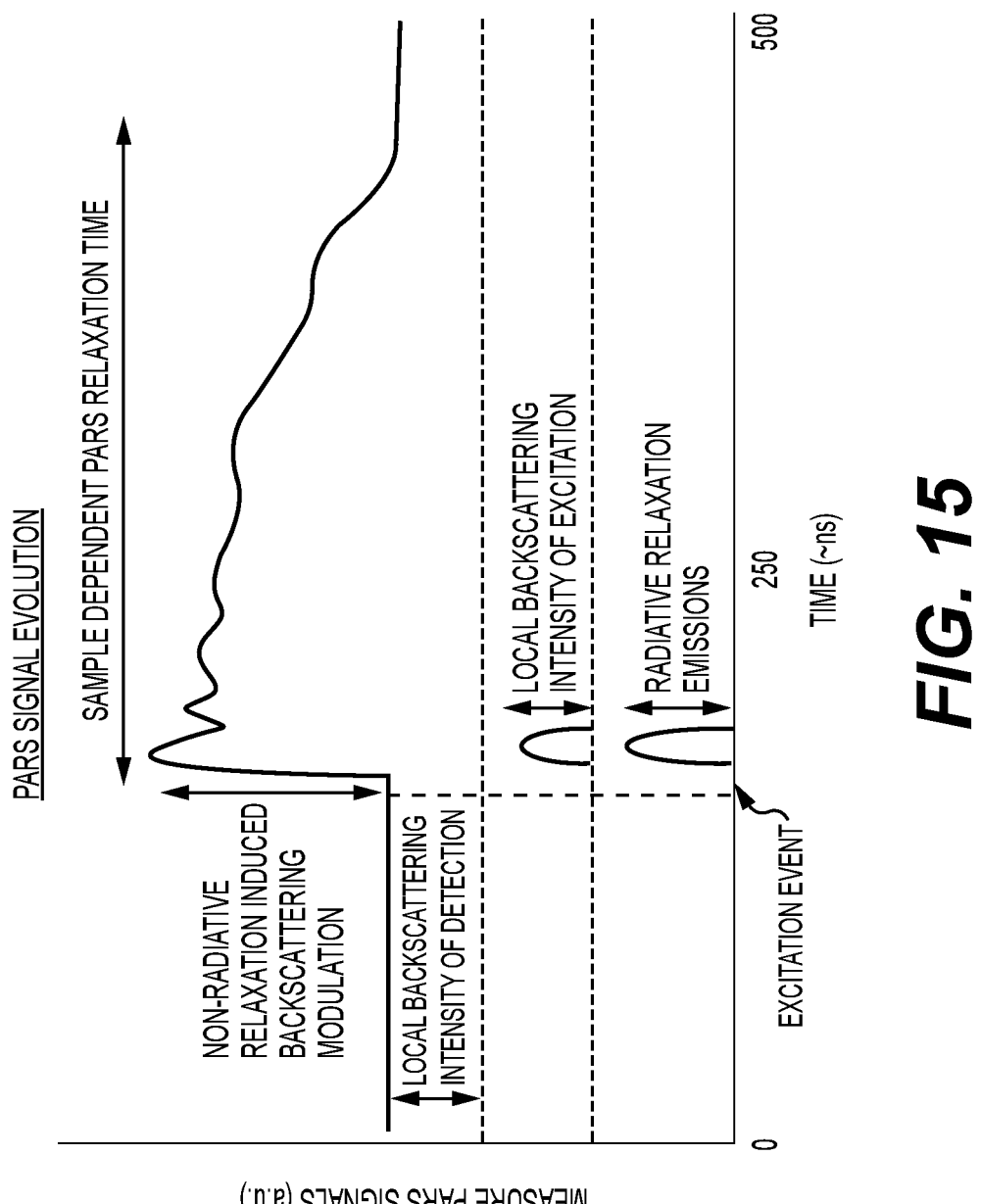
FIG. 15 shows an exemplary PARS signal evolution.

FIG. 15 exemplifies a PARS signal evolution over time. Each PARS excitation event will capture the scattering of the detection and excitation sources, the radiative emissions, and the PARS non-radiative relaxation time domain signal. Referring to FIG. 15, the PARS decay or evolution time is likely tied to metrics such as the thermal and pressure confinement times which govern traditional photoacoustic imaging. This means that properties such as the thermal diffusivity, conductivity, and speed of sound may dictate the PARS relaxation time. By measuring the decay or evolution time, the PARS may then provide further chromophore specific information on a specimen. This may enable chromophore unmixing (e.g. detect, separate, or otherwise discretize constituent species and/or subspecies) from a single excitation event, or single shot functional imaging.

Figure 16:
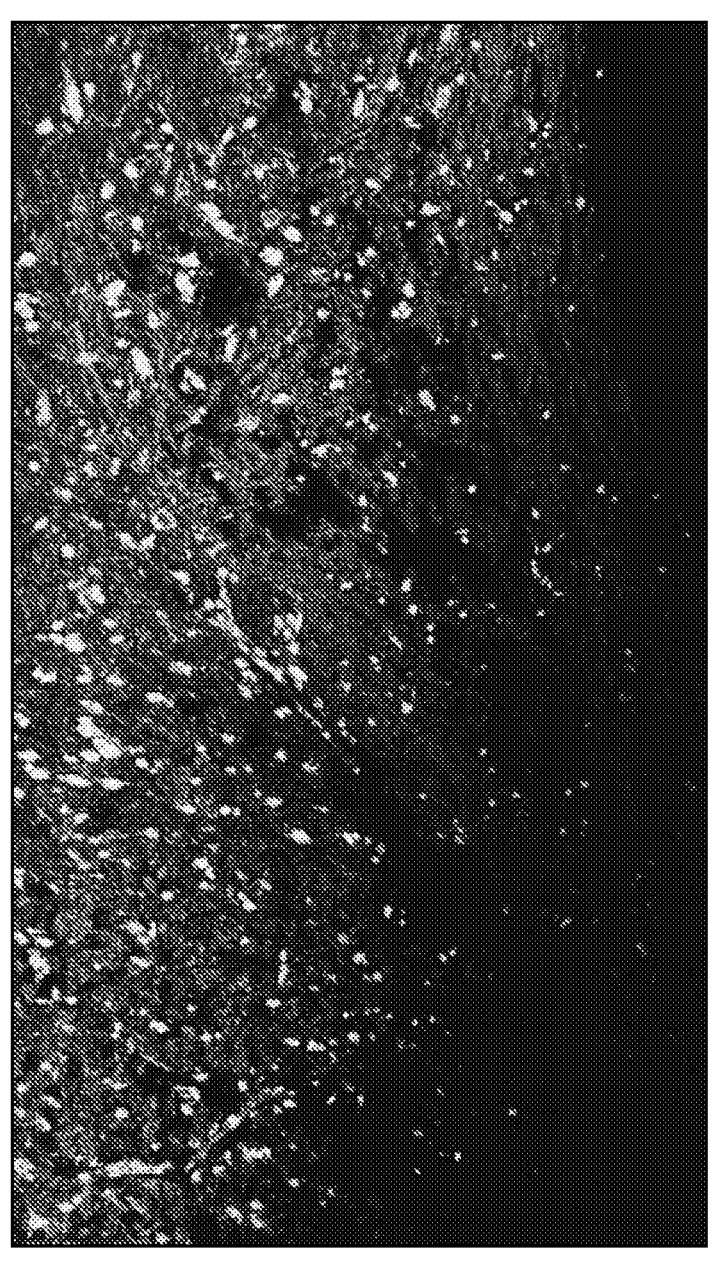
FIG. 16 shows an example of a lifetime PARS image in resected rattus brain tissues.

An example of a lifetime PARS image in resected rattus brain tissues is shown in FIG. 16. Here the nuclei (which may appear as a first color such as white) are unmixed from the surrounding gray matter (which may appear as a second color such as green) and the interwoven myelinated neuron structures (which may appear as a third color such as orange). This unmixing is performed based on the PARS lifetime signals.

Figure 17:
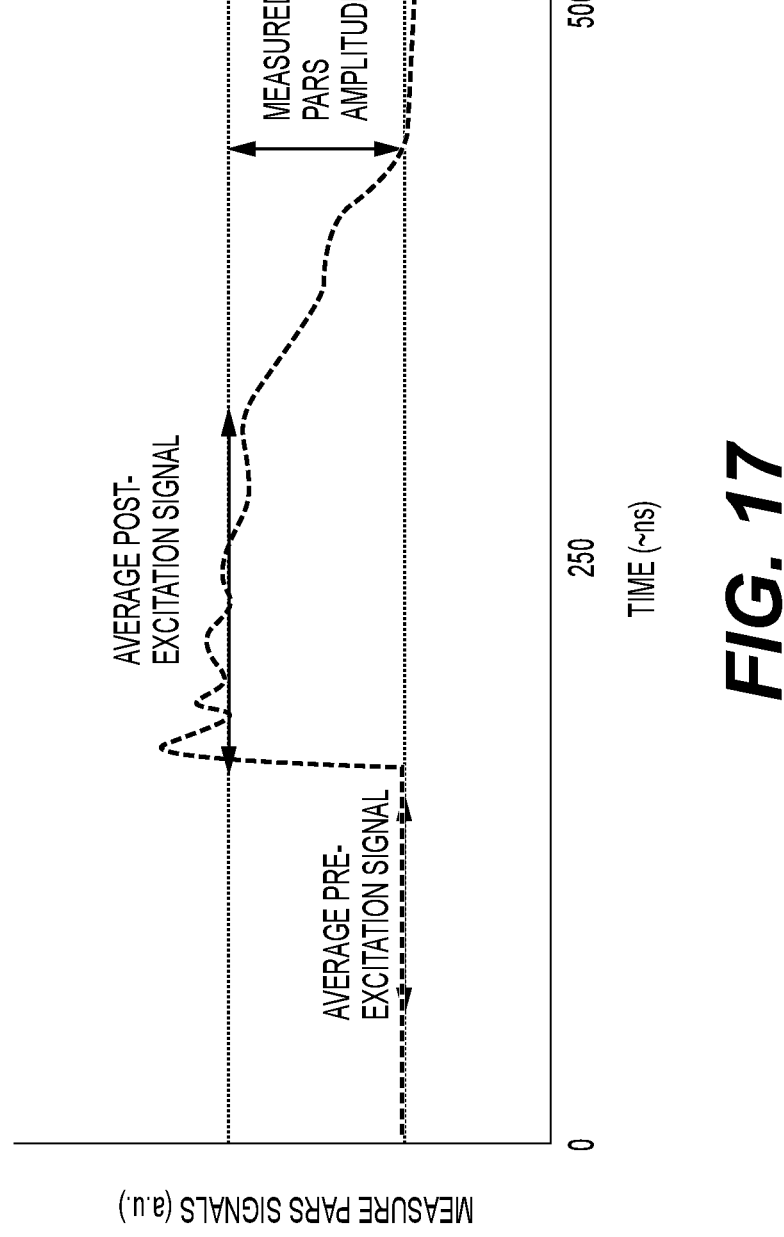
FIG. 17 shows an exemplary PARS signal evolution in connection with a rapid lifetime extraction technique.

Referring to FIG. 17, a rapid lifetime extraction technique may be used to greatly improve the PARS collection contrast. Referring to FIG. 17, PARS amplitude may be calculated as the difference between the average pre- and post-excitation signal. This acquisition is less sensitive to imaging noise compared to alternative extraction techniques. Previously, PARS used a min-max acquired signal approach to extract the PARS-specific signals. By capturing the minimum of the signal minus the maximum, the PARS may highlight the total amplitude of the PARS modulation. However, this is highly susceptible to collection and measurement noise in the PARS signals.

One possible signal extraction method can be performed by determining an average pre-excitation signal. Then the average post-excitation signal is calculated from the initial portion of the lifetime signal. The PARS amplitude is then calculated as the difference between the two average signals. This metric for rapid signal extraction provides substantial improvements in signal to noise ratio, and sensitivity when collecting PARS signals. Since the technique relies on average signals, the PARS collection is substantially less sensitive to acquisition noise.

Additional time-based imaging methods will be discussed in more detail in the below section on TD-PARS and Feature Extraction Imaging. First, two other PARS will be briefly discussed.

MP-PARS

Figure 18:
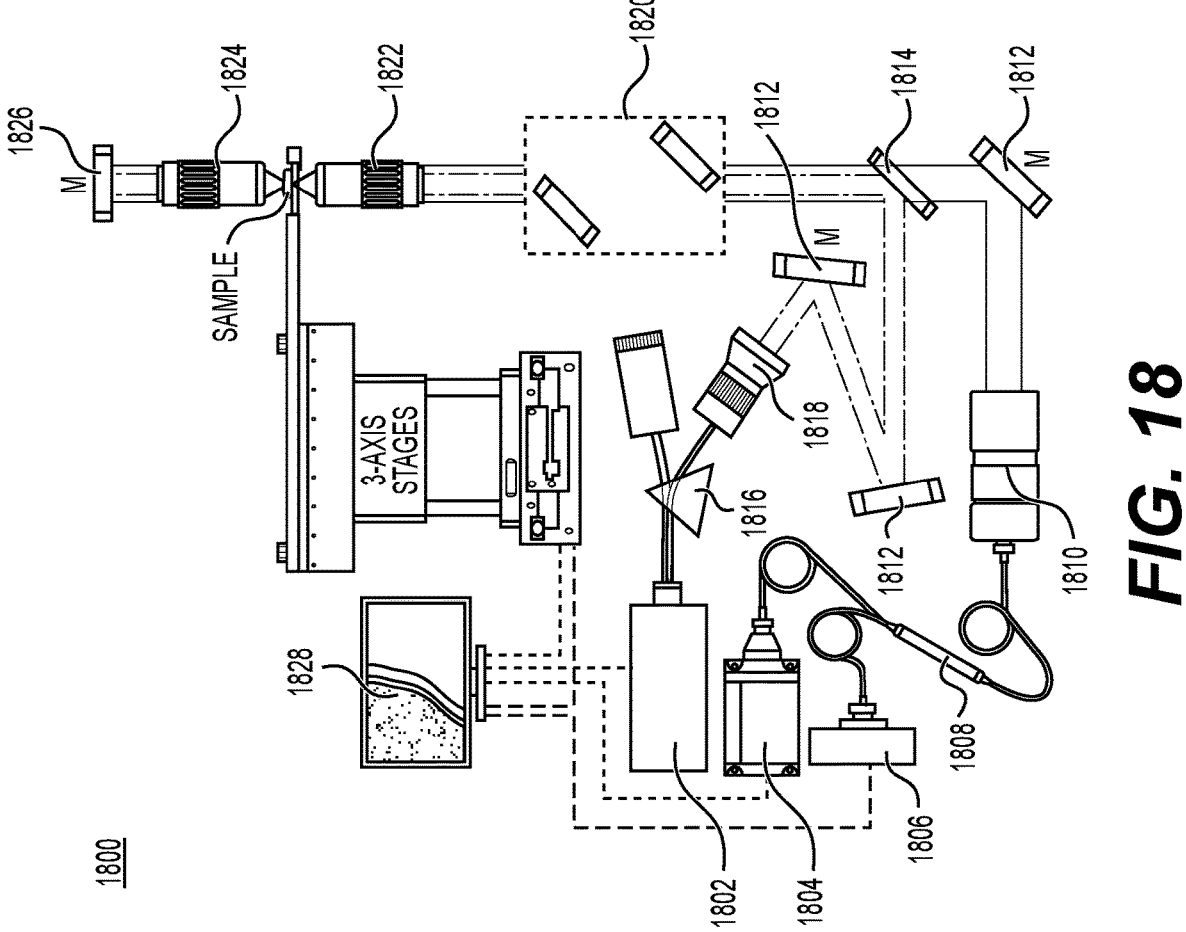
FIG. 18 shows exemplary architecture for a multi-pass (MP) PARS system.

Referring to FIG. 18, in multi-pass PARS (MP-PARS), the backscattered detection may be captured and subsequently redirected back to the sample where it interacts with the sample again before it is detected. Each time the detection interacts with the sample, it may pick up further information of the PARS modulation.

In PARS, the non-radiative absorption induced perturbations in the optical properties are visualized using a secondary co-focused detection laser. The detection laser is co-focused with the excitation spot such that the absorption induced modulations may be captured as changes in the backscatter intensity of the detection laser. For a given detection intensity $I_{det}$, before the excitation pulse interacts with the sample the signals can be approximated based on the following relationship: $PARS_{pre-ext} \propto I_{det}(R)$, where R is the unperturbed reflectivity of the sample.

Once the excitation pulse interacts with the sample, the signal may be approximated as: $PARS_{post-ext} \propto I_{det}(R+\Delta R)$, where the pressure and temperature induced change in reflectivity are denoted by AR. The total PARS absorption contrast is then approximated as: $PARS_{sig} \propto PARS_{post-ext} - PARS_{pre-ext}$. Substituting the previous relations for $PARS_{pre-ext}$ and $PARS_{post-ext}$ leads to the following: $PARS_{sig} \propto I_{det}(R+\Delta R) - I_{det}(R)$.

Before the excitation pulse the backscattering of the MP-PARS is then approximated based on the following relationship: $MPPARS_{pre-ext} \propto (I_{det}(R))^n$ where R is the unperturbed reflectivity of the sample, and n is the number of times the excitation interacts with the sample. Once the excitation pulse interacts with the sample, the signal may be approximated as: $MPPARS_{post-ext} \propto (I_{det}(R+\Delta R))^n$ where the pressure and temperature induced change in reflectivity are denoted by AR.

The total MP-PARS absorption contrast is then approximated as: $MPPARS_{sig} \propto MPPARS_{post-ext} - MPPARS_{pre-ext}$. Substituting the previous relations for $MPPARS_{pre-ext}$ and $MPPARS_{post-ext}$ leads to the following: $MPPARS_{sig} \propto (I_{det}(R+\Delta R))^n - (I_{det}(R))^n$ where n is the number of times the detection interacts with the sample. PARS signals may be expanded non-linearly by these repeated interactions of the backscattered detection with the sample. The detection may then be redirected to interact with the sample any number of times, resulting in a corresponding degree of non-linear expansion in the non-radiative absorption contrast.

MP-PARS architectures, such as an architecture 1800 exemplified in FIG. 18, may be oriented such that passes consist of reflection or transmission events, which may occur at normal incidence to the sample or at some relevant transmission or reflection angle. For example, if the target features a particularly strong Mie-scattering angle, it may be advantageous to orient the multiple passes along this direction. Multiple passes may occur along a single (only one or exactly one) path (such as a normal-incidence reflection), or along multiple paths such as a normal-incidents transmission architecture, or even architectures with additional (more than two) pathways to take advantage of additional spatial non-linearities.

For example, an MP-PARS architecture 1800 may include an excitation source 1802 (e.g., 266 nm excitation source or laser), one or more detection sources 1804 (e.g., a 405 nm detection source or laser), one or more photodiodes or photodetectors 1806, a circulator 1808, a collimator 1810, one or more mirrors 1810 to guide the excitation and/or detection light, a prism 1816, and a variable beam expander 1818. In addition, the MP-PARS architecture 1800 may include a pair of alignment mirrors 1820 to align the excitation and/or detection light, and one or more scanners or scanning heads 1822, 1824 arranged at different sides of the sample. The one or more scanners may include a first scanner 1822 to transmit excitation and detection light to the sample, and a second scanner 1824, arrange with mirror 1826, to allow for multiple passes. A computer 1828 may be used to analyze the received signals and/or control the excitation and detection sources 1802 and 1804.

MP-PARS can act as an optical amplifier for detected PARS signals. It can be employed the same way that laser cavity systems or photomultiplier tubes are implemented to further improve the sensitivity of the measured signal. This may result in substantial improvements in PARS imaging fidelity. PARS may be captured with improved sensitivity to any or all of the radiative, non-radiative, or scattering contrast facilitating acquisitions with lower imaging powers. This may facilitate acquisition of lower concentrations of chromophores, chromophores with lower optical absorption, or to reduce sample exposure. These non-linear effects may be leveraged to improve recovered imaging resolution by taking advantage of non-linear spatial dependencies to provide super-resolution imaging.

Multi-Photon Excitation PARS

Referring to FIG. 19, multi-photon PARS may provide several benefits over traditional PARS excitation. In multiphoton excitation, a number of photons are absorbed by a target at virtually the same instant and/or in a single (only one or exactly one) event. The energy of these photons is then added together such that the absorbed photons are equivalent to a single (only one or exactly one) higher energy and shorter wavelength photon. Here two photons with half the energy and twice the wavelength of the single photon excitation event are absorbed by a chromophore providing analogous excitation.

In PARS, as in fluorescence microscopy, non-linear absorption mechanisms may be leveraged. Traditionally, PARS targets single photon absorption effects, for example the 266 nm UV excitation of DNA. However, the PARS may also target multiphoton absorption characteristics such as those used in multiphoton fluorescence microscopy. In multiphoton microscopy, a number of photons are absorbed by a target at virtually the same instant. The energy of these photons is then added together such that the absorbed photons are equivalent to a single higher energy and shorter wavelength photon.

In the case of two-photon PARS, the excitation wavelength would be selected as double the traditional value. Two photons would then be absorbed simultaneously providing an excitation event equivalent to standard one-photon excitation (FIG. 19). In the example listed above, rather than using 266 nm UV excitation to target DNA, a 532 nm excitation could be used to target the absorption of DNA. The two photon 532 nm absorption is equivalent to a single 266 nm absorption. Aspects disclosed herein are not limited to 532 nm excitation. The wavelength of the excitation may be configured to be double a predetermined excitation wavelength, such as double of a UV wavelength (e.g., double 100-400 nm) or a UVC wavelength (100-280 nm).

One primary difference between a multi-photon PARS and a conventional single-photon PARS architecture is the requirement for high instantaneous optical energy densities. In order to minimize sample exposure levels to pragmatic levels, this architecture may require the use of very short optical excitation pulses, on the order of single picosecond or shorter. Such a requirement may be unique to the multi-photon PARS.

The multi-photon PARS may provide several benefits over traditional PARS excitation. First, multiphoton excitation uses longer-wavelength photons, which are lower energy and penetrate more deeply. Second, moving towards longer wavelengths may provide further biological compatibility avoiding tissue damage. This is especially prevalent in the case of in-situ histology since the PARS UV excitation may not be compatible with imaging deep into the body. It also can improve the safety of PARS system to be used for in-situ applications.

TD-PARS and Feature Extraction Imaging

PARS operates by capturing nanosecond-scale optical perturbations generated by photoacoustic pressures. These time-domain (TD) modulations are usually projected by amplitude to determine absorption magnitude. A single characteristic intensity value may be extracted from each TD signal to visualize the total absorption magnitude at each point. For example, TD amplitude, computed as the difference between the maximum and minimum of the TD signal, is commonly used to represent the absorption magnitude.

However, significant information on the target's material properties is contained within the TD signals. Time-evolution of PARS signals may be dictated by material properties such as the density, heat capacity, and acoustic impedance. H&E-like visualizations may be generated directly from PARS time domain data by applying AI-algorithms which bypass the PARS image reconstruction step. This approach is beneficial compared to direct PARS-to-H&E image-to-image translation as it provides additional valuable information which can help to better discriminate between different tissue types in the image.

Figure 20B:
FIGS. 20A and 20B show a reconstructed grayscale PARS image and a corresponding stain.
Figure 20A:
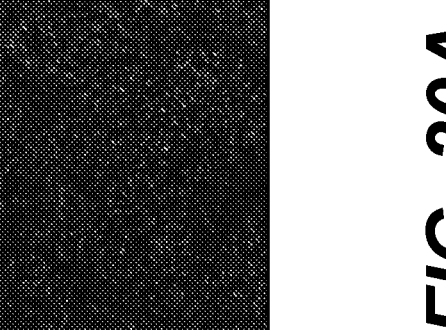

Referring to FIGS. 20A and 20B, H&E-like representations may be made by the application of AI image-to-image translation algorithms based on conditional generative adversarial networks (cGANs). These methods learn color transfer mappings from paired or unpaired samples of the source and the reference representations. In this way, reconstructed grayscale PARS images (20A) can be mapped into color H&E data (20B).

Imaging modalities may scan, pixel-by-pixel, capturing a signal over time at each pixel. While scanning over time may be continuous, realistically, signals are recorded periodically or discretely using an image acquisition system. Characteristic values may be extracted from each signal, accomplished by either using a Hilbert transform to find an envelope of the signal, from which the difference between maximum and minimum values may be computed, or by directly computing the difference between the maximum and minimum of the raw signal itself.

Referring to FIGS. 21A and 21B, methods and techniques disclosed herein may bypass an image reconstruction stage where images are reconstructed by extracting the amplitude of the captured optical absorption signals or averaging their values over time. Methods and techniques disclosed herein may directly use signal representations as input to the AI colorization algorithm instead of the pixels of the reconstructed image. In this way, additional valuable information on the underlying tissue can be included to create virtual H&E-like images.

To make the colorization algorithm more computationally efficient, some compressed representations of the time domain signal can be used. These, for example, may include, but are not limited to: principal linear components of the signal, coefficients of other signal decomposition methods, salient signal points, etc. An example of creating an H&E like visualization by applying the Pix2Pix algorithm is shown in FIG. 21. FIG. 21A shows three principal components of the time domain signals, and FIG. 21B shows the corresponding synthesized H&E image. Differences between FIGS. 20A-B and FIGS. 21A-B may not be readily apparent in black and white, and may be better assessed in color form. For example, FIG. 21A may show some coloring, while FIG. 20A may be black and white and/or grayscale. In addition, FIG. 21B may be less granular and/or show more color than FIG. 20B.

Intelligent Clustering Method

An unsupervised clustering method may be used to form colorized, synthetic H&E images without needing to reconstruct a grayscale image. The clustering method may learn TD features which relate to underlying biomolecule characteristics. This technique identifies features related to constituent biomolecules, enabling single-acquisition virtual tissue labelling. Colorized visualizations of tissue are produced, highlighting specific tissue components. The clustering may be performed on any or all of the PARS radiative, non-radiative, and scattering channels.

For a given biomolecule with constant material properties, the PARS TD signals may have specific shapes. However, signals from a given target may vary in amplitude (e.g. based on concentration) and may suffer from noise. Clustering signals by shape and learning an associated prototype for each cluster may be used to determine constituent time-domain features that capture the material-specific information of the underlying tissue target, regardless of the noise and amplitude variation present in the TD signals.

As an example, a modified K-Means clustering method may be used. Measured signals are treated as vectors, where the vector angle is analogous to signal shape. The distance or difference between TD signals is the sine of the subtended angle, such that orthogonal signals have maximal distance and scaled or inverted signals have zero distance. Cluster centroids are then calculated as the first principal component of the union set of each cluster and its negative, causing the learned centroids to be robust to noise. Once the TD features (centroids) are learned, corresponding feature amplitudes are extracted by performing a change-of-basis from the time- to feature-domain.

Figure 22:
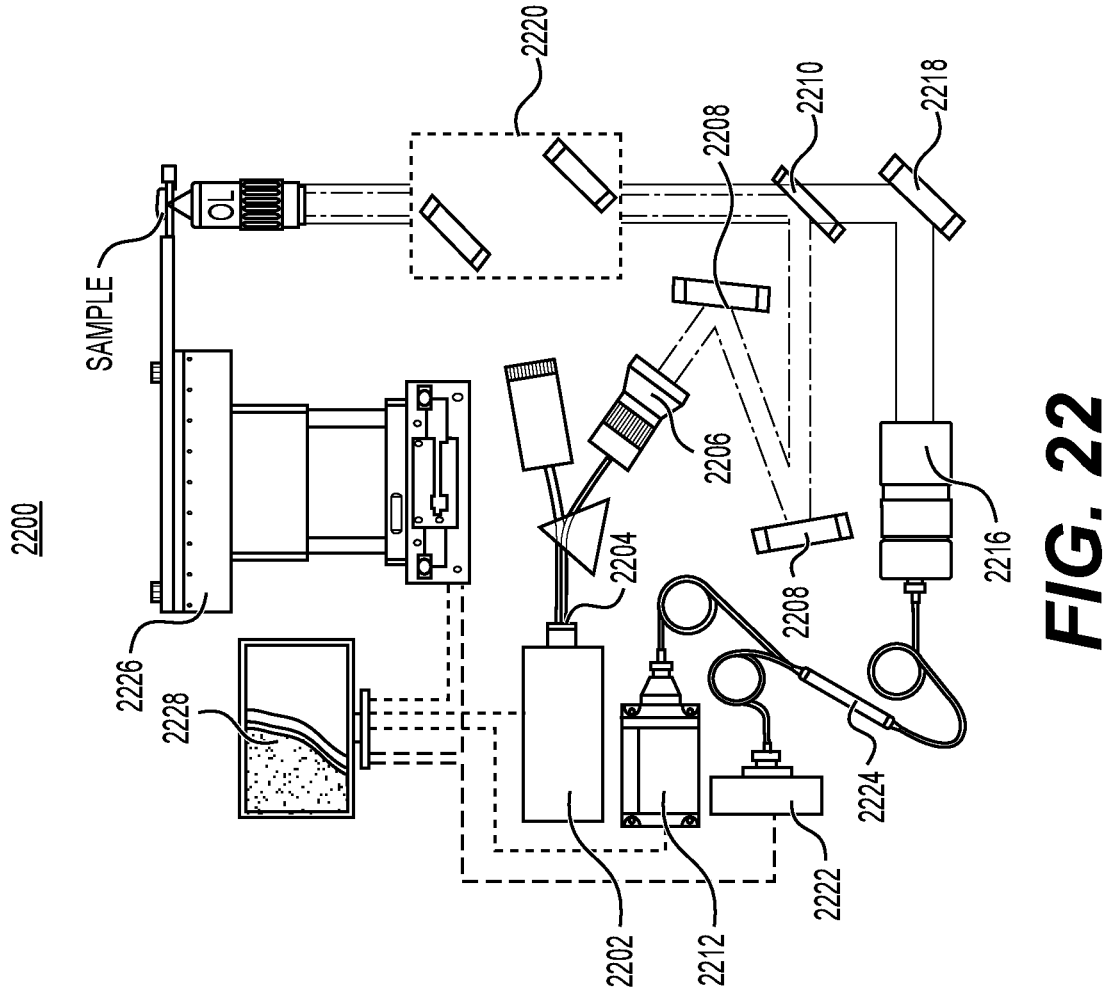
FIG. 22 shows exemplary architecture to analyze TD-PARS signals.

Referring to FIG. 22 showing exemplary architecture 2200, a broadly absorbed UV excitation (e.g., 266 nm) may target several biomolecules such as collagen, elastin, myelin, DNA, and RNA with a single (only one or exactly one) excitation. Subsequently, the clustering approach may be used to create enhanced absorption contrast visualizations and to extract biomolecule-specific features from the TD signals. UV excitation may be provided by an excitation light source 2202, such as a 50 kHz 266 nm laser (e.g., WEDGE XF 266, Bright Solutions). Excitation may be spectrally filtered with a prism 2204, then expanded (e.g., with a variable beam expander or VBE 2206) before combination with the detection beam. Excitation light may be guided via one or more mirrors 2208.

Detection light may be provided by a detection light source 2212, such as a continuous-wave 405 nm OBIS LS laser. The detection may be fiber-coupled through the circulator 2214, collimated (e.g., using collimator 2216), then combined with the excitation beam via a dichroic mirror 2210. Detection light may be guided via one or more mirrors 2218

Combined excitation and detection may pass through a pair of alignment mirrors 2200 and be co-focused through a UV-transparent window onto the specimen. Back-reflected light from the sample may return to the collimator 2216 and circulator 2214 by the same path as forward propagation. The circulator 2214 may re-direct backscattered light to a photodiode 2222 capturing the nanosecond-scale intensity modulations. During image acquisition, the stages 2226 may raster scan the specimen over the objective lens, while the excitation pulses continuously. Analog photodiode output may be captured for each excitation event using a high-speed digitizer, forming the PARS TD signals. Using a stage position signal, each PARS TD may be then mapped to a pixel in the final image, which may be output on an electronic display and/or a computer 2228.

Figure 23:
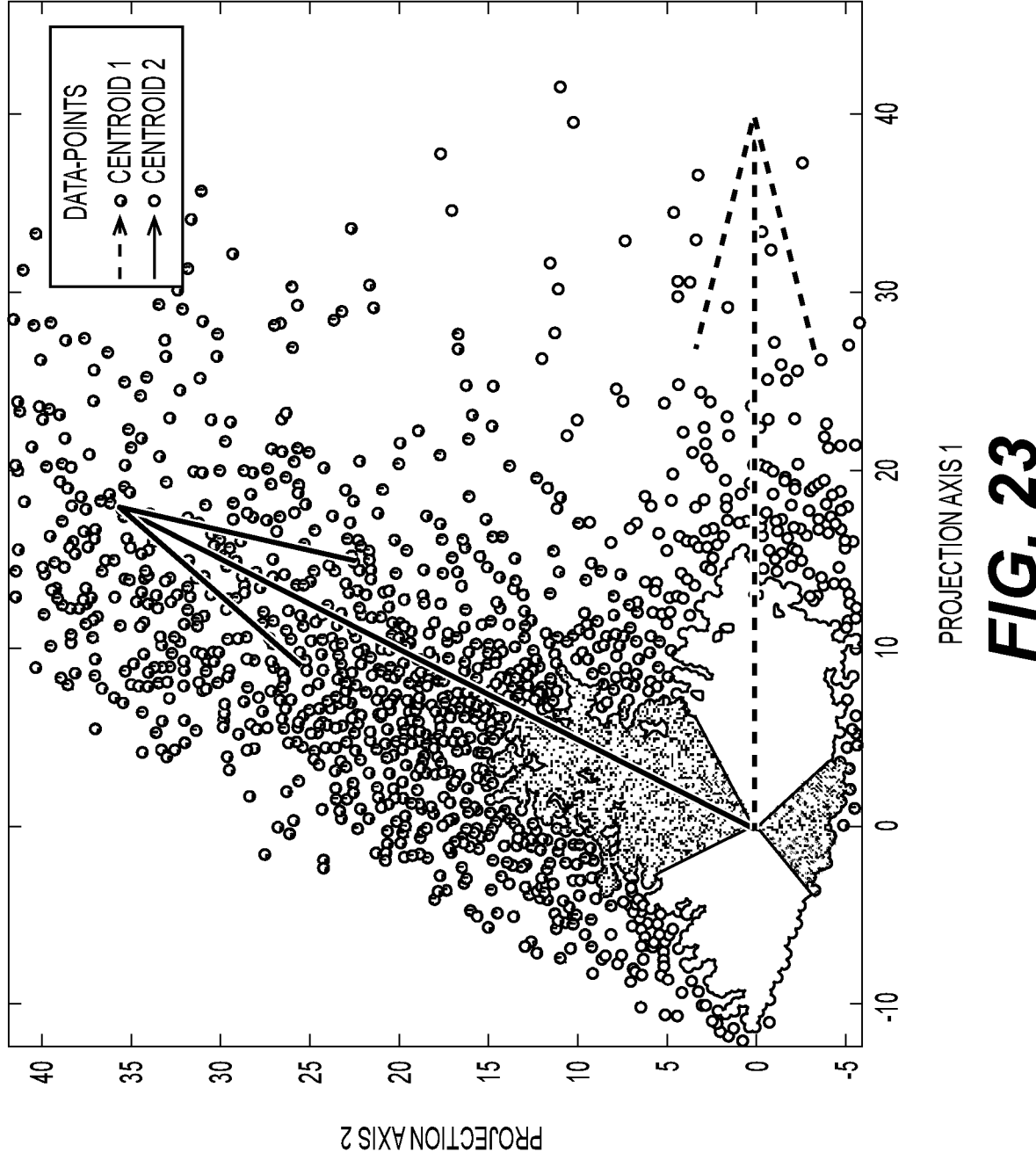
FIG. 23 shows a graph of TD-PARS signals and centroids.
Figure 24:
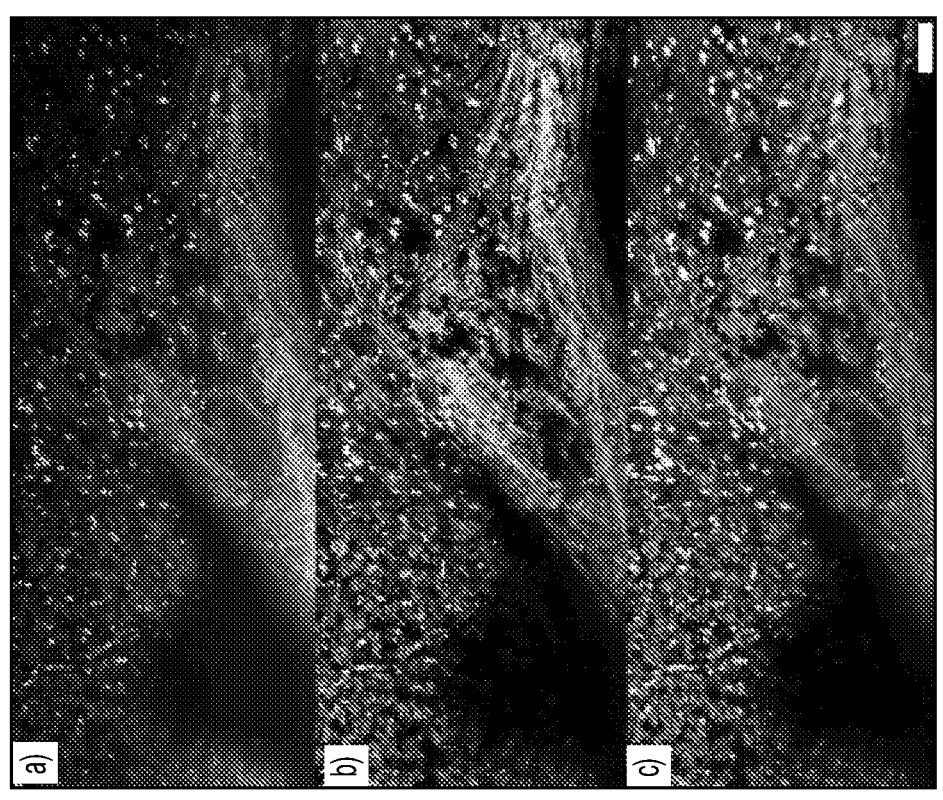
FIG. 24 shows a visualization using a clustering method.

Referring to FIGS. 23-24, instead of defining pixel values by the TD signal amplitude, the proposed K-means method may leverage the TD features depending on a number of extracted clusters. If only a single feature is requested (K=1), the clustering algorithm yields a feature, containing the TD shape similar to all tissue components. This feature can then be used as the basis for matched filtering, a technique designed to optimally extract the amplitude of known signal shapes with additive noise. This provides a robust noise-resistant method for determining absorption amplitude or pixel "brightness." Applied in tissues, this extraction provides a very substantial improvement in structural image quality and noise suppression compared to traditional TD amplitude projection, as shown in FIG. 24, view (a).

If additional clusters are requested (K>1), tissue-specific time-domain features are learned. In this case, the feature amplitudes at each pixel are extracted by performing a change-of-basis from the time-domain to the feature-domain. To visually illustrate the efficacy in learning features, time-domain signals were clustered for K=2 requested features. By projecting the high-dimensional time-domain data onto a two-dimensional plane containing the learned features, it is possible to visualize the TD signals (dots) relative to the identified features (arrows). In the visualization, each point is colored proportionally to the signal content attributed to the constituent features.

Further visualizations are generated for resected murine brain tissues using three features (K=3). The extracted feature amplitudes are mapped to the independent red, green and blue (R,G,B) color channels to form a colorized visualization. Hence, the pixel color represents the proportional mixture of each feature's contribution to the time domain signal, while the intensity represents the total magnitude of absorbed energy. Referring to FIG. 24, view (c), the K=3 colorization demonstrates the potential of the proposed technique in recovering biomolecule-specific information. Structures of singular myelinated neurons (white matter) from the brain stem are illustrated in pink, projecting into the brain. Concurrently, unmyelinated neurons (gray matter) appear on the right side of the frame in green. Finally, nuclear structures scattered throughout the brain tissues appear in white.

Figure 25:
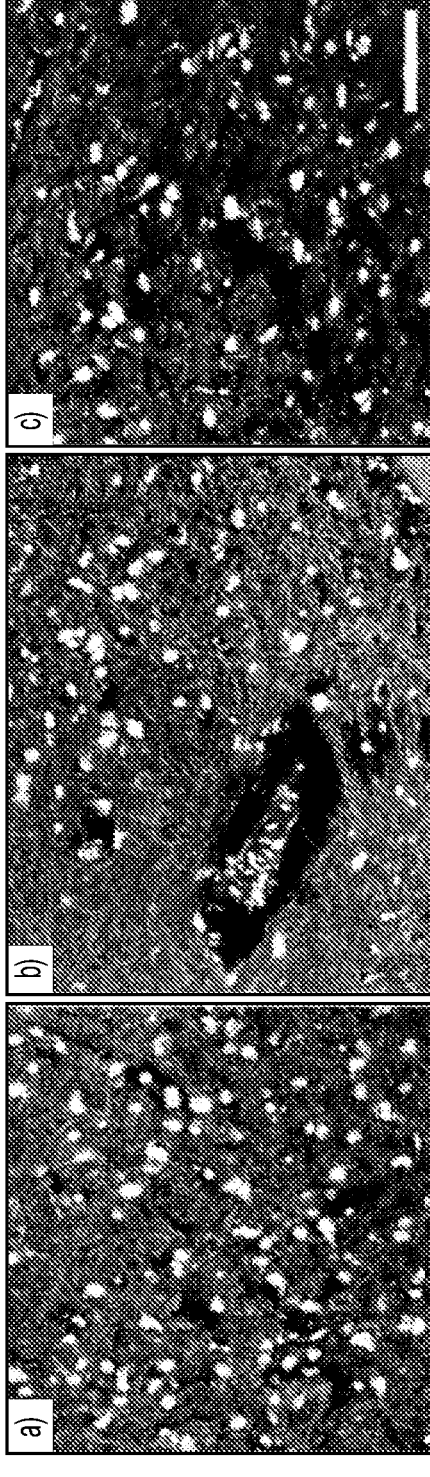
FIG. 25 shows a visualization of three different regions of brain tissues using the clustering method.

Referring to FIG. 25, three different regions of the brain tissues (view (a)), gray matter (view (c)) and the transition or boundary between white and gray matter (view (b)) were selected based on macroscopic inspection. Each unique region was imaged with the PARS microscope, before being colorized using the same K=3 model. In each of the selected regions, the TD colorization highlights identical biomolecule-specific structures as those identified in the initial colorized image (FIG. 24(c)).

The TD signals may be clustered by shape, but not by amplitude. A given pixel (and its corresponding TD signal) may be expressed in terms of characteristic signal shapes of one or more targets and a residual term. Specifically, for a given signal s, and learned characteristic signal shapes (features) $\{f_i\}$, the signal may be represented as $s=\Sigma_i \alpha_i f_i$, such that the weights, $\{\alpha_i\}$, specify the proportion of each characteristic signal shape, with the residual term, r, included to encapsulate any error as a result of modelling or measurement noise.

TD signals may be vectors in space Rn, where the dimension, n, of the space is simply the number of discrete TD samples. Because TD signals are treated as Cartesian vectors, the signal shape is then analogous to the vector angle. A unit-vector pointing in the direction of the non-noise portion of the given cluster may define a centroid. A union set may be constructed of the cluster and its negated points, and the centroid may be found as the direction of greatest variance (the principal component from a sample covariance), allowing higher amplitude signals to have the greatest influence.

A clustering algorithm is reflected in FIG. 26, and a corresponding method 2700 is reflected in FIG. 27. The calculation of cluster centroids is reflected in line 16, and Singular Value Decomposition (SVD) may be used to extract a first principle component. For inputs, the clustering algorithm takes a set, $S=\{s_i(t)\}$, of PARS TD signals and the requested number of clusters (identical to number of learned features), K. Furthermore, the convergence criteria are specified by a minimum number of moves criterion and a difference in mean residual criterion. These are required to ensure convergence.

The algorithm may be run several times, and only the most optimal solution (in terms of minimal mean residual) may be returned. The algorithm initializes by randomly selecting K TD signals to act as initial cluster centroids, shown on lines 1-3 and in step 2702. Next is the "Membership Update" step, shown on lines 7-12 and in steps 2704 and 2706, where the cluster membership of all points (PARS TD signals) is updated by evaluating the distance from each point to each centroid in step 2704, and assigning membership to the associated cluster of the least distant centroid in step 2706. The number of points that move (change cluster membership) is recorded (lines 9-11). Next, in step 2708, the mean residual is evaluated (line 13), as well as the change in the mean residual from the previous iteration (line 14), starting from zero in the case of the first iteration. Next is the "Centroid Update" step, shown on lines 16-21 and in step 2710, where centroids are updated, and are calculated as the first principal component of the union set of each cluster and its negative. Practically this is computed via a Singular Value Decomposition (SVD), shown on line 19. In step 2712, centroids are normalized such that they are unit magnitude. Finally, in step 2714, the convergence criteria are checked. If the algorithm has not converged ("No" in FIG. 27), the "Membership Update" step, followed by the "Centroid Update" step are repeated until the convergence criteria are met ("Yes" in FIG. 27). The algorithm returns, in step 2716, as outputs, a set of cluster labels, indicating which cluster each PARS TD signal is associated to, and a set of K cluster centroids, the learned time-domain features.

PARS TD signals may contain sufficient information to identify biomolecules based on their clustered TD features. Such characteristics may be transferrable across images of different tissue specimens. Feature identification may be performed on an initial specimen, then transferred to others, producing similarly convincing results. Moreover, this technique offers unique advantages as the clustering approach requires no prior information, with the exception of the number of clusters. Training may be performed blindly across the signals captured within the specimen of interest. This is especially beneficial in complex specimens such as the resected brain tissues explored here. The challenge is that blindly clustering for a pre-selected number of features does not guarantee that a singular biomolecule/tissue type will be isolated per feature. Each cluster simply targets a unique characteristic of the PARS TD signals, which may be used to highlight distinct tissue components.

Biomolecules may be visualized based on their PARS TD characteristics. This method may enable a single (only one or exactly one) broadly absorbed excitation source to provide otherwise inaccessible material specificity, while simultaneously targeting the optical absorption of several biomolecules. This could enable enhanced absorption contrast visualizations, acquired in a fraction of the time compared to the analogous multiwavelength approaches. This enables several new avenues for label-free PARS microscopy by adding an additional dimension to the absorption contrast, vastly expanding the potential for biomolecule specificity.

Additional Methods

Figure 28:
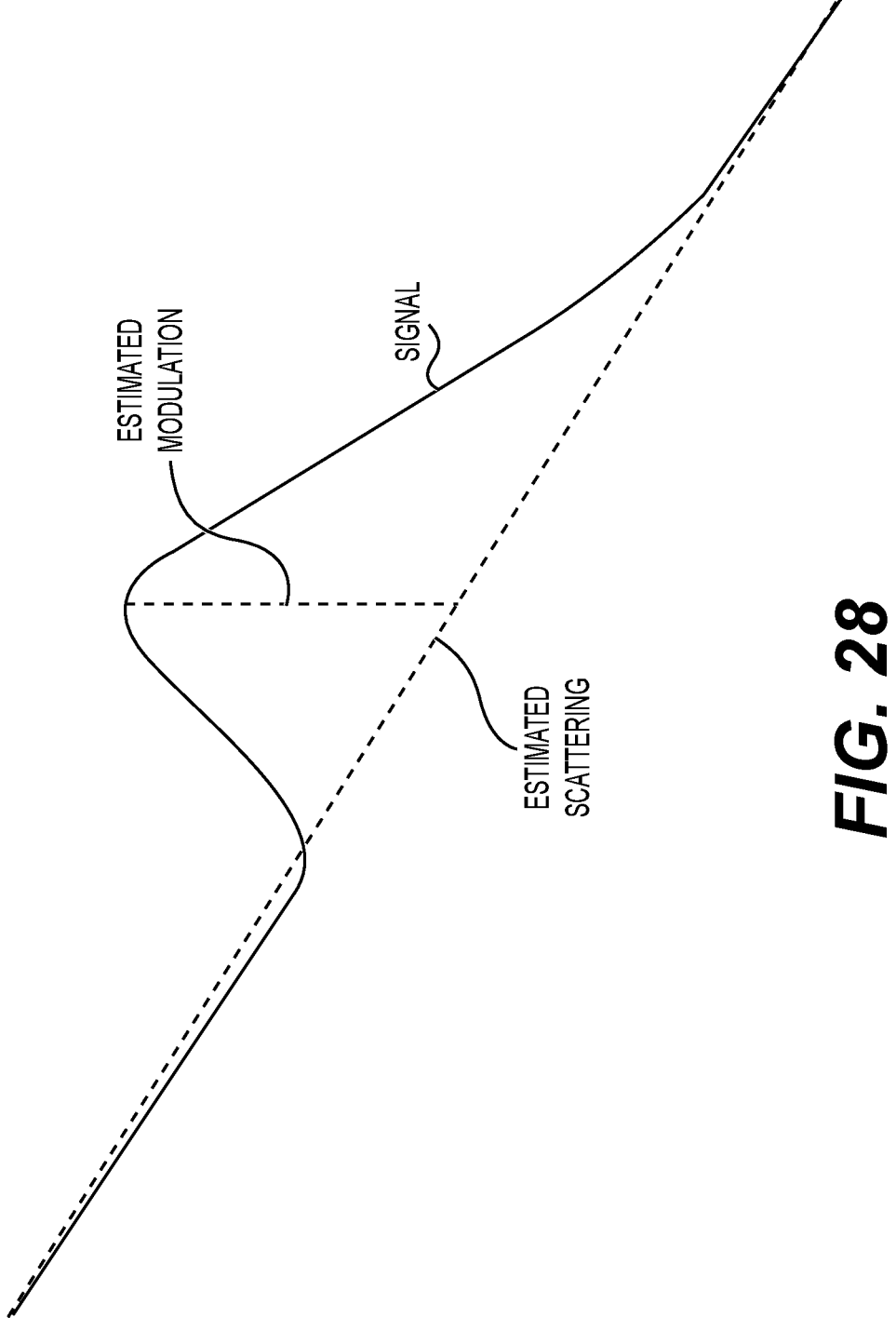
FIG. 28 exemplifies non-radiative signal extraction.

Referring to FIG. 28, additional methods of extracting signals have also been conceived which aim to provide superior PARS non-radiative signal extraction. As previously described with reference to FIG. 17, the average of a region both directly before and directly after a modulation may be used as a method of noise reduction. However, additional extensions of this concept may provide improved performance in more challenging scenarios. In particular, when the interrogation point is moving rapidly across the surface of the sample, it may be subject to additional non-PARS-based modulations due to spatial variations about the sample. In these instances, additional steps may be required to estimate the non-modulated scattering. If the method described with respect to FIG. 17 may be referred to as "step" processing, an analogous "angled-step" processing may be envisioned. Here, non-modulated scattering may be approximated by using the mean of both pre- and post-modulated regions from which the PARS amplitude and time-domain information can be extracted. More refined approaches such as partial curve fitting of specific pre- and post-modulated can also be envisioned with the same end goal.

Figure 29:
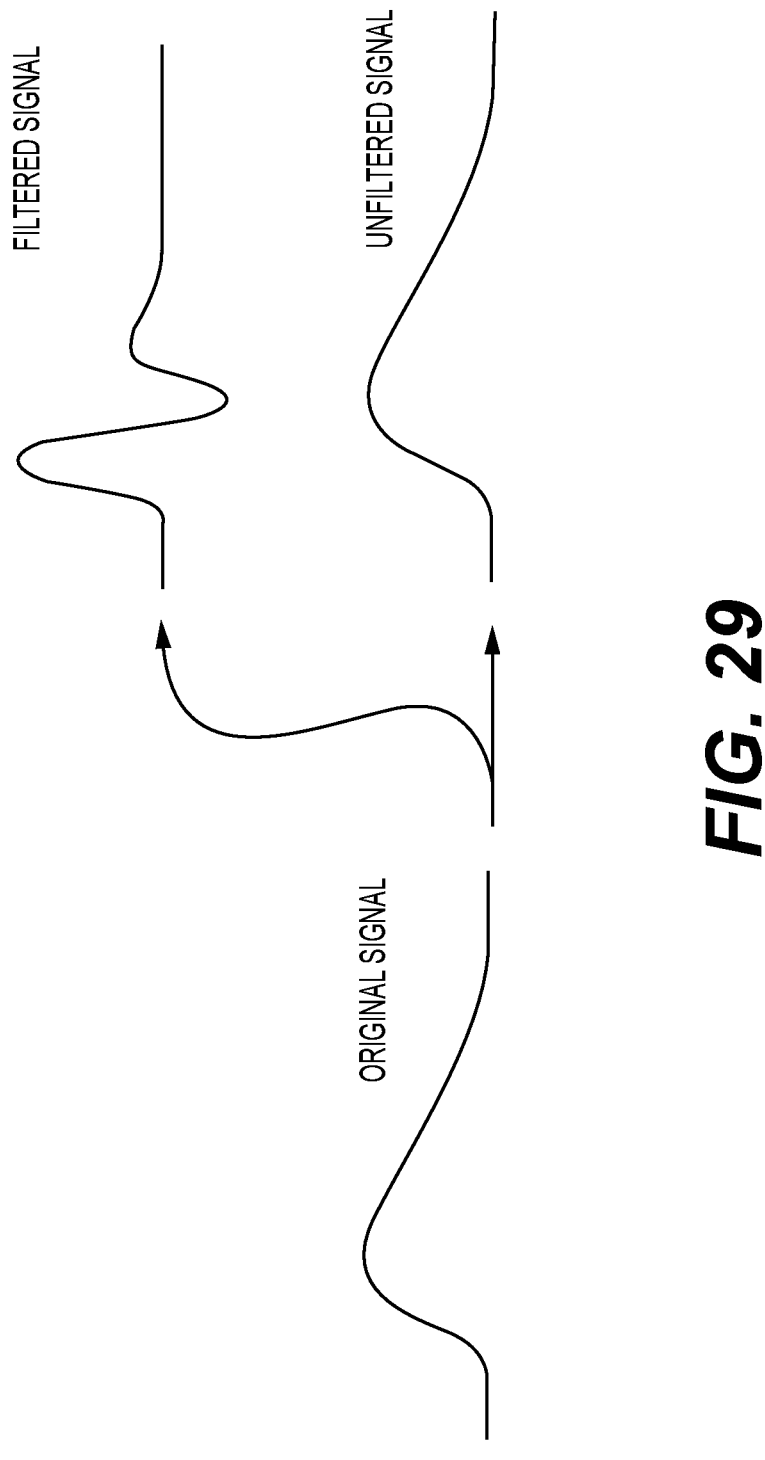
FIG. 29 exemplifies various filtered instances of a PARS signal.

Referring to FIG. 29, additional information may also be provided by recording various analog-filtered instances of a single (only one or exactly one) PARS signal. For example, a relatively unfiltered signal may be acquired alongside a highly band-passed signal by splitting the original analog signal from the photo detector and recording it on two separate channels. From these, intelligent methods such as the aforementioned K-means approach may be utilized independently on the various recorded filtered iterations. As these each represent highly independent signal measurements, additional signal fidelity may be extracted from such processes allowing for improved sensitivity.

Figure 30:
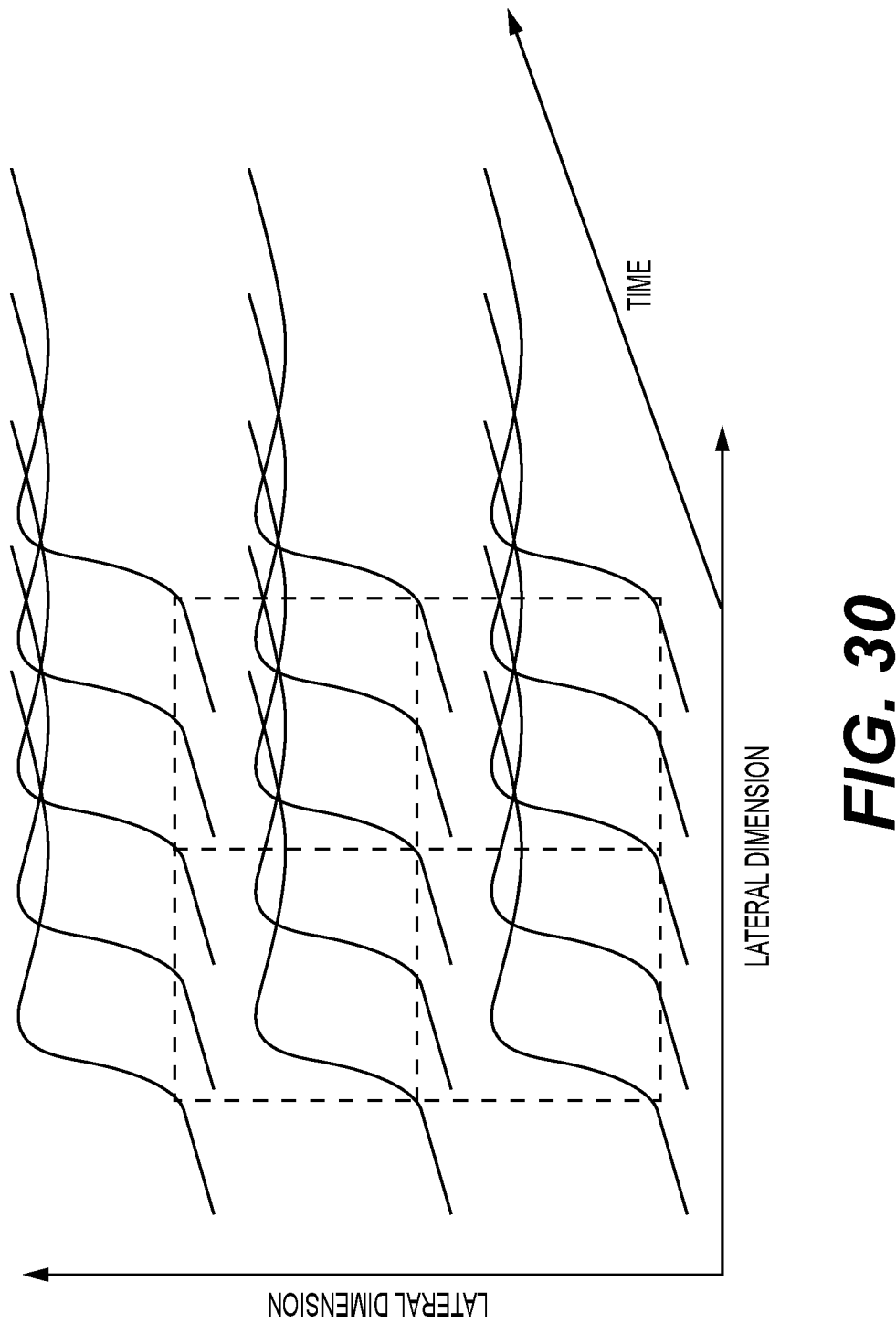
FIG. 30 exemplifies expected spatial correlation between adjacent points or signals.

Referring to FIG. 30, additional information may also be provided by taking advantage of expected spatial correlation between adjacent points. For example, a data volume may be reconstructed with the two traditional lateral image axes, along with a third axis containing each respective time-domain. This may facilitate lateral processing operations prior to time-domain signal extractions. Here, mutually dependent and mutually independent dependencies along the lateral and time axes may be leveraged to approximate a significantly lower-noise central signal. Similar non-intelligent approaches may be performed on any or all of the PARS radiative, non-radiative, and scattering channels.

Functional Extraction (from Radiative, Non-Radiative and Scattering)

As previously explained with respect to QER, properties such as the thermal diffusivity, conductivity, and speed of sound may dictate the PARS relaxation time. Features such related to temperature, speed of sound, and molecular information may be extracted from time-domain signals. As an example, two targets may have a same or similar optical absorption but slightly different other characteristics such as a different speed of sound, which may result in a different decay, evolution, and/or shape of the signals. The decay, evolution, and/or shape of the signals may be used to determine or add novel molecular information to PARS images.

Figure 31:
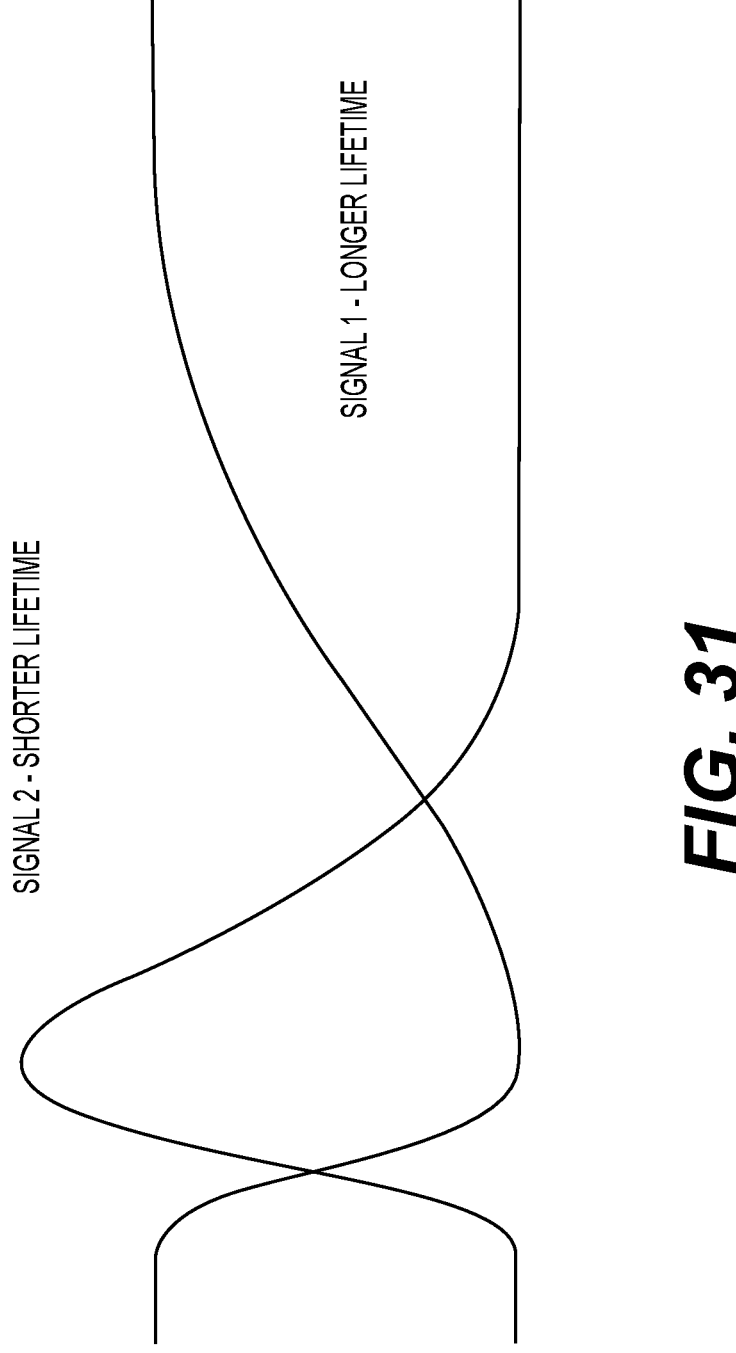
FIG. 31 exemplifies two signals with different lifetimes in connection with functional extraction.

Various optical and mechanical properties may cause these differences in signal shape. For example, the rate at which the signal returns to the background scattering level may be determined by the local thermal diffusivity. As a result, regions with, for example, higher thermal diffusivity may feature shorter signal lengths as opposed to regions with lower thermal diffusivity. This may be used to differentiate between cell nuclei and surrounding regions with similar optical absorption. Likewise, the signal lifetime may also be affected by the local speed of sound. One example may be for use in differentiating between two different metals. Aluminum and copper will feature different thermal diffusivity and speed of sound facilitating multiplexing by solely measuring signal lifetime. FIG. 31 exemplifies two signals with different lifetimes.

Post-Imaging Correction

Figure 32:
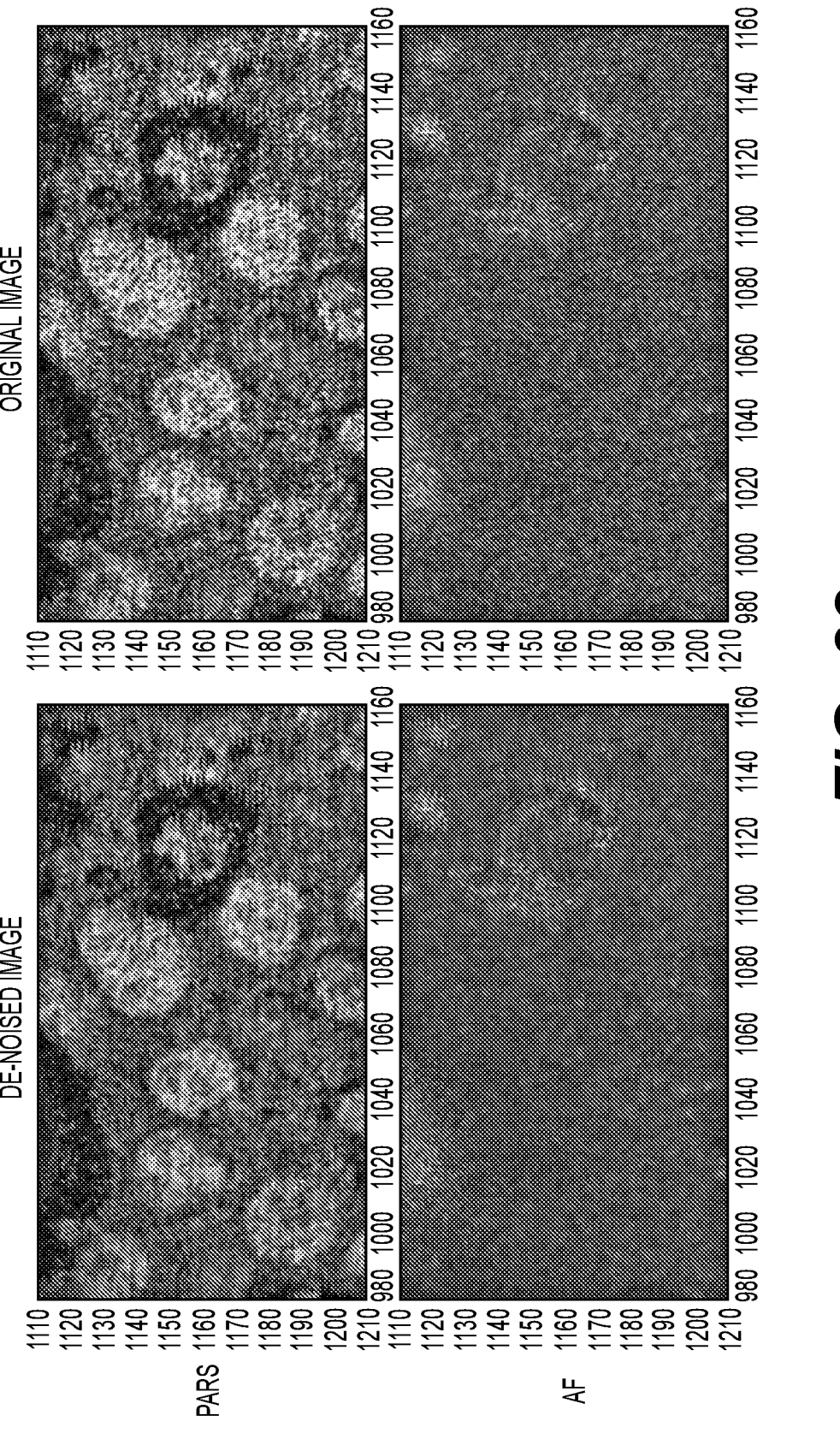
FIG. 32 shows a comparison of an original image and a denoised image.

Referring to FIG. 32, by acquiring two (or more) unique absorption-based measurements (radiative & non-radiative), local variations in these acquisitions may be used to compensate for excitation pulse energy variations. For example, two acquisitions may be compared for similar local (pixel level) variations which are near- or sub-resolution in spacing. Rapid local variations may be unlikely caused as a result of spatial variations in the sample, as it is not expected that the system would provide such level of spatial discrimination. As such, similar variations may be interpreted as similar reconstruction errors between the two visualizations. This interpretation can then be used to provide post-imaging intensity correction providing additional qualitative recovery. Although FIG. 32 shows an example of autofluorescence-based compensation, aspects disclosed herein are not limited to autofluorescence and may use other absorption-based measurements.

Chirped-Pulse PARS Acquisitions

Figure 33:
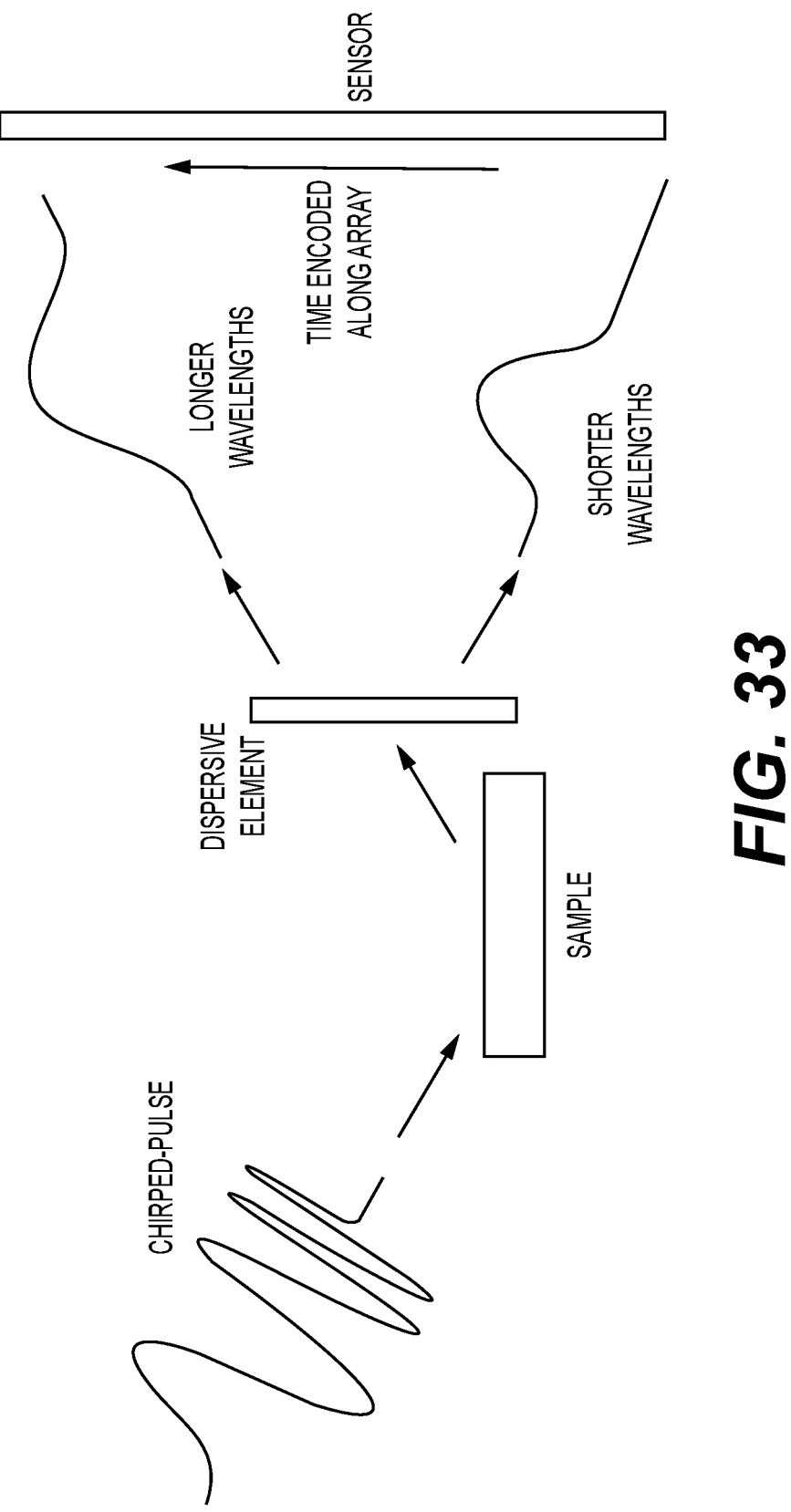
FIG. 33 shows a chirped-pulse signal and acquisition.

Referring to FIG. 33, given that PARS acquisitions are normally performed by using single photo detector elements to capture time-varying sample responses, realistic bandwidth and noise limitations in such devices may provide significant barriers towards high speed. One potential solution to this may be streak detection of PARS signals. Streak detection involves spatially separating various time-components across several detectors such as those in a linescan- or standard camera which could be accomplished in several methods.

For example, a chirped-pulse (a pulse with varying wavelength along the length of the pulse) may be used for detection, and the various wavelength components, which may now encode time information, may be spatially separated using one or more diffractive or dispersion elements such as prisms or gratings. This process may provide significant improvements in time-resolving capabilities while maintaining high signal fidelity by spreading the detection over a substantial number of detectors. Such an architecture would have clear occupations such as combining with a line-scanning architecture where detection is made over a large array such as a camera, where the two spatial coordinates of the camera now encode one spatial dimension and one temporal dimension from the sample. Other methods of streaking the time-axis across a sensor array could also be envisioned, such as the use of a high speed optical scanner.
Time Domain PARS Acquisition from Integrating Photodetector Units Many imaging sensors have a minimum integration time, which may be unable to capture the nanosecond-scale modulations in the PARS signal evolution. This can be limiting due to the potentially rich time domain information provided in the PARS signals. We propose a general strategy leveraging a rolling shutter/trigger sequence/delayed binning which would capture modulations within the integration time of these photosensors.

Figure 34:
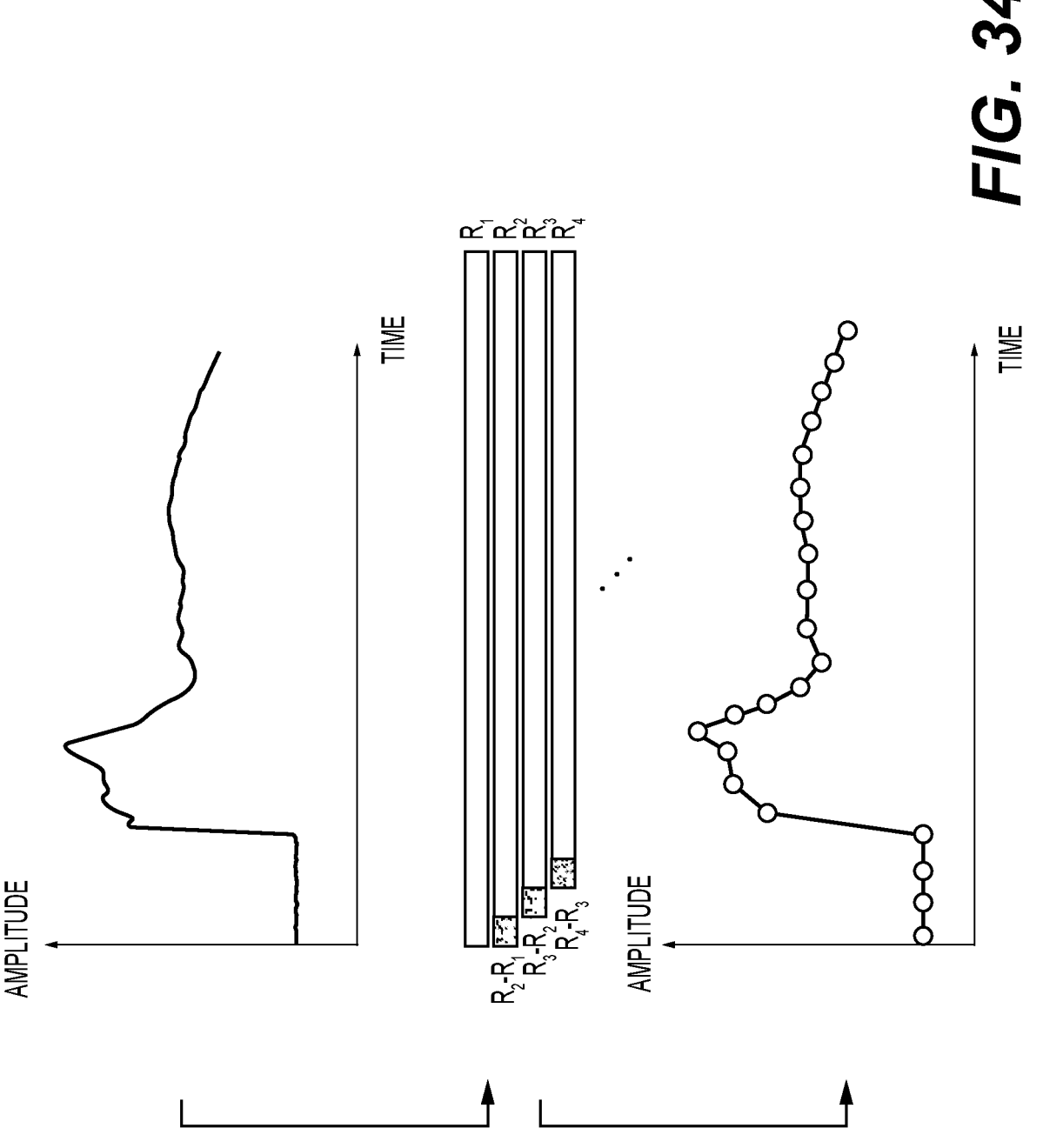
FIG. 34 shows an exemplary TD-PARS acquisition by imposing a delay to reconstruct a signal.
Figure 35:
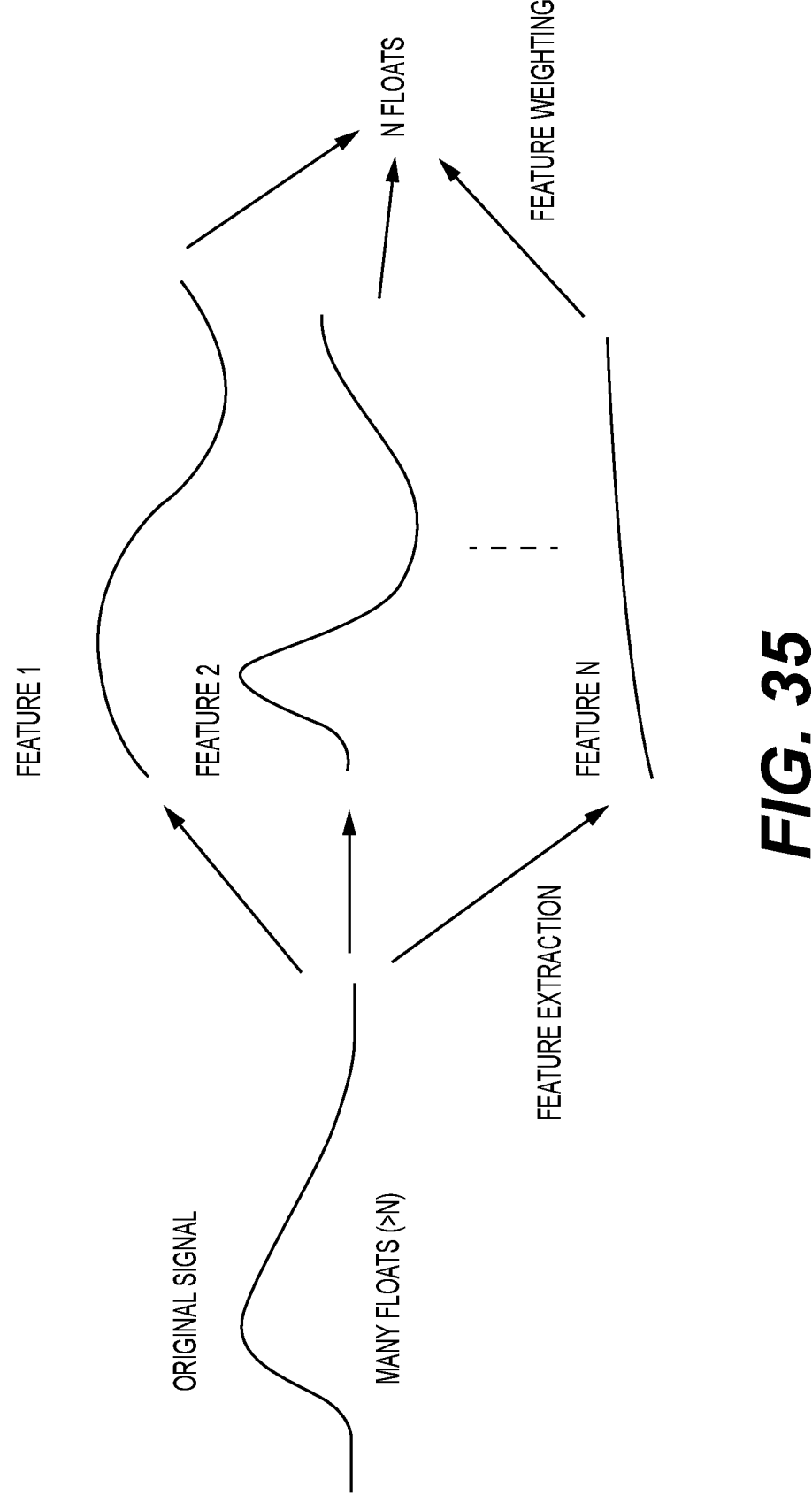
FIG. 35 shows data compression using digital and/or analog techniques.

In this PARS acquisition regime, the backscattered detection light carrying the PARS modulation may be distributed across an arrangement of integrating photo-detecting units. At the start of an acquisition, a tunable delay may be introduced between the integration start time of each photo-detecting unit (e.g., by using a rolling shutter, predetermined trigger sequence, delayed binning, and/or capturing differently timed sections of the recovered signals). If the delay time is shorter than the photo-detecting unit integration time, it is then possible to reconstruct a signal with a time resolution defined by the imposed delay. For example, PARS time domain information can be extracted by taking the derivative of these time-spaced integration windows and/or by analyzing their common regions when plotted. A visual depiction of this acquisition method is shown in FIG. 34. For example, instead of a high-sample rate photodetector, it is possible to resolve a time domain signal leveraging a CCD/CMOS camera sensor. In this case, the rows of the CCD/CMOS camera are the photo-detecting units which capture the signal in a rolling shutter fashion. With the imposed delay between individual photodetector lines, a PARS time domain signal can be constructed with a time resolution greater than a single integrating sensor.
Data Compression Referring to FIG. 35, data may be compressed using digital and/or analog techniques. For example, with the K-means approach, raw time-domain signals may be appropriately represented by their respective K-means weights. If, for example, three such prototypes were in use on a particular dataset, rather than storing full time domains (~200+ samples), the time-axis may be well compressed to simply three values or floats. Similar such extracted features may be used in lieu of full non-compressed time domains for the purposes of decreased system RAM usage, reduced data bandwidth requirements, reduced systems storage loads, etc.
Fast Acquisition Approaches Acquiring at higher interrogation rates may necessitate more elaborate acquisition processes. A variety of issues may arise while interrogating the sample at higher acquisition rates including logistical movement of the interrogation spot about the sample and higher frequency optical scattering signals. Fast lateral motion of the interrogation spot about the sample may be performed through hybrid scanning approaches combining both fast optical scanning methods such as resonant scanners and polygon scanners alongside bulk scanning approaches such as mechanical scanning stages. Such methods in other optical microscopy approaches have facilitated interrogation rates in the 10 s of MHz and may provide similar benefits to PARS modalities.

Figure 36:
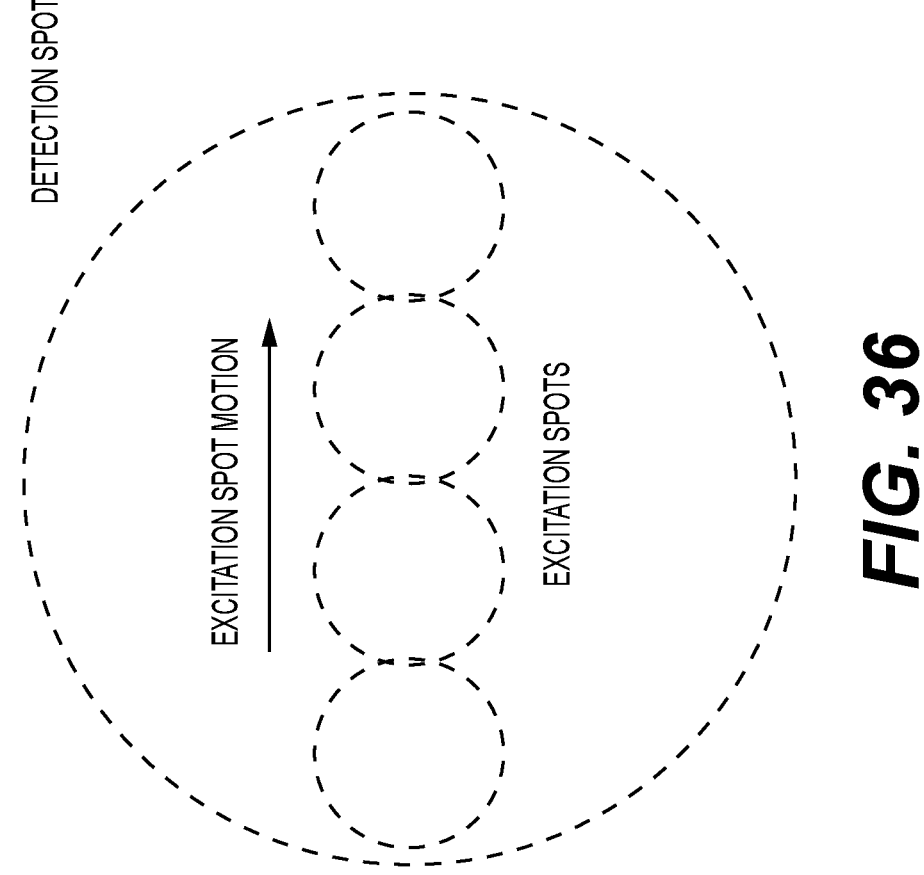
FIG. 36 shows an exemplary fast acquisition approach.

However, such fast motion of the interrogation spot about the sample may also induce additional undesired scattering frequency content which may confound time-domain signal processing of the collected PARS signals. As such, as shown in FIG. 36, it may be beneficial to operate the detection focal spot on the sample at a larger size relative to the excitation spot such that the excitation spot may be scanned about a relatively stationary, or slower moving detection spot reducing the effects of rapid optical scanning of the detection.
Data Colorizing Referring to FIG. 37, techniques and methods disclosed herein may allow a direct construction of a colorized H&E simulated image, bypassing a grayscale or scalar-amplitude based reconstruction. The colors used may emulate those traditionally used in H&E stains, such as various shades of pink, purple, and/or blue. However, aspects disclosed herein are not limited to pink, purple, and/or blue colors, and systems and processors may be configured to use other colors. For example, red, green, and blue color channels may be used to represent three extracted K-means prototypes.
Augmented Reality Interface Upon completing processing of data visualizations or images, these visualizations may be displayed in combination with and/or overlaid with other visualizations on a user interface screen. For example, a low-resolution bright field image of the sample may form the background of the presented PARS visualizations. Such augmentations may be used to help maintain orientation between the required visualizations and the original sample.
Applications Aspects disclosed herein may include non-radiative (heat and pressure) and radiative (fluorescence is one of the possible signals) signals in a sample. Aspects disclosed herein may include collecting radiative relaxation and non-radiative relaxation due to optical absorption and also scattering from both excitation and detection. The collected signals and/or raw data may be used to directly form and color an image of a sample, such as an H&E (hematoxylin and eosin) histology image without staining the sample. H&E histology images may be directly formed and colorized by using methods (such as based on a comparison of non-radiative and radiative signals, QER, lifetime or evolution of signals, and/or a clustering algorithm) disclosed herein and using features in raw PARS signals. Aspects disclosed herein may be used to determine or measure, using a photoabsorption remote sensing system or PARS, mechanical characteristics such as the speed of sound and/or temperature characteristics of the sample. A tiny or pinpointed area of the sample (e.g., a size of a focused laser beam or beam of light) may be used to measure these features or characteristics. Aspects disclosed herein may extract more than just an amplitude or scalar amplitude of signals in a sample. For example, two targets may have a same or similar optical absorption but slightly different other characteristics such as a different speed of sound, which may result in a different evolution and/or shape of the signals.

Aspects disclosed herein may be used to determine or add novel molecular information to PARS images.

It will be apparent that other examples may be designed with different fiber-based or free-space components to achieve similar results. Other alternatives may include various coherence length sources, use of balanced photodetectors, interrogation-beam modulation, incorporation of optical amplifiers in the return signal path, etc.

During in vivo imaging experiments, no agent or ultrasound coupling medium are required. However, the target can be prepared with water or any liquid such as oil before a non-contact imaging session. As well, in some instances an intermediate window such as a cover slip or glass window may be placed between the imaging system and the sample.

Aspects disclosed herein may use a combination of a PARS device alongside an optical coherence tomography (OCT). OCT is a complementary imaging modality to PARS devices. OCT measurements can be performed using various approaches, either in the time domain optical coherence tomography (TD-OCT) or in frequency domain optical coherence tomography (FD-OCT) as described in US 2010/0265511 and US2014/0125952. In OCT systems, multiple A-scans are typically acquired while the sample beam is scanned laterally across the tissue surface, building up a two-dimensional map of reflectivity versus depth and lateral extent typically called a B-scan. The lateral resolution of the B-scan is approximated by the confocal resolving power of the sample arm optical system, which is usually given by the size of the focused optical spot in the tissue.

All optical sources including but not limited to PARS excitations, PARS detections, PARS signal enhancements, and OCT sources may be implemented as continuous beams, modulated continuous beams, or short pulsed lasers in which pulse widths may range from attoseconds to milliseconds. These may be set to any wavelength suitable for taking advantage of optical (or other electromagnetic) properties of the sample, such as scattering and absorption. Wavelengths may also be selected to purposefully enhance or suppress detection or excitation photons from different absorbers. Wavelengths may range from nanometer to micron scales. Continuous-wave beam powers may be set to any suitable power range such as from attowatts to watts. Pulsed sources may use pulse energies appropriate for the specific sample under test such as within the range from attojoules to joules. Various coherence lengths may be implemented to take advantage of interferometric effects. These coherence lengths may range from nanometers to kilometers. As well, pulsed sources may use any repetition rate deemed appropriate for the sample under test such as from continuous-wave to the gigahertz regime. The sources may be tunable, monochromatic or polychromatic.

The TA-PARS, MP-PARS, Multi-Photon Excitation PARS, QER, lifetime PARS, and TD-PARS subsystems may include an interferometer, such as a Michelson interferometer, Fizeau interferometer, Ramsey interferometer, Fabry-Perot interferometer, Mach-Zehnder interferometer, or optical-quadrature detection. Interferometers may be free-space or fiber-based or some combination. The basic principle is that phase and amplitude oscillations in the probing receiver beam can be detected using interferometry and detected at AC, RF or ultrasonic frequencies using various detectors.

The TA-PARS, MP-PARS, Multi-Photon Excitation PARS, QER, lifetime PARS, and TD-PARS subsystems may use and implement a non-interferometry detection design to detect amplitude modulation within the signal. The non-interferometry detection system may be free-space or fiber-based or some combination therein.

The TA-PARS, MP-PARS, Multi-Photon Excitation PARS, QER, lifetime PARS, and TD-PARS subsystems may use a variety of optical fibers such as photonic crystal fibers, image guide fibers, double-clad fibers etc.

The PARS subsystems may be implemented as a conventional photoacoustic remote sensing system, non-interferometric photoacoustic remote sensing (NI-PARS), camera-based photoacoustic remote sensing (C-PARS), coherence-gated photoacoustic remote sensing (CG-PARS), single-source photoacoustic remote sensing (SS-PARS), or extensions thereof.

In one example, all beams may be combined and scanned. In this way, PARS excitations may be sensed in the same area as they are generated and where they are the largest. OCT detection may also be performed in the same location as the PARS to aid in registration. Other arrangements may also be used, including keeping one or more of the beams fixed while scanning the others or vice versa. Optical scanning may be performed by galvanometer mirrors, MEMS mirrors, polygon scanners, stepper/DC motors, etc. Mechanical scanning of the sample may be performed by stepper stages, DC motor stages, linear drive stages, piezo drive stages, piezo stages, etc.

Both the optical scanning and mechanical scanning approaches may be leveraged to produce one-dimensional, two-dimensional, or three-dimensional scans about the sample. Adaptive optics such as TAG lenses and deformable mirrors may be used to perform axial scanning within the sample. Both optical scanning and mechanical scanning may be combined to form a hybrid scanner. This hybrid scanner may employ one-axis or two-axis optical scanning to capture large areas or strips in a short amount of time. The mirrors can potentially be controlled using custom control hardware to have customized scan patterns to increase scanning efficiency in terms of speed and quality. For example, one optical axis can be used to scan rapidly and simultaneously one mechanical axis can be used to move the sample. This may render a ramp-like scan pattern which can then be interpolated. Another example, using custom control hardware, would be to step the mechanical stage only when the fast-axis has finished moving yielding a cartesian-like grid which may not need any interpolation.

PARS may provide 3D imaging by optical or mechanical scanning of the beams or mechanical scanning of the samples or the imaging head or the combination of mechanical and optical scanning of the beams, optics, and the samples. This may allow rapid structural and function enface or 3D imaging.

One or multiple pinholes may be employed to reject out of focus light when optically or mechanically scanning the beams or mechanical scanning of the samples or the imaging head or the combination of mechanical and optical scanning of the beams, optics, and samples. They may improve the signal to noise ratio of the resulting images.

Beam combiners may be implemented using dichroic mirrors, prisms, beamsplitters, polarizing beamsplitters, WDMs etc.

Beam paths may be focused on to the sample using different optical paths. Each of the single or multiple PARS excitation, detection, signal enhancement etc. paths and OCT paths may use an independent focusing element onto the sample, or all share a single (only one or exactly one) path or any combination. Beam paths may return from the sample using unique optical paths which are different from those optical paths used to focus on to the sample. These unique optical paths may interact with the sample at normal incidence, or may interact at some angle where the central beam axis forms an angle with the sample surface ranging from 5 degrees to 90 degrees.

For some applications such as in ophthalmic imaging, the imaging head may not implement any primary focusing element such as an objective lens to tightly focus the light onto the sample. Instead, the beams may be collimated, or loosely focused (as to create a spot size much larger than the optical diffraction limit) while being directed at the sample. For example, ophthalmic imaging devices made direct a collimated beam into the eye allowing the eye's lens to focus the beam on to the retina.

The imaging head may focus the beams into the sample at least to a depth of 50 nm. The imaging head may focus the beams into the sample at most to a depth of 10 mm. The added depth over previous PARS arises from the novel use of deeply-penetrating detection wavelengths as described above.

Light may be amplified by an optical amplifier prior to interacting with a sample or prior to detection. Light may be collected by photodiodes, avalanche photodiodes, photo-tubes, photomultipliers, CMOS cameras, CCD cameras (including EM-CCD, intensified-CCDs, back-thinned and cooled CCDs), spectrometers, etc. The detected signals may be amplified by an RF amplifier, lock-in amplifier, trans-impedance amplifier, or other amplifier configuration.

Modalities may be used for A-, B- or C-scan images for in vivo, ex vivo or phantom studies. The TA-PARS, MP-PARS, Multi-Photon Excitation PARS, QER, lifetime PARS, and TD-PARS subsystems may take the form of any embodiment common to microscopic and biological imaging techniques. Some of these may include but are not limited to devices implemented as a table-top microscope, inverted microscope, handheld microscope, surgical microscope, endoscope, or ophthalmic device, etc. These may be constructed based on principles known in the art.

The TA-PARS, MP-PARS, Multi-Photon Excitation PARS, QER, lifetime PARS, and TD-PARS subsystems may be optimized in order to take advantage of a multi-focus design for improving the depth-of-focus of 2D and 3D imaging. The chromatic aberration in the collimating and objective lens pair may be harnessed to refocus light from a fiber into the object so that each wavelength is focused at a slightly different depth location. These chromatic aberrations may be used to encode depth information into the recovered PARS signals which may be later recovered using wavelength specific analysis approaches. Using these wavelengths simultaneously may also be used to improve the depth of field and signal to noise ratio (SNR) of the PARS images. During imaging, depth scanning by wavelength tuning may be performed.

PARS methods may provide lateral or axial discrimination on the sample by spatially encoding detection regions, such as by using several pinholes, or by the spectral content of a broadband beam.

The TA-PARS, MP-PARS, Multi-Photon Excitation PARS, QER, lifetime PARS, and TD-PARS subsystems may be combined with other imaging modalities such as stimulated Raman microscopy, fluorescence microscopy, two-photon and confocal fluorescence microscopy, Coherent-Anti-Raman-Stokes microscopy, Raman microscopy, other photoacoustic and ultrasound systems, etc. This could permit imaging of the microcirculation, blood oxygenation parameter imaging, and imaging of other molecularly-specific targets simultaneously, a potentially important task that is difficult to implement. A multi-wavelength visible laser source may also be implemented to generate photoabsorption signals for functional or structural imaging.

Polarization analyzers may be used to decompose detected light into respective polarization states. The light detected in each polarization state may provide information about the sample. Phase analyzers may be used to decompose detected light into phase components. This may provide information about the sample.

The TA-PARS, MP-PARS, Multi-Photon Excitation PARS, QER, lifetime PARS, and TD-PARS subsystems may detect generated signals in the detection beam(s) returning from the sample. These perturbations may include but are not limited to changes in intensity, polarization, frequency, phase, absorption, nonlinear scattering, and nonlinear absorption and could be brought on by a variety of factors such as pressure, thermal effects, etc.

Analog-based signal extraction may be performed along electrical signal pathways. Some examples of such analog devices may include but are not limited to lock-in amplifiers, peak-detections circuits, etc.

The PARS subsystem may detect temporal information encoded in the back-reflected detection beam. This information may be used to discriminate chromophores, enhance contrast, improve signal extraction, etc. This temporal information may be extracted using analog and digital processing techniques. These may include but are not limited to the use of lock-in amplifiers, Fourier transforms, wavelet transforms, intelligent algorithm extraction to name a few. In one example, lock in detection may be leveraged to extract PARS signals which are similar to known expected signals for extraction of particular chromophores such as DNA, cytochromes, red blood cells, etc.

The imaging head of the system may include close-loop or open-loop adaptive optic components including but not limited to wave-front sensors, deformable mirrors, TAG lenses, etc. for wave-front and aberration correction. Aberrations may include de-focus, astigmatism, coma, distortion, 3rd-order effects, etc. The signal enhancement beam may also be used to suppress signals from undesired chromophores by purposely inducing a saturation effect such as photobleaching.

Various types of optics may be utilized to leverage their respective advantages. For example, axicons may be used as a primary objective to produce Bessel beams with a larger depth of focus as compared to that available by standard gaussian beam optics. Such optics may also be used in other locations within beam paths as deemed appropriate. Reflective optics may also take the place of their respective refractive elements, such as the use of a reflective objective lens rather than a standard compound objective lens.

Optical pathways may include nonlinear optical elements for various related purposes such as wavelength generation and wavelength shifting. Beam foci may overlap at the sample but may also be laterally and axially offset from each other when appropriate by a small amount.

The TA-PARS, MP-PARS, Multi-Photon Excitation PARS, QER, lifetime PARS, and TD-PARS subsystems may be used as a spectrometer for sample analysis.

Other advantages that are inherent to the structure will be apparent to those skilled in the art. The embodiments described herein are illustrative and not intended to limit the scope of the claims, which are to be interpreted in light of the specification as a whole.

Applications

It will be understood that the system described herein may be used in various ways, such as those purposes described in the prior art, and also may be used in other ways to take advantage of the aspects described above. A non-exhaustive list of applications are discussed below.

The system may be used for imaging angiogenesis for different pre-clinical tumor models.

The system may be used for unmixing targets (e.g. detect, separate or otherwise discretize constituent species and/or subspecies) based on their absorption, scattering or frequency contents by taking advantage of different wavelengths, different pulse widths, different coherence lengths, repetition rates, exposure time, different evolution or lifetime of signals, quantum efficiency ratio and/or other comparisons of non-radiative and radiative signals, etc.

The system may be used to image with resolution up to and exceeding the diffraction limit.

The system may be used to image anything that absorbs light, including exogenous and endogenous targets and biomarkers.

The system may have some surgical applications, such as functional and structural imaging during brain surgery, use for assessment of internal bleeding and cauterization verification, imaging perfusion sufficiency of organs and organ transplants, imaging angiogenesis around islet transplants, imaging of skin-grafts, imaging of tissue scaffolds and biomaterials to evaluate vascularization and immune rejection, imaging to aid microsurgery, guidance to avoid cutting critical blood vessels and nerves.

The system may also have some gastroenterological applications, such as imaging vascular beds and depth of invasion in Barrett's esophagus and colorectal cancers. Depth of invasion, in at least some embodiments, is key to prognosis and metabolic potential. This may be used for virtual biopsy, crohn's diseases, monitoring of IBS, inspection of carotid artery. Gastroenterological applications may be combined or piggy-backed off of a clinical endoscope and the miniaturized PARS system may be designed either as a standalone endoscope or fit within the accessory channel of a clinical endoscope.

The system may also be used for clinical imaging of micro- and macro-circulation and pigmented cells, which may find use for applications such as in (1) the eye, potentially augmenting or replacing fluorescein angiography: (2) imaging dermatological lesions including melanoma, basal cell carcinoma, hemangioma, psoriasis, eczema, dermatitis, imaging Mohs surgery, imaging to verify tumor margin resections: (3) peripheral vascular disease: (4) diabetic and pressure ulcers: (5) burn imaging: (6) plastic surgery and microsurgery: (7) imaging of circulating tumor cells, especially melanoma cells: (8) imaging lymph node angiogenesis: (9) imaging response to photodynamic therapies including those with vascular ablative mechanisms: (10) imaging response to chemotherapeutics including anti-angiogenic drugs: (11) imaging response to radiotherapy.

The system may also be used for some histopathology imaging applications, such as frozen pathology, creating H&E-like images from tissue samples, virtual biopsy, etc. It may be used on various tissue preparations such as formalin-fixed paraffin-embedded tissue blocks, formalin-fixed paraffin-embedded tissue slides, frozen pathology sections, freshly resected specimen, etc. Within these samples visualization of macromolecules such as DNA, RNA, cytochromes, lipids, proteins, etc. may be performed.

The system may be useful in estimating oxygen saturation using multi-wavelength PARS excitation in applications including: (1) estimating venous oxygen saturation where pulse oximetry cannot be used including estimating cerebrovenous oxygen saturation and central venous oxygen saturation. This could potentially replace catheterization procedures which can be risky, especially in small children and infants.

Oxygen flux and oxygen consumption may also be estimated by using PARS imaging to estimate oxygen saturation, and to estimate blood flow in vessels flowing into and out of a region of tissue.

The system may be useful in separating salient histological chromophores such as cell nuclei and the surrounding cytoplasm by leveraging their respective absorption spectra.

The systems may be used for unmixing targets using their absorption contents, scattering, phase, polarization or frequency contents by taking advantage of different wavelengths, different pulse widths, different coherence lengths, repetition rates, fluence, exposure time, etc.

Other examples of applications may include imaging of contrast agents in clinical or pre-clinical applications: identification of sentinel lymph nodes: non- or minimally-invasive identification of tumors in lymph nodes: non-destructive testing of materials: imaging of genetically-encoded reporters such as tyrosinase, chromoproteins, fluorescent proteins for pre-clinical or clinical molecular imaging applications: imaging actively or passively targeted optically absorbing nanoparticles for molecular imaging; and imaging of blood clots and potentially staging the age of the clots.

Other examples of applications may include clinical and pre-clinical ophthalmic applications: oxygen saturation measurement and retinal metabolic rate in diseases such as age related macular degeneration, diabetic retinopathy and glaucoma, limbal vasculature and stem cells imaging, corneal nerve and neovascularization imaging, evaluating Schlemm canal changes in glaucoma patients, choroidal neovascularization imaging, anterior and posterior segments blood flow imaging and blood flow state.

The system may be used for measurement and estimation of metabolism within a biological sample leveraging the capabilities of both PARS and OCT. In this example the OCT may be used to estimate volumetric blood flow within a region of interest, and the PARS systems may be used to measure oxygen saturation within blood vessels of interest. The combination of these measurements then may provide estimation of metabolism within the region.

The system may be used for head and neck cancer types and skin cancer types, functional brain activities, Inspecting stroke patient's vasculature to help locate clots, monitoring changes in neuronal and brain function/development as a result of changing gut bacteria composition, atherosclerotic plaques, monitoring oxygen sufficiency following flap reconstruction, profusion sufficiency following plastic or cosmetic surgery and imaging the cosmetic injectables.

The system may be used for topology tracking of surface deformations. For example, the OCT may be used to track the location of the sample surface. Then corrections may be applied to a tightly focused PARS device using mechanisms such as adaptive optics to maintain alignment to that surface as scanning proceeds.

The system may be implemented in various different form factors appropriate to these applications such as a tabletop microscope, inverted microscope, handheld microscope, surgical microscope, ophthalmic microscope, endoscope, etc.

Aspects disclosed herein may be used with the following applications: imaging histological samples: imaging cell nuclei: imaging proteins: imaging DNA: imaging RNA; imaging lipids: imaging of blood oxygen saturation: imaging of tumor hypoxia: imaging of wound healing, burn diagnostics, or surgery; imaging of microcirculation; blood oxygenation parameter imaging; estimating blood flow in vessels flowing into and out of a region of tissue; imaging of molecularly-specific targets; imaging angiogenesis for preclinical tumor models; clinical imaging of micro- and macro-circulation and pigmented cells; imaging of the eye; augmenting or replacing fluorescein angiography; imaging dermatological lesions; imaging melanoma; imaging basal cell carcinoma; imaging hemangioma; imaging psoriasis; imaging eczema; imaging dermatitis; imaging Mohs surgery; imaging to verify tumor margin resections; imaging peripheral vascular disease; imaging diabetic and/or pressure ulcers; burn imaging; plastic surgery; microsurgery; imaging of circulating tumor cells; imaging melanoma cells; imaging lymph node angiogenesis; imaging response to photodynamic therapies; imaging response to photodynamic therapies having vascular ablative mechanisms; imaging response to chemotherapeutics; imaging frozen pathology samples; imaging paraffin embedded tissues; imaging H&E-like images; imaging oxygen metabolic changes; imaging response to anti-angiogenic drugs; imaging response to radiotherapy; estimating oxygen saturation using multi-wavelength PARS excitation; estimating venous oxygen saturation where pulse oximetry cannot be used; estimating cerebrovenous oxygen saturation and/or central venous oxygen saturation; estimating oxygen flux and/or oxygen consumption; imaging vascular beds and depth of invasion in Barrett's esophagus and/or colorectal cancers; functional and structural imaging during brain surgery; assessment of internal bleeding and/or cauterization verification; imaging perfusion sufficiency of organs and/or organ transplants; imaging angiogenesis around islet transplants; imaging of skin-grafts; imaging of tissue scaffolds and/or biomaterials to evaluate vascularization and/or immune rejection; imaging to aid microsurgery; guidance to avoid cutting blood vessels and/or nerves; imaging of contrast agents in clinical or pre-clinical applications; identification of sentinel lymph nodes; non- or minimally-invasive identification of tumors in lymph nodes; non-destructive testing of materials; imaging of genetically-encoded reporters, wherein the genetically-encoded reporters include tyrosinase, chromoproteins, and/or fluorescent proteins for pre-clinical or clinical molecular imaging applications; imaging actively or passively targeted optically absorbing nanoparticles for molecular imaging; imaging of blood clots; staging an age of blood clots; remote or non-invasive intratumoural assessment of glucose concentration by detection of endogenous glucose absorption peeks; assessment of organoid growth; monitoring of developing embryos; assessment of biofilm composition; assessment of tooth decay; assessment of non-living structures; evaluating the composition of paintings for non-invasive confirmation of authenticity; evaluation of archeological artifacts; manufacturing quality control; manufacturing quality assurance; replacing a catheterization procedure; gastroenterological applications; single-excitation pulse imaging over an entire field of view; imaging of tissue; imaging of cells; imaging of scattered light from object surfaces; imaging of absorption-induced changes of scattered light; or non-contact imaging of optical absorption.

Aspects disclosed herein may provide a computer-implemented method of visualizing features in a sample. The method may include receiving one or more photoabsorption remote sensing or system (PARS) signals, clustering the received one or more PARS signals using a clustering algorithm to determine features of the sample, and determining an image based on the clustered PARS signals. Alternatively or in addition thereto, the method may include determining a ratio of non-radiative signals to radiative signals, determining a value that is a function of non-radiative signals and radiative signals, and/or comparing non-radiative signals, radiative signals, and/or scattering signals, and determining the image, including colors, based on the determined ratio, value, and/or comparison.

The PARS signals may be collected by generating signals in the sample at an excitation location using an excitation beam, the excitation beam being focused below a surface of the sample, interrogating the sample with an interrogation beam directed toward the excitation location of the sample, the interrogation beam being focused below the surface of the sample, and detecting a portion of the interrogation beam returning from the sample. Generating signals may include generating pressure, temperature, and fluorescence (and/or other radiative and/or non-radiative signals). The returned portion of the interrogation beam may be indicative of the generated pressure and temperature signals. The PARS signals are further collected by detecting fluorescence signals from the excitation location of the sample while detecting the generated pressure and temperature signals. The PARS signals may be further collected by redirecting a portion of the returned interrogation beam and detecting an interaction with the sample.

A wavelength of the excitation beam may be configured such that the sample absorbs two or more photons simultaneously, wherein a sum of energy of the two or more photons may be equal to a predetermined energy. The method may include collecting the PARS signals.

Clustering the received PARS signals may be based on shape. The method may not include analyzing a reconstructed grayscale image to determine the image. Clustering the received PARS signals may not be based on a scalar amplitude. The method may not include mapping or visualizing a scalar amplitude. The PARS signals may be indicative of temperature characteristics of the sample. The PARS signals may be indicative of a speed of sound in the sample. The PARS signals may be indicative of molecular information. The PARS signals may be indicative of characteristics in the sample in an area having a size defined by a focused beam of light. Receiving the PARS signals may include receiving time domain (TD) signals.

The method may include determining cluster centroids based on the clustered PARS signals. The determined cluster centroids may include characteristic time-domain signals. Receiving the PARS signals may include receiving backscattering intensity, radiative signals, and non-radiative relaxation time-domain signals.

Receiving the PARS signals may include receiving radiative PARS signals and non-radiative PARS signals. The method may further include determining a ratio of and/or value based on the radiative PARS signals and the non-radiative PARS signals. The ratio and/or value may be plotted against quantum efficiency (QE) values. The method may include determining an image and/or biomolecular information based on the ratio and/or value.

The method may include determining a decay or evolution time based on the received PARS signals. Determining the image may include determining one or more colors based on the clustering. The method may include displaying the image on a display.

Systems and techniques disclosed herein may provide a photoabsorption remote sensing (PARS) system for imaging features in a sample. The system may include an excitation light source configured to generate signals in the sample at an excitation location, the excitation light source being focused below a surface of the sample, an interrogation light source configured to interrogate the sample and directed toward the excitation location of the sample, the interrogation light source being focused below the surface of the sample, a portion of the at least one interrogation light source returning from the sample that is indicative of the generated signals, and a processor configured to execute a clustering algorithm to cluster the generated signals and determine an image based on the clustered generated signals, the image being indicative of features in the sample. The system may include a display configured to display the determined image. The image may be formed directly from the received signals.

The processor may be configured to determine one or more colors based on the clustering. The determined colors may include purple, blue, and pink such that the image is configured to resemble an hematoxylin and eosin (H&E) stained image.

Systems and techniques disclosed herein may provide a computer-implemented method of visualizing features in a sample. The method may include receiving one or more signals, clustering the received signals based on shape using a clustering algorithm to determine time-domain features of the sample, and determining an image, including one or more colors used in the image, based on the clustered signals and determined time-domain features.

The method may include determining vector angles from the received one or more signals. Clustering the received signals based on shape may include clustering the received signals based on the vector angles. The one or more signals may include at least one of non-radiative signals or radiative signals. The one or more signals may include at least one of non-radiative heat signals or non-radiative pressure signals. The one or more signals may include radiative fluorescence signals. The radiative fluorescence signals may be radiative autofluorescence signals. The non-radiative and radiative signals may include pressure signals, temperature signals, ultrasound signals, autofluorescence signals, nonlinear scattering, and/or nonlinear fluorescence signals.

Aspects disclosed herein may provide a computer-implemented method of visualizing features in a sample. The method may include receiving signals, the signals including non-radiative and radiative signals from the sample, clustering the received one or more signals using a clustering algorithm to determine features of the sample, and determining an image based on the clustered signals. The non-radiative signals may include heat signals and pressure signals, and the radiative signals may include fluorescence signals. The entire non-radiative and radiative relaxations may be received, such as pressure signals, temperature signals, ultrasound signals, autofluorescence signals, nonlinear scattering, and nonlinear fluorescence.

At least some of the signals are collected by generating signals in the sample at an excitation location using an excitation beam, interrogating the sample with an interrogation beam directed toward the excitation location of the sample, and detecting a portion of the interrogation beam returning from the sample. At least some of the signals may be collected by detecting optical absorption and scattering from the sample. The optical absorption and scattering may occur from excitation and detection of the sample.

Aspects disclosed herein may provide a method of visualizing features in a sample. The method may include receiving one or more signals, clustering the received signals based on shape using a clustering algorithm to determine features of the sample, the shape being based on a vector, and determining an image, including one or more colors used in the image, based on the clustered signals and determined features.

The invention claimed is:

1. A method of visualizing details in a sample, comprising:
   generating radiative and non-radiative signals in the sample at an excitation location using an excitation beam, the excitation beam being focused below a surface of the sample;
   interrogating the sample with an interrogation beam directed toward the excitation location of the sample, the interrogation beam being focused below the surface of the sample;
   detecting light from the sample, the detected light including a portion of the interrogation beam returning from the sample, wherein the detected light is indicative of the generated radiative and the non-radiative signals; and
   determining a value using a function based on the detected generated radiative signals and the non-radiative signals.

2. The method of claim 1, wherein the returned portion of the interrogation beam is indicative of the generated non-radiative signals, and a portion of the detected light that excludes the returned portion of the interrogation beam and the excitation beam is indicative of the generated radiative signals.

3. The method of claim 1, further comprising detecting local optical scattering from the sample.

4. A method of visualizing details in a sample, comprising:
   generating radiative and non-radiative signals in the sample at an excitation location using an excitation beam, the excitation beam being focused below a surface of the sample;
   interrogating the sample with an interrogation beam directed toward the excitation location of the sample, the interrogation beam being focused below the surface of the sample;
   detecting light from the sample, the detected light including a portion of the interrogation beam returning from the sample, wherein the detected light is indicative of the generated radiative and the non-radiative signals, wherein detecting the light includes detecting the generated radiative and non-radiative signals over time; and
   determining an evolution time of the detected generated radiative and non-radiative signals.

5. The method of claim 4, wherein generating radiative and non-radiative signals in the sample occurs at a plurality of regions in the sample, and the method further comprises identifying regions among the plurality of regions that belong to cell nuclei based on the determined evolution time.

6. The method of claim 4, further comprising determining, based on the determined evolution time, at least one of:
   a thermal diffusivity of the sample,
   a conductivity of the sample,
   a speed of sound in the sample,
   a temperature of the sample,
   a density of the sample,
   a heat capacity of the sample,
   an acoustic impedance of the sample,
   a tissue type of the sample, or
   molecular information of the sample.

7. The method of claim 4, further comprising:
   determining an average pre-excitation signal,
   determining an average post-excitation signal based on a predetermined portion of the detected signals over time, determining an amplitude based on a difference between the determined average pre-excitation signal and the determined average post-excitation signal.

8. The method of claim 1, wherein the value is a ratio of the detected generated radiative signals to the non-radiative signals.

9. The method of claim 1, further comprising redirecting a portion of the returned interrogation beam and detecting an interaction with the sample.

10. The method of claim 1, wherein a wavelength of the excitation beam is configured such that the sample absorbs two or more photons simultaneously, wherein a sum of energy of the two or more photons is equal to a predetermined energy or absorption.

11. A method of visualizing details in a sample, comprising:

generating radiative and non-radiative signals in the sample at an excitation location using an excitation beam, the excitation beam being focused below a surface of the sample;

interrogating the sample with an interrogation beam directed toward the excitation location of the sample, the interrogation beam being focused below the surface of the sample; and detecting light from the sample, the detected light including a portion of the interrogation beam returning from the sample, wherein the detected light is indicative of the generated radiative and the non-radiative signals, wherein a wavelength of the excitation beam is configured such that the sample absorbs two or more photons simultaneously, wherein the wavelength is equal to twice a predetermined wavelength.

12. The method of claim 11, wherein the predetermined wavelength is a wavelength in the ultraviolet (UV) range.

13. The method of claim 11, wherein the predetermined wavelength is a wavelength in the UVC range.

14. The method of claim 1, further comprising:

clustering the detected generated radiative and non-radiative signals based on shape using a clustering algorithm to determine features of the sample; and determining cluster centroids based on the clustered signals and determining an image based on the clustered signals, including determining one or more colors based on the clustered signals.

15. The method of claim 1, wherein interrogating the sample with an interrogation beam includes moving the interrogation beam over the sample to interrogate the sample over a plurality of regions over time.

16. The method of claim 15, further comprising estimating non-modulated scattering caused by the movement of the interrogation beam over spatial variations of the sample.

17. The method of claim 1, further comprising measuring or storing a plurality of filtered-instances of one of the generated signals, wherein the plurality of filtered-instances include an unfiltered instance of the signal and a filtered instance of the signal.

18. The method of claim 1, further comprising:

determining a first image based on the detected generated radiative signals;

determining a second image based on the detected generated non-radiative signals;

comparing the first and second images; and determining one or more modifications to a final image of the sample based on the comparison.

19. A method of visualizing details in a sample, comprising:

generating radiative and non-radiative signals in the sample at an excitation location using an excitation beam, the excitation beam being focused below a surface of the sample;

interrogating the sample with an interrogation beam directed toward the excitation location of the sample, the interrogation beam being focused below the surface of the sample; and detecting light from the sample, the detected light including a portion of the interrogation beam returning from the sample, wherein the detected light is indicative of the generated radiative and the non-radiative signals, wherein the interrogation beam includes a chirped-pulse; and spatially separating various wavelength components of the interrogation beam.

20. The method of claim 1, wherein detecting the light from the sample is performed using a plurality of detectors.

21. The method of claim 1, wherein the excitation beam is focused in an area that is smaller than an area in which the detection beam is focused.

22. A method of visualizing details in a sample, comprising:

generating radiative and non-radiative signals in the sample at an excitation location using an excitation beam, the excitation beam being focused below a surface of the sample;

interrogating the sample with an interrogation beam directed toward the excitation location of the sample, the interrogation beam being focused below the surface of the sample; and detecting light from the sample, the detected light including a portion of the interrogation beam returning from the sample, wherein the detected light is indicative of the generated radiative and the non-radiative signals, wherein the method is used in one or more of the following applications:

imaging of blood oxygen saturation;

imaging of tumor hypoxia;

imaging of wound healing, burn diagnostics, or surgery;

imaging of microcirculation;

blood oxygenation parameter imaging;

estimating blood flow in vessels flowing into and out of a region of tissue;

imaging of molecularly-specific targets;

imaging angiogenesis for pre-clinical tumor models;

clinical imaging of micro-and macro-circulation and pigmented cells;

imaging of the eye;

augmenting or replacing fluorescein angiography;

imaging dermatological lesions;

imaging melanoma;

imaging basal cell carcinoma;

imaging hemangioma;

imaging psoriasis;

imaging eczema;

imaging dermatitis;

imaging Mohs surgery;

imaging to verify tumor margin resections;

imaging peripheral vascular disease;

imaging diabetic and/or pressure ulcers;

burn imaging;

plastic surgery;

microsurgery;

imaging of circulating tumor cells;

imaging melanoma cells;

imaging lymph node angiogenesis;

imaging response to photodynamic therapies;

imaging response to photodynamic therapies having vascular ablative mechanisms;

imaging response to chemotherapeutics;

imaging response to anti-angiogenic drugs;

imaging response to radiotherapy;

estimating oxygen saturation using multi-wavelength photoacoustic excitation;

estimating venous oxygen saturation where pulse oximetry cannot be used;

estimating cerebrovenous oxygen saturation and/or central venous oxygen saturation;

estimating oxygen flux and/or oxygen consumption;

imaging vascular beds and depth of invasion in Barrett's esophagus and/or colorectal cancers;

functional imaging during brain surgery;

assessment of internal bleeding and/or cauterization verification;

imaging perfusion sufficiency of organs and/or organ transplants;

imaging angiogenesis around islet transplants;

imaging of skin-grafts;

imaging of tissue scaffolds and/or biomaterials to evaluate vascularization and/or immune rejection;

imaging to aid microsurgery;

guidance to avoid cutting blood vessels and/or nerves;

imaging of contrast agents in clinical or pre-clinical applications;

identification of sentinel lymph nodes;

non-or minimally-invasive identification of tumors in lymph nodes;

non-destructive testing of materials;

imaging of genetically-encoded reporters, wherein the genetically-encoded reporters include tyrosinase, chromoproteins, and/or fluorescent proteins for pre-clinical or clinical molecular imaging applications;

imaging actively or passively targeted optically absorbing nanoparticles for molecular imaging;

imaging of blood clots;

staging an age of blood clots;

replacing a catheterization procedure;

gastroenterological applications;

single-excitation pulse imaging over an entire field of view;

imaging of tissue;

imaging of cells;

imaging of scattered light from object surfaces;

imaging of absorption-induced changes of scattered light; or non-contact imaging of optical absorption.

23. A photoabsorption remote sensing system for imaging features in a sample, comprising:

an excitation light source configured to generate signals in the sample at an excitation location, the excitation light source being focused below a surface of the sample;

an interrogation light source configured to interrogate the sample and directed toward the excitation location of the sample, the interrogation light source being focused below the surface of the sample, wherein a portion of the interrogation light source returning from the sample is indicative of generated signals;

a detection source configured to detect light from the sample, wherein the detection source is configured to detect a portion of the interrogation light source returning from the sample, the returned portion of the interrogation light source being indicative of generated signals; and a processor configured to analyze the generated signals as a function of time and determine an image, the image being indicative of features in the sample.

24. A photoabsorption remote sensing system for imaging features in a sample, comprising:

an excitation light source configured to generate signals in the sample at an excitation location, the excitation light source being focused below a surface of the sample;

an interrogation light source configured to interrogate the sample and directed toward the excitation location of the sample, the interrogation light source being focused below the surface of the sample; and a detection source configured to detect light from the sample, wherein the detection source is configured to detect a portion of the interrogation light source returning from the sample, the returned portion of the interrogation light source being indicative of at least some of the generated signals; and a processor configured to analyze the generated signals as a function of time and determine an image, the image being indicative of features in the sample.

* * * * *